(12) United States Patent
Naudet et al.

(10) Patent No.: US 11,198,868 B2
(45) Date of Patent: Dec. 14, 2021

(54) CONTROL OF PLANT PESTS USING RNA MOLECULES

(71) Applicant: DEVGEN NV, Ghent (BE)

(72) Inventors: Yann Naudet, Ghent (BE); Myriam Beghyn, Ghent (BE); Lien De Schrijver, Ghent (BE); Isabelle Maillet, Ghent (BE); Annelies Philips, Ghent (BE)

(73) Assignee: DEVGEN NV, Ghent (BE)

( * ) Notice: Subject to any disclaimer, the term of this patent is extended or adjusted under 35 U.S.C. 154(b) by 0 days.

(21) Appl. No.: 16/756,298

(22) PCT Filed: Nov. 6, 2018

(86) PCT No.: PCT/US2018/059380
§ 371 (c)(1),
(2) Date: Apr. 15, 2020

(87) PCT Pub. No.: WO2019/103840
PCT Pub. Date: May 31, 2019

(65) Prior Publication Data
US 2020/0239891 A1   Jul. 30, 2020

(30) Foreign Application Priority Data

Nov. 27, 2017  (GB) ...................... 1719680

(51) Int. Cl.
*C12N 15/113* (2010.01)
*C07H 21/02* (2006.01)
*C12N 15/63* (2006.01)

(52) U.S. Cl.
CPC ........... *C12N 15/113* (2013.01); *C07H 21/02* (2013.01); *C12N 15/63* (2013.01); *C12N 2310/14* (2013.01)

(58) Field of Classification Search
CPC .......................... C12N 15/113; C12N 2310/14
See application file for complete search history.

(56) References Cited

U.S. PATENT DOCUMENTS

2012/0164205 A1* 6/2012 Baum ................ C12N 15/8286
424/409
2012/0240288 A1 9/2012 Jian et al.
2013/0291188 A1 10/2013 Bogaert et al.
2015/0004148 A1 1/2015 Raemaekers et al.
2015/0152432 A1 6/2015 Schon et al.
2015/0337329 A1 11/2015 Edgerton
2016/0060628 A1 3/2016 Beghyn et al.
2016/0230186 A1* 8/2016 Baum ................. C12N 15/113

FOREIGN PATENT DOCUMENTS

| WO | 2005110068 A2 | 11/2005 |
| WO | 2011040880 A1 | 4/2011 |
| WO | 2012/055982 A | 5/2012 |
| WO | 2015095774 A1 | 6/2015 |
| WO | 2016/118762 A | 7/2016 |
| WO | 2017106171 A1 | 6/2017 |
| WO | 2019206780 A1 | 10/2019 |

OTHER PUBLICATIONS

International Search Report for International Application No. PCT/US2018/059380 dated Mar. 8, 2019.
Front Physiol, vol. 6, 2015, VSR Kola et al., "Key Enzymes and Proteins of Crop Insects as Candidate for RNAi Based Gene Silencing," 119 available online at https://www.ncbi.nlm.nih.gov/pmc/articles/PMC4406143/pdf/fphys-06-00119.pdf.
Notification Concerning Transmittal of International Preliminary Report on Patentability cited in application No. PCT/US2018/059380 dated Jun. 11, 2020.
Ulrich, Julia, Application of RNA interference for the study of lethal genes and dynamic processes—Dissertation, Jul. 20, 2015, XP055546092.
Extended European Search Report for Application No. 18880570.9 dated Aug. 6, 2021.

* cited by examiner

*Primary Examiner* — Brian Whiteman
(74) *Attorney, Agent, or Firm* — BakerHostetler; Toni-Junell Herbert

(57) ABSTRACT

Disclosed are double stranded RNA (dsRNA) molecules that are toxic to insect pests. In particular, interfering RNA molecules capable of modulating expression of a pest insect target gene and that are toxic to the insect pest are provided. Further, methods of making and using the interfering RNA, for example as the active ingredient in an insecticidal composition or in a transgenic plant, to confer protection from insect damage are disclosed.

18 Claims, No Drawings
Specification includes a Sequence Listing.

SEQUENCE LISTING

<160> NUMBER OF SEQ ID NOS: 55

<210> SEQ ID NO 1
<211> LENGTH: 1284
<212> TYPE: DNA
<213> ORGANISM: Meligethes aeneus

<400> SEQUENCE: 1

```
atgtctcagc ttgaagataa gtcgatatgg gaggatgggg acgatacgct gggcgaagaa      60
gtcctcagga tgtccactga tgaaattgta agccgtacta ggcttttgga taacgaaata     120
aaaataatga aaagcgaggt tatgcgtatc aatcatgaat gcaagctca  aacagagaag     180
attaaagaga atactgaaaa gattaaagtg aataaaactc ttccttactt agtttctaat     240
gtaatagaat tgttagatgt agatccacaa gaagaagaag aagatggggc tgtagttgac     300
ttagattctc aacgtaaagg taaatgcgct gttgtcaaaa cctctacacg tcaaacgtac     360
tttttgcctg tcattgggtt agttgatgag gaaaaattga accaggcga  tcttgtagga     420
gtaaacaaag actcttactt aattcttgaa actcttcctg cagaatatga tgccagagtc     480
aaagcaatgg aagtagatga acgccccact gaacaatatt ctgatattgg tggtttagac     540
aaacaaatcc aagagttaat tgaagctgta gttcttccaa tgacacacaa agaaaaattt     600
gtaaacctcg gcattcaccc ccctaaagga gtattattat atggtccccc tggcacaggt     660
aaaaccctac ttgccagagc atgtgctgca cagacaaaat caacattttt aaaacttgct     720
gggcctcagt tggtccaaat gtttattggt gatggtgcca aattggtgcg tgatgctttt     780
gcactcgcca agaaaaagc  ccctgctatt attttcattg atgagttgga tgccattggt     840
acaaaacgtt tgattctga  aaagctggt  gatcgtgagg tacaacgtac catgttagag     900
ttgctgaacc agttggatgg cttcagttcc actgctgata ttaaggttat tgctgctact     960
aatagagtgg atattttgga tcctgcgctt ttgagatctg aagattgga  tagaaagatt    1020
gagttccctc atccaaatga agaagcaaga gcaagaatca tgcaaattca ctcaagaaaa    1080
atgactgtaa acccagatgt gaactttgaa gaattggcca ggtctaccga tgactttaat    1140
ggggcccaat gtaaggcagt gtgtgttgaa gctggtatga ttgctttgag aagaagcgcc    1200
acagctgtca cccatgaaga ttacatggat gctattatgg aagtacaggc caagaagaag    1260
gccaacttaa actactatgc ttaa                                           1284
```

<210> SEQ ID NO 2
<211> LENGTH: 1284
<212> TYPE: DNA
<213> ORGANISM: Sitophilus oryzae

<400> SEQUENCE: 2

```
atggctacgc tagaagataa ggcgatatgg gacgacggag aagaagcact cggcgaagaa      60
gtactgagaa tgtctaacga cgagattata agcagaacta gactgttgga caacgaaatt     120
aaaataatga aaagcgaagt gatgagaata accacgagc  tgcaagccca aaacgaaaag     180
attaaggaga acacggagaa aattaaagtt aataaaacct taccatattt agtttcaaat     240
gttattgaat tgctcgatgt ggacccacaa gaagaggaag aggatgggc  tgttgttgat     300
ttagattctc aagaaaaagg aaaatgtgca gttgtaaaaa catcaacacg ccaaacctac     360
tttcttcctg ttatcggact tgttgatgaa gaaaaattaa accaggtga  tttggtcggt     420
gtgaataagg attcataccct aattttggag acccttcctg ctgaatacga tgccagagtt     480
aaagctatga aggttgatga agaccaaca  gaacaatact cagatattgg tggcttggac     540
aaacaaattc aagagctcat agaggctgta gtcctcccaa tgacacacaa agataaattt     600
gtcaatttag aatacaaacc tcctaaaggg gtattgttgt atggacctcc aggaacagga     660
aagactctgc tggctagggc ttgtgctgcc caaaccaaat caactttctt gaaattggca     720
```

```
gggcccccagt tggttcagat gtttattggt gacggtgcaa aactagttag agatgctttt    780
gcattggcca agagaaaagc acctgctatt atttttgtcg atgaactgga tgcaattggt    840
actaaaagat tcgattctga aaaggctggt gatcgggaag tacagagaac tatgttggaa    900
ttattgaatc agttagatgg tttcagttcg acagcagata ttaaggttat agcagcaact    960
aatcgtgttg acattctcga tccagcattg ttgcgatccg gcagattgga tcgtaaaatt   1020
gaattccctc atccgaatga agaagccaga gcgagaatta tgcagattca ttcgagaaaa   1080
atgacagtaa accctgacgt aaactttgag gaattggcta gatcaacgga tgattttaat   1140
ggagcccagt gtaaagctgt atgtgtggag gctggtatga tagctttgag aaggaacgct   1200
actgtagtga cgcacgaaga ctacatggac gctataatgg aagtgcaagc gaaaaagaaa   1260
gccaatctta attattatgc ttaa                                           1284

<210> SEQ ID NO 3
<211> LENGTH: 1284
<212> TYPE: DNA
<213> ORGANISM: Sitophilus granaries

<400> SEQUENCE: 3
atggctacgc tagaagacaa agcgatatgg gacgacggag aagaagcact aggcgaagaa     60
gtactgagaa tgtctaacga cgagattata agcagaacta gactgttgga caacgaaatt    120
aaaattatga aagcgaagt gatgagaata aaccacgaat acaagctcga gacgaaaag    180 attaaggaaa acacggagaa aatcaaagtt aataaaactt taccgtatct agtttcaaat    240
gttatcgaac tacttgatgt agatccacaa gaagaggaag aagatggagc tgttgtggat    300
ttagattctc aaagaaaagg aaaatgtgca gttgtaaaga catcaacgcg ccaaacatat    360
tttcttcctg ttattggact tgtcgacgaa gaaaaattga aacctggtga tctggtaggt    420
gttaacaagg actcttacct tattttggag acactgccag ctgaatatga tgccagagtt    480
aaagctatgg aggttgatga agaccaaca gaacagtact cagacattgg aggtttggat    540
aaacaaattc aagagctcat agaggctgta gtcctcccaa tgacacataa agataaattt    600
gtcaatttag gaatccaacc tcctaaaggg gtattgttgt atggacctcc aggaacagga    660
aagactcttc tggctagggc atgtgctgcc caaacaaaat caacattctt gaaattagca    720 gggcccccaat tagttcagat gtttatcggc gacggtgcaa aactagtgag ggatgctttt    780
gcgttggcca agagaaaagt accggctatt atttttgtcg atgagctgga tgcaattggt    840
acgaaaagat tcgattctga aaaggctggt gataggaag tacaaagaac tatgttagaa    900
ttattgaatc agttagatgg tttcagttca acagcagata ttaaggttat agcagcaacc    960
aatcgtgttg atattctcga tccagcatta ttgcgatcgg gtaggttgga tcgtaaaatt   1020
gaattccccc atccgaatga agaagccaga gcgagaatta tgcagattca ttcaagaaaa   1080
atgacggtaa accctgatgt aaactttgaa gaattggcta gatctactga tgattttaat   1140
ggagctcagt gtaaagctgt atgtgtggag gctggtatga tagctttgag aagaaacgct   1200
accgcagtga cacacgagga ctacatggac gctataatgg aagtgcaagc taaaaagaaa   1260
gccaatctta attattatgc ttaa                                           1284

<210> SEQ ID NO 4
<211> LENGTH: 1284
<212> TYPE: DNA
<213> ORGANISM: Ceuthorrhynchus assimilis
```

<400> SEQUENCE: 4

```
atgactacat tagacgataa atctttgtgg gaggacggtg aagaagccct aggcgaagaa      60
gtgttgcgaa tgtccagcga tgaaatagtt agcagaacaa gactgatgga caatgaaatc     120
aaaataatga aaagcgaggt gatgaggatt aatcacgaat gcaagcgca aaacgagaag      180
attaaagaaa acactgagaa aataaaagta aacaaaaccc tgccttattt ggtgtcgaat     240
gtgattgaac ttttggatgt ggatccgcaa gaagaggaag aagatggagc tgttgttgat     300
ttggattcac aaagaaaagg aaagtgtgca gtagtaaaaa catccactcg ccaaacctat     360
ttccttcctg taatagggct cgtagatgaa gaaaaattga gccgggaga tttggttggt      420
gtcaacaaag attcttatct tattttggaa actttgccag ctgaatatga tgccagagta     480
aaagctatgg aggttgatga agaccaaca gaacaatact cagacatcgg tggcttagac      540
aaacaaatac aagaattaat cgaagcagtg gtattgccaa tgactcacaa agacaagttt     600
gttaacttgg gcattcaacc tccaaaaggt gttttattat atgggccacc aggtactgga     660
aaaacactac tggctcgagc ttgtgccgct caaaccaaat cgactttcct gaaactggca     720
ggtcctcagt tagttcaaat gtttattggc gacggtgcga aattagtcag agacgctttt     780
gctttggcca aggaaaaagt tccagcaatt attttttatcg atgaattgga cgctatcggt     840
actaaacgtt tcgattctga aaagctgga gacaggaag ttcaaaggac catgttggaa      900
cttttgaatc agttagacgg tttcagttcc acagcggata ttaaagtaat tgcagccaca     960
aatcgtgtag acattttgga tcctgccctg ttaagatcgg gacgtttgga tcgtaaaatc    1020
gaatttccac atccaaatga ggaggccaga gctaggatta tgcaaattca ttcaaggaaa    1080
atgactgtta atcctgatgt taattttgaa gaattggcta ggagtactga tgacttcaat    1140
ggagcccaat gtaaagctgt ctgcgttgaa gctggtatga tcgctctgag aaggaatgct    1200
acagcagtga ctcacgaaga ttatatggat gctatcatgg aggtacaggc taagaagaag    1260
gctaacctca attactatgc ttaa                                            1284
```

<210> SEQ ID NO 5
<211> LENGTH: 1281
<212> TYPE: DNA
<213> ORGANISM: Rhyzopertha dominica

<400> SEQUENCE: 5

```
atgtcgactc tggaagatgc atcaatttgg gatgaaggag aatcccttgg tgaagacgtt      60
cttcgtatgt ctacggatga aatagtaagt cgcacccggc ttctagacaa tgagattaag     120
atcatgaaaa gtgaagtcat gcgtattaat catgaactcc aagcacaaaa cgaaagata     180
aaagagaaca cagagaagat taagttaac aagaccttac cctatctagt ttcaaatgtt      240
atcgaactgt tggatgtaga tccccaggaa gaagaagaag acggagctgt tgttgattta     300
gacgcacaaa gaaagggcaa atgtgctgta gtcaagacgt ccactcgtca aacttacttt     360
ctgccagtta tcgattggt cgatgaagag aaacttaaac cgggtgatct cgttggtgtg     420
aacaaagatt cttatttaat actggaaact cttcctgctg agtatgatgc tagagttaaa     480
gcaatggaag tagacgaacg gcctacggaa cagtattcgg atattggagg tttggataag    540
caaatacaag agttaataga agctgttgta cttcctatga cacacaaaga taaatttctt     600
aacctgggta ttcacccacc gaagggtgtc cttctgtatg ggccacctgg aacaggaaaa    660
actctgctag caagagcatg tgctgcacaa acaaagtcaa cgttttttaaa gctggctggg    720
```

```
ccacagctgg tgcagatgtt cataggtgac ggagctaagc ttgtaaggga tgcatttgca      780
ctggctaagg agaagtctcc tgctatcata tttatcgatg aactggatgc tataggtaca      840
aaacgcttcg attctgaaaa ggcaggggat cgtgaagtgc aacgtacgat gttagaacta      900
cttaaccaac ttgacggttt ttcatctaca gcagacatta agtaattgc tgccaccaat       960 agagtcgaca tcttagatcc tgccctgcta cgttctggtc gtttagatag aaagattgag     1020
tttccacatc ccaatgagga agcaagggcc agaattatgc agatacattc acgaaaaatg     1080
acagtgaatc ccgatgttaa ttttgaagaa ctggcaaggt caactgacga tttcaatggt     1140
gcccaatgta agctgtgtg tgttgaggcg ggaatgattg ccttgagaag gaatgctact      1200
gcagtaacac atgaagatta catggatgca ataatggagg ttcaggctaa aagaaggcc      1260 aatcttaatt attatgctta g                                              1281

<210> SEQ ID NO 6
<211> LENGTH: 504
<212> TYPE: DNA
<213> ORGANISM: Phyllotreta nemorum

<400> SEQUENCE: 6
gccttggcca agagaaagc ccctgctata atattcatcg acgaattgga cgccatcggt        60
acgaagcgat tcgactccga gaaagccggc gacagggaag tccaaagaac catgttggaa     120
ctgttgaacc aactggacgg tttcagctcc acttccgaca tcaaagtcat gcagctacg      180 aatcgtgtgg atattctgga tcccgctctg cttcggtctg gtcggttgga caggaagatc    240
gaattcccgc atcccaacga gaggcgagg gcgagaatca tgcagattca ctccaggaaa     300
atgacggtca acccggacgt gaacttcgag gaattggcta gatctacgga cgacttcaac   360
ggggctcagt gtaaggctgt gtgcgtcgaa gctggtatga tcgctctcag acgtaacgcc    420
actgcggtaa cgcacgagga ctacatggat gctattatgg aagttcaagc taagaaaaag    480
gctaatctta attattacgc ctaa                                             504

<210> SEQ ID NO 7
<211> LENGTH: 1284
<212> TYPE: DNA
<213> ORGANISM: Psylliodes chrysocephala

<400> SEQUENCE: 7
atgtcgactt tagaagataa atcgatctgg gaagacggcg aagaagcgct aggtgaagaa       60
gttctcagaa tgtctaccga tgaaatagtt agtcgtactc gtttattgga caatgagatc     120
aaaataatga agagtgaagt aatgagaata atcacgaat tacaagcaca gaatgagaag     180
atcaaagaga acacgaaaaa aataaaagta aacaaaacgt tgccttattt ggtgtctaac    240
gtgatagaac tgttagatgt cgatccccag gaagaggaag aagacggtgc agtggtagat     300
ttggattctc aaagaaaagg aaaatgtgca gtagttaaaa catcaacccg ccaaacttac     360
tttctgccag ttatagggct ggttgatgag gaaaagttga agcctggtga tttagttggt     420
gtcaacaaag actcttatct cattttggaa acgctgcctg ccgagtacga tgccagagtt    480
aaagctatgg aggtggatga gagacctgct gaacagtact cagatattgg aggtttagat    540
aaacaaatcc aagaactgat tgaagctgtt gtgttaccaa tgacccataa agataaattt    600
gttaatttgg gtattcatcc cccaaaaggc gttttactat acgggccacc tggaactgga    660
aaacccctcc ttgccagagc atgtgcagct caaacaaaat caaccttctt aaaattagct    720
ggcccccaat tagtccagat gtttattggt gacggcgcca agcttgtgag agatgcattc   780
```

-continued

```
gctttagcca aagaaaaatc tcccgctatc atatttatcg atgaactgga cgcaataggc    840
acaaaaagat tcgattctga gaaagcgggt gacagggaag tgcaacgtac tatgttggag    900
ttgctgaacc agctggatgg gttcagttca accgccgata tcaaagtgat agctgctacc    960
aatcgtgtcg atattttaga ccctgctctg cttcgatctg gtagattaga cagaaagata   1020
gaattcccgc atcccaatga agaagcgagg gctagaatca tgcagattca ctccaggaaa   1080
atgactgtca atcctgatgt gaattttgaa gaactggcta ggtctacaga tgactttaat   1140
ggagcccagt gcaaggctgt gtgtgttgaa gctggtatga ttgctttgag acgtaacgct   1200
aatgccgtca cacatgaaga ttatatggat gctataatgg aagtgcaagc caagaagaag   1260
gcaaatctta attactatgc ttag                                          1284
```

<210> SEQ ID NO 8
<211> LENGTH: 1284
<212> TYPE: DNA
<213> ORGANISM: Phyllotreta striolata

<400> SEQUENCE: 8

```
atgtcgacct tagaagacaa atcgatttgg gaagacggcg aggaagcgct cggcgaggaa     60
gttttaagaa tgtccactga cgttatcata ggtcatacgc gattgctgga caatgagatc    120
aaaataatga agagcgaagt gatgcgaata aaccacgaac tgcaagcgca aaacgagaaa    180
atcaaagaaa acaccgagaa gataaaagtg aacaaaacct tgccttactt ggtctcgaac    240
gtaattgaac tgttggacgt agatccccag gaagaggaag aggacggtgc tgtagtcgat    300
ttggattctc agagaaaagg gaaatgcgct gtagttaaaa cgtccacgag acagacctat    360
ttcctacccg tgatagggct ggtcgatgag gagaaactga aaccgggaga tctagtggga    420
gtcaacaaag actcgtatct aattctggaa acattacctg cagagtacga tgcgagagtc    480
aaggccatgg aagtcgacga aaggccttct gaacagtatt ccgatatcgg aggtttagat    540
aagcaaatac aagaacttat cgaggctgtt gtactaccta tgactcataa agacaagttc    600
gttaacttgg gaattcatcc tcccaaaggt gttctccttt acggtccccc gggtaccggt    660
aaaaccctcc tagccagagc ctgcgccgcc caaaccaaat caactttcct caaactggcc    720
ggtcctcagt tagtccagat gttcataggc gacggcgcca agttagtccg agacgccttc    780
gccttggcca aagagaaggc acccgctata atattcatcg acgagctgga cgccatcggt    840
acgaagcgat tcgactcgga gaaagccgga gaccgggagg tccaacgaac catgttggaa    900
ctgctcaacc aactggacgg cttcagctcg acatccgaca tcaaagtcat agcggctacg    960
aatcgcgtgg atattctgga tcccgccctg ctgcggtccg gaaggttgga ccggaagatc   1020
gagttcccgc atcccaacga agaggcgcga gcgagaatca tgcagattca ctccagaaaa   1080
atgacggtta acccggacgt gaacttcgag gaattggcca ggtctactga tgacttcaat   1140
ggggcccagt gtaaggctgt gtgtgtcgaa gctggaatga tcgctctcag acgtaacgcc   1200
actgctgtga ctcacgagga ctacatggat gctattatgg aagttcaagc taagaaaaag   1260
gcgaatctga attattacgc ctaa                                          1284
```

<210> SEQ ID NO 9
<211> LENGTH: 1284
<212> TYPE: DNA
<213> ORGANISM: Diabrotica virgifera

<400> SEQUENCE: 9

```
atggctactc ttgaagatgt ttctatttgg gaagatggag aggaagcatt aggtgaagag      60
gttttacgaa tgtccactga tgaaatagtt agccggacac gtttactaga caatgaaatt     120
aaaataatga gagtgaagt tatgagaatc aatcatgaat tacaagccca aaatgagaaa     180
ataaaggaga atactgagaa aattaaagtg aacaaaacct taccgtactt ggtgtccaat     240
gtaatagaac tgttagatgt ggatccccaa gaggaagagg aagatggtgc agttgttgat     300
ctggactcac aaagaaaagg aaaatgtgct gttgttaaaa cttccactag acaaacctac     360
tttttaccag tgataggtct ggtggacgag agaagttaa agccaggtga tttggtagga     420
gtaaacaaag attcatacct tattttggaa acattacctg ctgaatatga tgccagagtt     480
aaagctatgg aagtagatga agaccaact gaacagtatt cagacattgg aggtctagat     540
aaacaaatcc aagaattaat tgaagctgtt gttttaccta tgactcacaa agataaattt     600
gttaatttgg gtatacatcc accaaaaggt gtgttgttat atggtcccccc tggtacagga     660
aagactcttt tggccagagc ttgtgctgca caaaccaaat caacatttttt gaaattggct     720
ggtcctcaac tcgttcaaat gttcattgga gatggtgcca acttgtcag agatgctttt     780
gctcttgcca aagagaaggc accagctata atattcattg atgaattaga tgctatcggt     840
accaaaagat tgattctga aaagctgga gacagaaag tccagcgtac tatgttagaa     900
cttcttaacc agttggatgg attcagttca acagctgata ttaaggttat agctgctacc     960
aatcgtgtag atatattgga tcctgctcta ctccgttctg gtagattaga tcgtaaaata    1020
gagttccctc accccaatga ggaagcgaga gctagaatca tgcaaattca ttcaagaaaa    1080
atgacagtca atcctgatgt caactttgag gaattagcaa gatcaacaga tgacttcaat    1140
ggagctcaat gtaaagcagt ctgtgttgag gcaggtatga tagccctaag aaggagtgct    1200
acagctgtaa ctcatgaaga ttatatggat gcaattatgg aggttcaagc taagaagaag    1260
gcaaatctta attattatgc ttaa                                           1284
```

<210> SEQ ID NO 10
<211> LENGTH: 1394
<212> TYPE: DNA
<213> ORGANISM: Leptinotarsa decemlineata

<400> SEQUENCE: 10

```
ttaaacagtg gctaaagcta aaactattat ttgaaatgtc gtctactcta gaagataaag      60
ctatctggga agatgggaa gaatcattgg gggaggaagt tctgaggatg tcgactgatg     120
aaatagtcag ccggacgcgt ttactcgata tgaaatcaa aataatgaag agcgaagtaa     180
tgagaataaa ccatgaactc caagcccaaa acgaaaaaat caagaaaaac actgaaaaga     240
taaaggtaaa taaaacgcta ccttacttgg tatctaatgt tatagaactg ctagatgtgg     300
accctcaaga ggaagaagaa gacggggcag ttgtagactt ggattctcaa agaaagggaa     360
aatgtgccgt tgtaaaaaca tctactcgtc aaacatattt tctaccagta atcgggctcg     420
ttgatgaaga aaagctcaaa cctggagatt tagtgggtgt gaacaaagat tcttatctta     480
tcctagaaac attaccagcg gagtatgatg caagagtaaa agctatggaa gttgatgaaa     540
gaccaactga acaatactca gacattggtg ggctggacaa acaaatccag gaacttattg     600
aagcagtcgt attgccaatg acccacaagg ataaatttgt taatcttggg attcatccac     660
ctaaaggagt cttgttatat ggaccccccag gaactggaaa aactttgttg gctagagcat     720
```

-continued

| | |
|---|---|
| gtgctgctca gacaaaatca acatttttga aactagctgg accccaatta gttcagatgt | 780 |
| tcataggaga tggtgctaaa cttgtaagag atgcttttgc gttagccaag gaaaaggcac | 840 |
| cagctataat tttcatcgat gaattggatg ctactggtac gaaacgtttt gattctgaga | 900 |
| aggctgggga tcgtgaagta caacgtacaa tgttgggagc ttttgaatca gttggatggg | 960 |
| tttagttcaa cagctgatat aaaagtaatt gcagctaccc atcgggttga ttttctagat | 1020 |
| cctgctttac tttgatcagg tcggttagat tgtaaaaaag aatttcctcc tccaaaagaa | 1080 |
| gaaggtaggg caagaataat gcaaattccc tcaagaaaaa agactgttaa ccccgaagta | 1140 |
| aactttgaag aattgggtag atcccctggg ggctttaacg ggggtccggg taaagccgtt | 1200 |
| tgttttgaag ccggtttgat agctttggga agaaaagccc ccgctgtttc ccctgaagat | 1260 |
| tttttggatg ttttttttgga agttcaagcc cagaaaaaag ggaattttaa ttttttttt | 1320 |
| taatttcccg cctacagata taaattttg ttttggtta aaaaaaaaaaa aaaaaaaaa | 1380 |
| aaaaaaacaa aaaa | 1394 |

<210> SEQ ID NO 11
<211> LENGTH: 701
<212> TYPE: DNA
<213> ORGANISM: Meligethes aeneus

<400> SEQUENCE: 11

| | |
|---|---|
| acgtactttt tgcctgtcat tgggttagtt gatgaggaaa aattgaaacc aggcgatctt | 60 |
| gtaggagtaa acaaagactc ttacttaatt cttgaaactc ttcctgcaga atatgatgcc | 120 |
| agagtcaaag caatggaagt agatgaacgc cccactgaac aatattctga tattggtggt | 180 |
| ttagacaaac aaatccaaga gttaattgaa gctgtagttc ttccaatgac acacaaagaa | 240 |
| aaatttgtaa acctcggcat tcaccccct aaaggagtat tattatatgg tcccctggc | 300 |
| acaggtaaaa ccctacttgc cagagcatgt gctgcacaga caaaatcaac attttaaaa | 360 |
| cttgctgggc tcagttggt ccaaatgttt attggtgatg tgccaaatt ggtgcgtgat | 420 |
| gcttttgcac tcgccaaaga aaaagcccct gctattattt tcattgatga gttggatgcc | 480 |
| attggtacaa acgttttga ttctgagaaa gctggtgatc gtgaggtaca acgtaccatg | 540 |
| ttagagttgc tgaaccagtt ggatggcttc agttccactg ctgatattaa ggttattgct | 600 |
| gctactaata gagtggatat tttggatcct gcgcttttga gatctggaag attggataga | 660 |
| aagattgagt ccctcatcc aaatgaagaa gcaagagcaa g | 701 |

<210> SEQ ID NO 12
<211> LENGTH: 720
<212> TYPE: DNA
<213> ORGANISM: Sitophilus oryzae

<400> SEQUENCE: 12

| | |
|---|---|
| taaaaccagg tgatttggtc ggtgtgaata aggattcata cctaattttg gagacccttc | 60 |
| ctgctgaata cgatgccaga gttaaagcta tggaggttga tgaaagacca acagaacaat | 120 |
| actcagatat tggtggcttg gacaaacaaa ttcaagagct catagaggct gtagtcctcc | 180 |
| caatgacaca caaagataaa tttgtcaatt taggaataca acctcctaaa ggggtattgt | 240 |
| tgtatggacc tccaggaaca ggaaagactc tgctggctag gcttgtgct gcccaaacca | 300 |
| aatcaacttt cttgaaattg gcagggcccc agttggttca gatgtttatt ggtgacggtg | 360 |
| caaaactagt tagagatgct tttgcattgg ccaaagagaa agcacctgct attatttttg | 420 |
| tcgatgaact ggatgcaatt ggtactaaaa gattcgattc tgaaaaggct ggtgatcggg | 480 |

```
aagtacagag aactatgttg gaattattga atcagttaga tggtttcagt tcgacagcag    540
atattaaggt tatagcagca actaatcgtg ttgacattct cgatccagca ttgttgcgat    600
ccggcagatt ggatcgtaaa attgaattcc ctcatccgaa tgaagaagcc agagcgagaa    660
ttatgcagat tcattcgaga aaaatgacag taaaccctga cgtaaacttt gaggaattgg    720
```

<210> SEQ ID NO 13
<211> LENGTH: 742
<212> TYPE: DNA
<213> ORGANISM: Sitophilus granaries

<400> SEQUENCE: 13

```
agctgaatat gatgccagag ttaaagctat ggaggttgat gaaagaccaa cagaacagta     60
ctcagacatt ggaggtttgg ataaacaaat tcaagagctc atagaggctg tagtcctccc    120
aatgacacat aaagataaat ttgtcaattt aggaatccaa cctcctaaag ggtattgtt    180 gtatggacct ccaggaacag gaaagactct tctggctagg gcatgtgctg cccaaacaaa    240
atcaacattc ttgaaattag cagggcccca attagttcag atgtttatcg gcgacggtgc    300
aaaactagtg agggatgctt tgcgttggc caaagagaaa gtaccggcta ttatttttgt    360
cgatgagctg gatgcaattg gtacgaaaag attcgattct gaaaaggctg gtgataggga    420
agtacaaaga actatgttag aattattgaa tcagttagat ggtttcagtt caacagcaga    480
tattaaggtt atagcagcaa ccaatcgtgt tgatattctc gatccagcat tattgcgatc    540
gggtaggttg gatcgtaaaa ttgaattccc ccatccgaat gaagaagcca gagcgagaat    600
tatgcagatt cattcaagaa aaatgacggt aaaccctgat gtaaactttg aagaattggc    660
tagatctact gatgatttta atggagctca gtgtaaagct gtatgtgtgg aggctggtat    720
gatagctttg agaagaaacg ct                                             742
```

<210> SEQ ID NO 14
<211> LENGTH: 755
<212> TYPE: DNA
<213> ORGANISM: Ceuthorrhynchus assimilis

<400> SEQUENCE: 14

```
ccctgcctta tttggtgtcg aatgtgattg aacttttgga tgtggatccg caagaagagg     60
aagaagatgg agctgttgtt gatttggatt cacaaagaaa aggaaagtgt gcagtagtaa    120
aaacatccac tcgccaaacc tatttccttc ctgtaatagg gctcgtagat aagaaaaat    180 tgaagccggg agatttggtt ggtgtcaaca aagattctta tcttattttg gaaactttgc    240
cagctgaata tgatgccaga gtaaaagcta tggaggttga tgaaagacca acagaacaat    300
actcagacat cggtggctta gacaaacaaa tacaagaatt aatcgaagca gtggtattgc    360
caatgactca caaagacaag tttgttaact tgggcattca acctccaaaa ggtgttttat    420
tatatgggcc accaggtact ggaaaaacac tactggctcg agcttgtgcc gctcaaacca    480
aatcgacttt cctgaaactg gcaggtcctc agttagttca aatgtttatt ggcgacggtg    540
cgaaattagt cagagacgct tttgctttgg ccaaggaaaa agttccagca attattttta    600
tcgatgaatt ggacgctatc ggtactaaac gtttcgattc tgaaaaagct ggagacaggg    660
aagttcaaag gaccatgttg gaactttga atcagttaga cggtttcagt tccacagcgg    720
atattaaagt aattgcagcc acaaatcgtg tagac                               755
```

<210> SEQ ID NO 15
<211> LENGTH: 656
<212> TYPE: DNA
<213> ORGANISM: Rhyzopertha dominica

<400> SEQUENCE: 15

```
acaaagaaag ggcaaatgtg ctgtagtcaa gacgtccact cgtcaaactt actttctgcc      60
agttatcgga ttggtcgatg aagagaaact taaaccgggt gatctcgttg gtgtgaacaa     120
agattcttat ttaatactgg aaactcttcc tgctgagtat gatgctagag ttaaagcaat     180
ggaagtagac gaacggccta cggaacagta ttcggatatt ggaggtttgg ataagcaaat     240
acaagagtta atagaagctg ttgtacttcc tatgacacac aaagataaat ttcttaacct     300
gggtattcac ccaccgaagg gtgtccttct gtatgggcca cctggaacag gaaaaactct     360
gctagcaaga gcatgtgctg cacaaacaaa gtcaacgttt ttaaagctgg ctgggccaca     420
gctggtgcag atgttcatag gtgacggagc taagcttgta agggatgcat ttgcactggc     480
taaggagaag tctcctgcta tcatatttat cgatgaactg gatgctatag gtacaaaacg     540
cttcgattct gaaaaggcag gggatcgtga agtgcaacgt acgatgttag aactacttaa     600
ccaacttgac ggttttttcat ctacagcaga cattaaagta attgctgcca ccaata       656
```

<210> SEQ ID NO 16
<211> LENGTH: 315
<212> TYPE: DNA
<213> ORGANISM: Phyllotreta nemorum

<400> SEQUENCE: 16

```
tccaaagaac catgttggaa ctgttgaacc aactggacgg tttcagctcc acttccgaca      60
tcaaagtcat agcagctacg aatcgtgtgg atattctgga tcccgctctg cttcggtctg     120
gtcggttgga caggaagatc gaattcccgc atcccaacga agaggcgagg gcagagaatca    180
tgcagattca ctccaggaaa atgacggtca acccggacgt gaacttcgag gaattggcta     240
gatctacgga cgacttcaac ggggctcagt gtaaggctgt gtgcgtcgaa gctggtatga     300
tcgctctcag acgta                                                      315
```

<210> SEQ ID NO 17
<211> LENGTH: 701
<212> TYPE: DNA
<213> ORGANISM: Psylliodes chrysocephala

<400> SEQUENCE: 17

```
ctatggaggt ggatgagaga cctgctgaac agtactcaga tattggaggt ttagataaac      60
aaatccaaga actgattgaa gctgttgtgt taccaatgac ccataaagat aaatttgtta     120
atttgggtat tcatccccca aaaggcgttt tactatacgg gccacctgga actggaaaaa     180
ccctccttgc cagagcatgt gcagctcaaa caaaatcaac cttcttaaaa ttagctggcc     240
cccaattagt ccagatgttt attggtgacg gcgccaagct tgtgagagat gcattcgctt     300
tagccaaaga aaaatctccc gctatcatat ttatcgatga actggacgca ataggcacaa     360
aaagattcga ttctgagaaa gcgggtgaca gggaagtgca acgtactatg ttggagttgc     420
tgaaccagct ggatgggttc agttcaaccg ccgatatcaa agtgatagct gctaccaatc     480
gtgtcgatat tttagaccct gctctgcttc gatctggtag attagacaga aagatagaat     540
tcccgcatcc caatgaagaa gcgagggcta gaatcatgca gattcactcc aggaaaatga     600
```

```
ctgtcaatcc tgatgtgaat tttgaagaac tggctaggtc tacagatgac tttaatggag      660
cccagtgcaa ggctgtgtgt gttgaagctg gtatgattgc t                          701

<210> SEQ ID NO 18
<211> LENGTH: 720
<212> TYPE: DNA
<213> ORGANISM: Phyllotreta striolata

<400> SEQUENCE: 18
tcgaggctgt tgtactacct atgactcata agacaagtt cgttaacttg ggaattcatc       60
ctcccaaagg tgttctcctt tacgtcccc cgggtaccgg taaaaccctc ctagccagag      120
cctgcgccgc ccaaaccaaa tcaactttcc tcaaactggc cggtcctcag ttagtccaga     180
tgttcatagg cgacggcgcc aagttagtcc gagacgcctt cgccttggcc aaagagaagg     240
cacccgctat aatattcatc gacgagctgg acgccatcgg tacgaagcga ttcgactcgg     300
agaaagccgg agaccgggag gtccaacgaa ccatgttgga actgctcaac caactggacg     360
gcttcagctc gacatccgac atcaaagtca tagcggctac gaatcgcgtg gatattctgg     420
atcccgccct gctgcggtcc ggaaggttgg accggaagat cgagttcccg catcccaacg     480
aagaggcgcg agcgagaatc atgcagattc actccagaaa aatgacggtt aacccggacg     540
tgaacttcga ggaattggcc aggtctactg atgacttcaa tggggcccag tgtaaggctg     600
tgtgtgtcga agctggaatg atcgctctca gacgtaacgc cactgctgtg actcacgagg     660
actacatgga tgctattatg gaagttcaag ctaagaaaaa ggcgaatctg aattattacg     720

<210> SEQ ID NO 19
<211> LENGTH: 762
<212> TYPE: DNA
<213> ORGANISM: Diabrotica virgifera

<400> SEQUENCE: 19
ctggactcac aaagaaaagg aaaatgtgct gttgttaaaa cttccactag acaaacctac       60
tttttaccag tgataggtct ggtggacgag gagaagttaa agccaggtga tttggtagga     120
gtaaacaaag attcatacct tattttggaa acattacctg ctgaatatga tgccagagtt     180
aaagctatgg aagtagatga agaccaact gaacagtatt cagacattgg aggtctagat      240
aaacaaatcc aagaattaat tgaagctgtt gttttaccta tgactcacaa agataaattt     300
gttaatttgg gtatacatcc accaaaaggt gtgttgttat atggtccccc tggtacagga     360
aagactcttt tggccagagc ttgtgctgca caaaccaaat caacattttt gaaattggct     420
ggtcctcaac tcgttcaaat gttcattgga gatggtgcca aacttgtcag agatgctttt     480
gctcttgcca agagaaggc accagctata atattcattg atgaattaga tgctatcggt     540
accaaaagat ttgattctga gaaagctgga gacagagaag tccagcgtac tatgttagaa     600
cttcttaacc agttggatgg attcagttca acagctgata ttaaggttat agctgctacc     660
aatcgtgtag atatattgga tcctgctcta ctccgttctg gtagattaga tcgtaaaata     720
gagttccctc accccaatga ggaagcgaga gctagaatca tg                         762

<210> SEQ ID NO 20
<211> LENGTH: 701
<212> TYPE: RNA
<213> ORGANISM: Meligethes aeneus
```

<400> SEQUENCE: 20

```
acguacuuuu ugccugucau ugggutaguu gaugaggaaa aauugaaacc aggcgaucuu      60
guaggaguaa acaaagacuc uuacuuaauu cuugaaacuc uuccugcaga auaugaugcc     120
agagucaaag caauggaagu agaugaacgc cccacugaac aauauucuga uauuggugggu   180
uuagacaaac aaauccaaga guuaauugaa gcuguaguuc uuccaaugac acacaaagaa    240
aaauuuguaa accucggcau caccccccu aaaggaguau auuuauaugg uccccccuggc    300
acagguaaaa cccuacuugc cagagcaugu gcugcacaga caaaaucaac auuuuaaaa    360
cuugcugggc cucaguuggu ccaaauguuu auuggugaug gugccaaauu ggugcgugau    420
gcuuuugcac ucgccaaaga aaaagcccu gcauuauu ucaugauga uuggaugcc        480
auggucacaa aacguuuuga uucugagaaa gcuggugauc gugaggguaca acguaccaug   540
uuagaguugc ugaaccaguu ggauggcuuc aguccacug cugauauuaa gguuauugcu     600
gcuacuaaua gaguggauau uuggauccu gcgcuuuuga gaucuggaag auuggauaga     660
aagauugagu ucccucaucc aaaugaagaa gcaagagcaa g                       701
```

<210> SEQ ID NO 21
<211> LENGTH: 720
<212> TYPE: RNA
<213> ORGANISM: Sitophilus oryzae

<400> SEQUENCE: 21

```
uaaaaccagg ugauuuugguc ggugugaaua aggauucaua ccuaauuuug gagacccuuc   60
cugcugaaua cgaugccaga guuaaagcua uggaggguga ugaaagacca acagaacaau   120
acucagauau ugguggcuug acaaacaaa uucaagagcu cauagaggcu guaguccucc   180
caaugacaca caaagauaaa uuugucaauu uaggaauaca accuccuaaa ggguauugu    240
uguauggacc uccaggaaca ggaaagacuc ugcuggcuag ggcuugugcu gcccaaacca   300
aaucaacuuu cuugaaauug gcagggcccc aguugguuca gauguuuauu ggugacggug   360
caaaacuagu uagagaugcu uuugcauugg ccaaagagaa agcaccugcu auuauuuuug   420
ucgaugaacu ggaugcaauu gguacuaaaa gauucgauuc ugaaaaggcu ggugaucggg   480
aaguacagag aacuauguug gaauuauuga aucaguuaga ugguuucagu ucgacagcag   540
auauuaaggu uauagcagca acuaaucugu uugacauucu cgauccagca uuguugcgau   600
ccggcagauu ggaucguaaa auugaauucc ucauccgaa ugaagaagcc agagcgagaa    660
uuaugcagau ucauucgaga aaaaugacag uaaacccuga cguaaacuuu gaggaauugg  720
```

<210> SEQ ID NO 22
<211> LENGTH: 742
<212> TYPE: RNA
<213> ORGANISM: Sitophilus granaries

<400> SEQUENCE: 22

```
agcugaauau gaugccagag uuaaagcuau ggagguugau gaaagaccaa cagaacagua   60
cucagacauu ggaggguugg auaaacaaau ucaagagcuc auagaggcug uaguccuccc  120
aaugacacau aaagauaaau uugucaauuu aggaauccaa ccuccuaaag ggguauugu   180
guauggaccu ccaggaacag gaaagacucu cuggcuagg gcaugugcug cccaaacaaa   240
aucaacauuc uugaaauuag cagggcccca auuaguucag auguuuaucg cgacggugc   300
aaaacuagug agggaugcuu uugcguuggc caaagagaaa guaccggcua uuauuuugu   360
```

| | |
|---|---|
| cgaugagcug gaugcaauug guacgaaaag auucgauucu gaaaaggcug gugauaggga | 420 |
| aguacaaaga acuauguuag aauuauugaa ucaguuagau gguucagu caacagcaga | 480 |
| uauuaagguu auagcagcaa ccaaucgugu ugauauucuc gauccagcau auugcgauc | 540 |
| ggguagguug gaucguaaaa uugaauuccc ccauccgaau gaagaagcca gagcgagaau | 600 |
| uaugcagauu cauucaagaa aaaugacggu aaacccugau guaaacuuug aagaauuggc | 660 |
| uagaucuacu gaugauuuua auggagcuca guguaaagcu guaugugugg aggcugguau | 720 |
| gauagcuuug agaagaaacg cu | 742 |

<210> SEQ ID NO 23
<211> LENGTH: 755
<212> TYPE: RNA
<213> ORGANISM: Ceuthorrhynchus assimilis

<400> SEQUENCE: 23

| | |
|---|---|
| cccugccuua uuuggugucg aaugugauug aacuuuugga gugggauccg caagaagagg | 60 |
| aagaagaugg agcuguuguu gauuuggauu cacaaagaaa aggaaagugu gcaguaguaa | 120 |
| aaacauccac ucgccaaacc uauuccuuuc cuguaauagg gcucguagau gaagaaaaau | 180 |
| ugaagccggg agauuggguu ggugucaaca agauucuuua ucuuauuuug gaaacuuugc | 240 |
| cagcugaauu ugaugccaga guaaaagcua uggagguuga ugaaagacca acagaacaau | 300 |
| acucagacau cgguggcuua gacaaacaaa uacaagaauu aaucgaagca guggauuugc | 360 |
| caaugacuca caaagacaag uuuguuaacu ugggcauuca accccaaaaa ggugcuuuau | 420 |
| uauaugggcc accagguacu ggaaaaaacac uacggcucg agcuugugcc gcucaaacca | 480 |
| aaucgacuuu ccugaaacug gcagguccuc aguuaguuca aauguuuauu ggcgacggug | 540 |
| cgaaauuagu cagagacgcu uuugcuuugg ccaaggaaaa aguuccagca auuauuuuua | 600 |
| ucgaugaauu ggacgcuauc gguacuaaac guucgauuc ugaaaaagcu ggagacaggg | 660 |
| aaguucaaag gaccauguug gaacuuuuga ucaguuaga cgguuucagu uccacagcgg | 720 |
| auauuaaagu aauugcagcc acaaaucgug uagac | 755 |

<210> SEQ ID NO 24
<211> LENGTH: 656
<212> TYPE: RNA
<213> ORGANISM: Rhyzopertha dominica

<400> SEQUENCE: 24

| | |
|---|---|
| acaaagaaag ggcaaaugug cuguagucaa gacguccacu cgucaaacuu acuuucugcc | 60 |
| aguuaucgga uuggucgaug aagagaaacu uaaaccgggu gaucucguug guguugaacaa | 120 |
| agauucuuau uuaauacugg aaacucuucc ugcugaguau gaugcuagag uuaaagcaau | 180 |
| ggaaguagac gaacggccua cggaacagua uucggauauu ggagguuugg auaagcaaau | 240 |
| acaagaguua auagaagcug uugacuccc uaugacacac aaagauaaau uccuuaaccu | 300 |
| ggguauucac ccaccgaagg guguccuucu guaugggcca ccuggaacag gaaaaacucu | 360 |
| gcuagcaaga gcaugugcug cacaaacaaa gucaacguuu uuaaagcugg cugggccaca | 420 |
| gcuggugcag auguucauag gugacggagc uaagcuugua agggaugcau uugcacuggc | 480 |
| uaaggagaag ucuccugcua ucauauuuau cgaugaacug gaugcuauag guacaaaacg | 540 |
| cuucgauucu gaaaaggcag gggaucguga agugcaacgu acgauguuag aacuacuuaa | 600 |
| ccaacuugac gguuuuucau cuacagcaga cauuaaagua auugcugcca ccaaua | 656 |

<210> SEQ ID NO 25
<211> LENGTH: 315
<212> TYPE: RNA
<213> ORGANISM: Phyllotreta nemorum

<400> SEQUENCE: 25

| uccaaagaac | cauguuggaa | cuguugaacc | aacuggacgg | uuucagcucc | acuuccgaca | 60 |
| ucaaagucau | agcagcuacg | aaucgugugg | auauucugga | ucccgcucug | cuucggucug | 120 |
| gucgguugga | caggaagauc | gaauucccgc | aucccaacga | agaggcgagg | gcagaaauca | 180 |
| ugcagauuca | cuccaggaaa | augacgguca | acccggacgu | gaacuucgag | gaauuggcua | 240 |
| gaucuacgga | cgacuucaac | ggggcucagu | guaaggcugu | gugcgucgaa | gcugguauga | 300 |
| ucgcucucag | acgua | | | | | 315 |

<210> SEQ ID NO 26
<211> LENGTH: 701
<212> TYPE: RNA
<213> ORGANISM: Psylliodes chrysocephala

<400> SEQUENCE: 26

| cuauggaggu | ggaugagaga | ccugcugaac | aguacucaga | uauuggaggu | uuagauaaac | 60 |
| aaauccaaga | acugauugaa | gcuguugugu | uaccaaugac | ccauaaagau | aaauuuguua | 120 |
| auuuggguau | ucauccccca | aaaggcguuu | uacuauacgg | gccaccugga | acuggaaaaa | 180 |
| cccuccuugc | cagagcaugu | gcagcucaaa | caaaaucaac | cuucuuaaaa | uuagcuggcc | 240 |
| cccaauuagu | ccagauguuu | auggugacg | gcgccaagcu | ugugagagau | gcauucgcuu | 300 |
| uagccaaaga | aaaaucuccc | gcuaucauau | uuaucgauga | acuggacgca | uaggcacaa | 360 |
| aaagauucga | uucugagaaa | gcgggugaca | gggaagugca | acguacuaug | uuggaguugc | 420 |
| ugaaccagcu | ggaugggguc | aguucaaccg | ccgauaucaa | agugauagcu | gcuaccaauc | 480 |
| gugucgauau | uuuagacccu | gcucugcuuc | gaucugguag | auuagacaga | aagauagaau | 540 |
| ucccgcaucc | caaugaagaa | gcgagggcua | gaaucaugca | gauucacucc | aggaaaauga | 600 |
| cgucaauccc | ugaugugaau | uuugaagaac | uggcuagguc | uacagaugac | uuuaauggag | 660 |
| cccagugcaa | ggcugugugu | guugaagcug | guaugauugc | u | | 701 |

<210> SEQ ID NO 27
<211> LENGTH: 720
<212> TYPE: RNA
<213> ORGANISM: Phyllotreta striolata

<400> SEQUENCE: 27

| ucgaggcugu | uguacuaccu | augacucaua | aagacaaguu | cguuaacuug | ggaauucauc | 60 |
| cucccaaagg | uguucuccuu | uacgguccc | cggguaccgg | uaaaacccuc | cuagccagag | 120 |
| ccugcgccgc | ccaaaccaaa | ucaacuuucc | ucaaacuggc | cgguccucag | uuaguccaga | 180 |
| uguucauagg | cgacggcgcc | aaguuaguc | gagacgccuu | cgccuuggcc | aaagagaagg | 240 |
| cacccgcuau | aauauucauc | gacgagcugg | acgccaucgg | uacgaagcga | uucgacucgg | 300 |
| agaaagccgg | agaccgggag | guccaacgaa | ccauguugga | acugcucaac | caacuggacg | 360 |
| gcuucagcuc | gacauccgac | aucaaaguca | uagcggcuac | gaaucgcgug | gauauucugg | 420 |
| auccccgcccu | gcugcgguc | ggaagguugg | accggaagau | cgaguucccg | caucccaacg | 480 |
| aagaggcgcg | agcgagaauc | augcagauuc | acuccagaaa | aaugacgguu | aacccggacg | 540 |
| ugaacuucga | ggaauuggcc | aggucuacug | augacuucaa | uggggcccag | uguaaggcug | 600 |

| | |
|---|---|
| ugugugucga agcuggaaug aucgcucuca gacguaacgc cacugcugug acucacgagg | 660 |
| acuacaugga ugcuauuaug gaaguucaag cuaagaaaaa ggcgaaucug aauuauuacg | 720 |

```
<210> SEQ ID NO 28
<211> LENGTH: 762
<212> TYPE: RNA
<213> ORGANISM: Diabrotica virgifera

<400> SEQUENCE: 28
```

| | |
|---|---|
| cuggacucac aaagaaaagg aaaaugugcu guuguuaaaa cuuccacuag acaaaccuac | 60 |
| uuuuuaccag ugauaggucu ggggaacgag gagaaguuaa agccagguga uuugguagga | 120 |
| guaaacaaag auucauaccu uauuuuggaa acauuaccug cugaauauga ugccagaguu | 180 |
| aaagcuaugg aaguagauga aagaccaacu gaacaguauu cagacauugg aggucuagau | 240 |
| aaacaaaucc aagaauuaau ugaagcuguu guuuuaccua ugacucacaa agauaaauuu | 300 |
| guuaauuugg guauacaucc accaaaaggu guguugguau auggucccc ugguacagga | 360 |
| aagacucuuu uggccagagc uugugcugca caaaccaaau caacauuuuu gaaauuggcu | 420 |
| gguccucaac ucguucaaau guucauugga gauggugcca aacugucag agaugcuuuu | 480 |
| gcucuugcca aagagaaggc accagcuaua auauucauug augaauuaga gcuaucggu | 540 |
| accaaaagau uugauucuga gaaagcugga gacagagaag uccagcguac uaguuagaa | 600 |
| cuucuuaacc aguggauugg auucaguuca acagcugaua uuaagguuau agcugcuacc | 660 |
| aaucguguag auauauugga uccugcucua cuccguucug guagauuaga ucguaaaaua | 720 |
| gaguucccuc accccaauga ggaagcgaga gcuagaauca ug | 762 |

```
<210> SEQ ID NO 29
<211> LENGTH: 1284
<212> TYPE: RNA
<213> ORGANISM: Meligethes aeneus

<400> SEQUENCE: 29
```

| | |
|---|---|
| augucucagc uugaagauaa gucgauaugg gaggauggg acgauacgcu gggcgaagaa | 60 |
| guccucagga uguccacuga ugaaauugua agccguacua ggcuuuugga uaacgaaaua | 120 |
| aaaauaauga aaagcgaggu uaugcguauc aaucaugaau ugcaagcuca aacagagaag | 180 |
| auuaaagaga auacgaaaaa gauuaaagug aauaaaacuc uuccuuacuu aguuucuaau | 240 |
| guaauagaau uguuagaugu agaucaacaa gaagaagaag aagaugggc uguaguugac | 300 |
| uuagauucuc aacguaaagg uaaaugcgcu guugucaaaa ccucuacacg ucaaacguac | 360 |
| uuuuugccug ucauugggu aguugaugag gaaaaauuga aaccaggcga ucuuguagga | 420 |
| guaaacaaag acucuuacuu aauucuugaa acucuuccug cagaauauga ugccagaguc | 480 |
| aaagcaaugg aaguagauga acgccccacu gaacaauauu cugauauugg ugguuuagac | 540 |
| aaacaaaucc aagaguuaau ugaagcugua guucuuccaa ugacacacaa agaaaaauuu | 600 |
| guaaaccucg gcauucaccc cccuaaagga guauuauuau auggucccc uggcacaggu | 660 |
| aaaaccuuac uugccagagc augugcugca cagacaaaau caacauuuuu aaaacuugcu | 720 |
| gggccucagu uguccaaaau guuuauuggu gauggugcca aauuggugcg ugaugcuuuu | 780 |
| gcacucgcca agaaaaagc cccugcuauu auuuucauug augaguugga ugccauuggu | 840 |
| acaaaacguu uugauucuga gaaagcuggu gaucgugagg acaacguac cauguuagag | 900 |
| uugcugaacc aguggauugg cuucaguucc acugcugaua uuaagguuau ugcugcuacu | 960 |
| aauagagugg auauuuugga uccugcgcuu uugagaucug gaagauugga uagaaagauu | 1020 |

| | |
|---|---|
| gaguucccuc auccaaauga agaagcaaga gcaagaauca ugcaaauuca cucaagaaaa | 1080 |
| augacuguaa acccagaugu gaacuuugaa gaauuggcca ggucuaccga ugacuuuaau | 1140 |
| ggggcccaau guaaggcagu guguguugaa gcugguauga uugcuuugag aagaagcgcc | 1200 |
| acagcuguca cccaugaaga uuacauggau gcuauuaugg aaguacaggc caagaagaag | 1260 |
| gccaacuuaa acuacuaugc uuaa | 1284 |

<210> SEQ ID NO 30
<211> LENGTH: 1284
<212> TYPE: RNA
<213> ORGANISM: Sitophilus oryzae

<400> SEQUENCE: 30

| | |
|---|---|
| auggcuacgc uagaagauaa ggcgauaugg gacgacggag aagaagcacu cggcgaagaa | 60 |
| guacugagaa ugucuaacga cgagauuaua agcagaacua gacuguugga caacgaaauu | 120 |
| aaaauaauga aaagcgaagu gaugagaaua aaccacgagc ugcaagccca aaacgaaaag | 180 |
| auuaaggaga acacggagaa aauuaaaguu aauaaaaccu uaccauauuu aguuucaaau | 240 |
| guuauugaau ugcucgaugu ggacccacaa gaagaggaag aggaugggc uguuguugau | 300 |
| uuagauucuc aaagaaaagg aaaaugugca guuguaaaaa caucaacacg ccaaaccuac | 360 |
| uuucuuccug uuaucggacu uguugaugaa gaaaaauuaa aaccagguga uuuggucggu | 420 |
| gugaauaagg auucauaccu aauuuuggag acccuuccug cugaauacga ugccagaguu | 480 |
| aaagcuaugg agguugauga agaccaaca gaacaauacu cagauauugg uggcuuggac | 540 |
| aaacaaauuc aagagcucau agaggcugua guccucccaa ugacacacaa agauaaauuu | 600 |
| gucaauuuag gaauacaacc uccuaaaggg guauuguugu auggaccucc aggaacagga | 660 |
| aagacucugc uggcuagggc uugugcugcc caaaccaaau caacuuucuu gaaauuggca | 720 |
| gggccccagu gguucagau guuuauuggu gacggugcaa aacuaguuag agaugcuuuu | 780 |
| gcauuggcca aagagaaagc accugcuauu auuuuugucg augaacugga ugcaauuggu | 840 |
| acuaaaagau ucgauucuga aaaggcuggu gaucgggaag uacagagaac uauguuggaa | 900 |
| uuauugaauc aguuagaugg uuucaguucg acagcagaua uuaagguuau agcagcaacu | 960 |
| aaucguguug acauucucga uccagcauug uugcgauccg gcagauugga ucguaaaauu | 1020 |
| gaauucccuc auccgaauga agaagccaga gcgagaauua ugcagauuca uucgagaaaa | 1080 |
| augacaguaa acccugacgu aaacuuugag gaauuggcua gaucaacgga ugauuuuaau | 1140 |
| ggagcccagu guaaagcugu augugugggag gcugguauga uagcuuugag aaggaacgcu | 1200 |
| acuguaguga cgcacgaaga cuacauggac gcuauaaugg aagugcaagc gaaaagaaaa | 1260 |
| gccaaucuua auuauuaugc uuaa | 1284 |

<210> SEQ ID NO 31
<211> LENGTH: 1284
<212> TYPE: RNA
<213> ORGANISM: Sitophilus granaries

<400> SEQUENCE: 31

| | |
|---|---|
| auggcuacgc uagaagacaa agcgauaugg gacgacggag aagaagcacu aggcgaagaa | 60 |
| guacugagaa ugucuaacga cgagauuaua agcagaacua gacuguugga caacgaaauu | 120 |
| aaaauuauga aaagcgaagu gaugagaaua aaccacgaau acaagcuca gaacgaaaag | 180 |
| auuaaggaaa acacggagaa aaucaaaguu aauaaaaccuu uaccguaucu aguuucaaau | 240 |

| | |
|---|---:|
| guuaucgaac uacuugaugu agauccacaa gaagaggaag aagauggagc uguuguggau | 300 |
| uuagauucuc aaagaaaagg aaaaugugca guuguaaaga caucaacgcg ccaaacauau | 360 |
| uuucuuccug uuauuggacu ugucgacgaa gaaaaauuga aaccugguga ucugguaggu | 420 |
| guuaacaagg acucuuaccu uauuuuggag acacugccag cugaauauga ugccagaguu | 480 |
| aaagcuaugg agguugauga agaccaaca gaacaguacu cagacauugg agguuuggau | 540 |
| aaacaaauuc aagagcucau agaggcugua guccucccaa ugacacauaa agauaaauuu | 600 |
| gucaauuuag gaauccaacc uccuaaaggg guauuguugu auggaccucc aggaacagga | 660 |
| aagacucuuc uggcuagggc augugcugcc caaacaaaau caacauucuu gaaauuagca | 720 |
| gggccccaau uaguucagau guuuaucggc gacggugcaa aacuagugag ggaugcuuuu | 780 |
| gcguuggcca agagaaagu accggcuauu auuuuugucg augagcugga ugcaauuggu | 840 |
| acgaaaagau ucgauucuga aaaggcuggu gauagggaag uacaagaac uauguuagaa | 900 |
| uuauugaauc aguuagaugg uuucaguuca acagcagaua uuaagguuau agcagcaacc | 960 |
| aaucguguug auauucucga uccagcauua uugcgaucgg guagguugga ucguaaaauu | 1020 |
| gaauucccc auccgaauga agaagccaga gcgagaauua ugcagauuca uucaagaaaa | 1080 |
| augacgguaa acccugaugu aaacuuugaa gaauuggcua gaucuacuga ugauuuuaau | 1140 |
| ggagcucagu guaaagcugu augugggag gcugguauga uagcuuugag aagaaacgcu | 1200 |
| accgcaguga cacacgagga cuacauggac gcuauaaugg aagugcaagc uaaaaagaaa | 1260 |
| gccaaucuua auuauuaugc uuaa | 1284 |

<210> SEQ ID NO 32
<211> LENGTH: 1284
<212> TYPE: RNA
<213> ORGANISM: Ceuthorrhynchus assimilis

<400> SEQUENCE: 32

| | |
|---|---:|
| augacuacau uagacgauaa aucuuugugg gaggacgguag aagaagcccu aggcgaagaa | 60 |
| guugcgaa uguccagcga ugaaauaguu agcagaacaa gacugaugga caaugaaauc | 120 |
| aaaauaauga aaagcgaggu gaugaggauu aaucacgaau ugcaagcgca aaacgagaag | 180 |
| auuaaagaaa acacugagaa aauaaaagua aacaaaaccc ugccuuauuu ggugucgaau | 240 |
| gugauugaac uuuggaugu ggauccgcaa gaagaggaag aagauggagc uguuguugau | 300 |
| uuggauucac aaagaaaagg aaagugugca guaguaaaaa cauccacucg ccaaaccuau | 360 |
| uuccuuccug uaauagggcu cguagaugaa gaaaaauuga agccgggaga uugguuggu | 420 |
| gucaacaaag auucuuaucu uauuuuggaa acuugccag cugaauauga ugccagagua | 480 |
| aaagcuaugg agguugauga agaccaaca gaacaauacu cagacaucgg uggcuuagac | 540 |
| aaacaaauac aagaauuaau cgaagcagug uauugccaa ugcucacaa agacaaguuu | 600 |
| guuaacuugg gcauucaacc uccaaaaggu guuuauuau augggccacc agguacugga | 660 |
| aaaacacuac uggcucgagc uugugccgcu caaaccaaau cgacuuccu gaaacuggca | 720 |
| gguccucagu uaguucaaau guuuauuggc gacggugcga auuagucag agacgcuuuu | 780 |
| gcuuuggcca aggaaaaagu uccagcaauu auuuuuaucg augaauugga cgcuaucggu | 840 |
| acuaaacguu ucgauucuga aaaagcugga gacagggaag uucaaggac caugguugaa | 900 |
| cuuuugaauc aguuagacgg uuucaguucc acagcggaua uuaaaguaau ugcagccaca | 960 |
| aaucguguag acauuuugga uccgcccug uuaagaucgg gacguuugga ucguaaaauc | 1020 |
| gaauuuccac auccaaauga ggaggccaga gcuaggauua ugcaaauuca uucaaggaaa | 1080 |

| | |
|---|---|
| augacuguua auccugaugu uaauuuugaa gaauuggcua ggaguacuga ugacuucaau | 1140 |
| ggagcccaau guaaagcugu cugcguugaa gcugguauga ucgcucugag aaggaaugcu | 1200 |
| acagcaguga cucacgaaga uuauauggau gcuaucaugg agguacaggc uaagaagaag | 1260 |
| gcuaaccuca auuacuaugc uuaa | 1284 |

<210> SEQ ID NO 33
<211> LENGTH: 1281
<212> TYPE: RNA
<213> ORGANISM: Rhyzopertha dominica

<400> SEQUENCE: 33

| | |
|---|---|
| augucgacuc uggaagaugc aucaauuugg gaugaaggag aaucccuugg ugaagacguu | 60 |
| cuucguaugu cuacggauga aauaguaagu cgcacccggc uucuagacaa ugagauuaag | 120 |
| aucaugaaaa gugaagucau gcguauuaau caugaacucc aagcacaaaa cgaaaagaua | 180 |
| aaagagaaca cagagaagau uaaaguuaac aagaccuuac ccuaucuagu uucaaauguu | 240 |
| aucgaacugu uggauguaga uccccaggaa gaagaagaag acggagcugu uguugauuua | 300 |
| gacgcacaaa gaaagggcaa augugcuaua gucaagacgu ccacucguca aacuuacuuu | 360 |
| cugccaguua ucggauuggu cgaugaagag aaacuuaaac cgggugaucu cguugugug | 420 |
| aacaaagauu cuuauuuaau acuggaaacu cuuccugcug aguaugaugc uagaguuaaa | 480 |
| gcaauggaag uagacgaacg gccuacggaa caguauucgg auauuggagg uuuggauaag | 540 |
| caaauacaag aguuaauaga agcguuugua cuuccauga cacacaaaga uaaauuucuu | 600 |
| aaccugggua uucaccccacc gaaggguguc cuucuguaug ggccaccugg aacaggaaaa | 660 |
| acucugcuag caagagcaug ugcugcacaa acaaagucaa cguuuuuaaa gcuggcuggg | 720 |
| ccacagcugg ugcagauguu cauaggugac ggagcuaagc uuguaaggga ugcauuugca | 780 |
| cuggcuaagg agaagucucc ugcuaucaua uuuaucgaug aacuggaugc uauagguaca | 840 |
| aaacgcuucg auucugaaaa ggcaggggau cgugaagugc aacguacgau guuagaacua | 900 |
| cuuaaccaac uugacgguuu ucaucuaca cagacauua aaguaauugc ugccaccaau | 960 |
| agagucgaca ucuuagaucc ugcccugcua cguucuggc guuagauag aaagauugag | 1020 |
| uuuccacauc ccaaugagga agcaagggcc agaauuaugc agauacauuc acgaaaaaug | 1080 |
| acagugaauc ccgauguuaa uuuugaagaa cuggcaaggu caacgacga uuucaauggu | 1140 |
| gcccaaugua aagcuguguig uguugaggcg ggaaugauug ccuugagaag gaaugcuacu | 1200 |
| gcaguaacac augaagauua cauggaugca auaauggagg uucaggcuaa aaagaaggcc | 1260 |
| aaucuuaauu auuaugcuua g | 1281 |

<210> SEQ ID NO 34
<211> LENGTH: 504
<212> TYPE: RNA
<213> ORGANISM: Phyllotreta nemorum

<400> SEQUENCE: 34

| | |
|---|---|
| gccuuggcca aagagaaagc cccugcuaua auauucaucg acgaauugga cgccaucggu | 60 |
| acgaagcgau ucgacuccga gaaagccggc gacaggaag uccaaagaac cauguuggaa | 120 |
| cuguugaacc aacuggacgg uuucagcucc acuuccgaca ucaaagucau agcagcuacg | 180 |
| aaucgugugg auauucugga ucccgcucug cuucggucug gucgguugga caggaagauc | 240 |
| gaauucccgc aucccaacga agaggcgagg gcgagaauca ugcagauuca cuccaggaaa | 300 |

```
augacgguca acccggacgu gaacuucgag gaauuggcua gaucuacgga cgacuucaac    360
ggggcucagu guaaggcugu gugcgucgaa gcugguauga ucgcucucag acguaacgcc    420
acugcgguaa cgcacgagga cuacauggau gcuauuaugg aaguucaagc uaagaaaaag    480
gcuaaucuua auuauuacgc cuaa                                           504
```

```
<210> SEQ ID NO 35
<211> LENGTH: 1284
<212> TYPE: RNA
<213> ORGANISM: Psylliodes chrysocephala

<400> SEQUENCE: 35
```

```
augucgacuu uagaagauaa aucgaucugg gaagacggcg aagaagcgcu aggugaagaa     60
guucucagaa ugucuaccga ugaaauaguu agucguacuc guuuauugga caaugagauc    120
aaaauaauga agagugaagu aaugagaaua aaucacgaau acaagcaca gaaugagaag     180 aucaaagaga acacgaaaaa aauaaaagua aacaaaacgu ugccuuauuu ggugucuaac    240
gugauagaac uguuagaugu cgaucccag gaagaggaag aagacggugc aguggugaau    300
uuggauucuc aaagaaaagg aaaaugugca guaguuaaaa caucaacccg ccaaacuuac    360
uuucugccag uuuaugggcu gguugaugag gaaaaguuga agccuggugu uuuaguuggu    420
gucaacaaag acucuuaucu cauuuuggaa acgcugccug ccgaguacga ugccagaguu    480
aaagcuaugg agguggauga gagaccugcu gaacaguacu cagauauugg agguuuagau    540
aaacaaauuc aagaacugau ugaagcuguu guuuaccaa ugacccauaa agauaaauuu    600
guuaauuugg guauucaucc cccaaaaggc guuuuacuau acgggccacc uggaacugga    660
aaaccccuuc uugccagagc augugcagcu caaacaaaau caaccuucuu aaaauuagcu    720 ggccccccaau uagcccagau guuuauuggu gacggcgcca agcuugugag agaugcauuc    780
gcuuuagcca agaaaaaauc ucccgcuauc auauuuaucg augaacugga cgcaauaggc    840
acaaaaagau ucgauucuga gaaagcgggu gacagggaag ugcaacguac uauguuggag    900
uugcugaacc agcuggaugg guucaguuca accgccgaua ucaagugau agcugcuacc    960 aaucgugucg auauuuuaga cccugcucug cuucgaucug uagauuaga cagaaagaua    1020 gaauucccgc aucccaauga agaagcgagg gcuagaauca ugcagauuca cuccaggaaa    1080
augacuguca auccugaugu gaauuuugaa gaacuggcua ggcuacaga ugacuuuaau    1140 ggagcccagu gcaaggcugu gugugauuaa gcugguauga uugcuuugag acguaacgcu    1200
aaugccguca cacaugaaga uuauauggau gcuauaaugg aagugcaagc caagaagaag    1260
gcaaaucuua auuacuaugc uuag                                           1284
```

```
<210> SEQ ID NO 36
<211> LENGTH: 1284
<212> TYPE: RNA
<213> ORGANISM: Phyllotreta striolata

<400> SEQUENCE: 36
```

```
augucgaccu uagaagacaa aucgauuugg gaagacggcg aggaagcgcu cggcgaggaa     60
guuuuaagaa ugucacacuga cguuaucaua ggucauacgc gauugcugga caaugagauc    120
aaaauaauga agagcgaagu gaugcgaauaa aaccacgaac ugcaagcgca aaacgagaaa    180
aucaaagaaa acaccgagaa gauaaaagug aacaaaaccu ugccuuacuu ggucucgaac    240
guaauugaac cuuggacgu agaucccag gaagaggaag aggacggugc uuaguucgau    300
uuggauucuc agagaaaagg gaaaugcgcu guaguaaaaa cguccacgag acagaccuau    360
```

-continued

```
uuccuacccg ugauagggcu ggucgaugag gagaaacuga aaccgggaga ucuaguggga      420
gucaacaaag acucguaucu aauucuggaa acauuaccug cagaguacga ugcgagaguc      480
aaggccaugg aagucgacga aaggccuucu gaacaguauu ccgauaucgg agguuuagau      540
aagcaaauac aagaacuuau cgaggcuguu guacuaccua ugacacauaa agacaaguuc      600
guuaacuugg gaauucaucc ucccaaaggu guucuccuuu acggucccccc ggguaccggu      660 aaacccuccc uagccagagc cugcgccgcc caaaccaaau caacuuuccu caaacuggcc      720
gguccucagu uaguccagau guucauaggc gacggcgcca aguuaguccg agacgccuuc      780
gccuuggcca aagagaaggc acccgcuaua auauucaucg acgagcugga cgccaucggu      840
acgaagcgau ucgacucgga gaaagccgga gaccgggagg uccaacgaac caugguggaa      900
cugcucaacc aacuggacgg cuucagcucg acauccgaca ucaaagucau agcggcuacg      960
aaucgcgugg auauucugga ucccgcccug cugcgguccg gaagguugga ccggaagauc     1020
gaguucccgc aucccaacga gaggcgcga gcgagaauca ugcagauuca ucccagaaaa     1080
augacgguua acccggacgu gaacuucgag gaauuggcca ggucuacuga ugacuucaau     1140
ggggcccagu guaaggcugu gugugucgaa gcuggaauga ucgcucucag acguaacgcc     1200
acugcuguga cucacgagga cuacauggau gcuauaugg aaguucaagc uaagaaaaag     1260
gcgaaucuga auuauuacgc cuaa                                           1284
```

<210> SEQ ID NO 37
<211> LENGTH: 1284
<212> TYPE: RNA
<213> ORGANISM: Diabrotica virgifera

<400> SEQUENCE: 37

```
auggcuacuc uugaagaugu uucuauuugg gaagauggag aggaagcauu aggugaagag       60
guuuuacgaa uguccacuga ugaaauaguu agccggacac guuuacuaga caaugaaauu      120
aaaauaauga agagugaagu augagaauc aaucaugaau uacaagccca aaaugagaaa      180
auaaaggaga auacgagaa auuuaaagug aacaaaaccu uaccguacuu ggugugccaau      240 guaauagaac uguuagaugu ggaucccccaa gaggaagagg aagaugguugc aguuguugau      300 cuggacucac aaagaaaagg aaaaugugcu guuguuaaaa cuuccacuag acaaaccuac      360
uuuuuaccag ugauagugcu ggggacgag gagaaguuaa agccaggugga uuuggauagga      420 guaaacaaag auucauaccu uauuuuggaa acauuaccug cugaauauga ugccagaguu      480
aaagcuaugg aaguagauga aagaccaacu gaacaguauu cagacauugg aggucuagau      540
aaacaaauuc aagaauuaau ugaagcuguu guuuuaccua ugacucacaa agauaaauuu      600
guuaauuugg guauacaucc accaaaaggu guguugguau augguccccc ugguacagga      660
aagacucuuu uggccagagc uugugcugca caaaccaaau caacauuuuu gaaauuggcu      720
gguccucaac ucguucaaau guucauugga gauggugcca aacuugucag agaugcuuuu      780
gcucuugcca aagagaaggc accagcuaua auauucauug augaauuaga ugcuaucggu      840
accaaaagau uugauucuga gaagcuggaa cagagaaag uccagcguac uauguuagaa      900
cuucuuaacc aguggauggu auucaguuca acagcugaua uuaagguuau agcugcuacc      960
aaucguguag auauauuggga uccugcucua cucccguucu guagauuaga ucguaaaaua     1020 gagucccuc accccaauga ggaagcgaga gcuagaauca ugcaaauuca uucaagaaaa     1080
augacaguca auccugaugu caacuuugag gaauuagcaa gaucaacaga ugacuucaau     1140
```

-continued

```
ggagcucaau guaaagcagu cuguguugag gcagguauga uagcccuaag aaggagugcu    1200
acagcuguaa ucaugaaga uuauauggau gcaauuaugg agguucaagc uaagaagaag    1260
gcaaaucuua auuauuaugc uuaa                                          1284
```

<210> SEQ ID NO 38
<211> LENGTH: 20
<212> TYPE: DNA
<213> ORGANISM: Meligethes aeneus

<400> SEQUENCE: 38
acgtactttt tgcctgtcat                                               20

<210> SEQ ID NO 39
<211> LENGTH: 20
<212> TYPE: DNA
<213> ORGANISM: Meligethes auneus

<400> SEQUENCE: 39
cttgctcttg cttcttcatt                                               20

<210> SEQ ID NO 40
<211> LENGTH: 20
<212> TYPE: DNA
<213> ORGANISM: Sitophilus oryzae

<400> SEQUENCE: 40
taaaaccagg tgatttggtc                                               20

<210> SEQ ID NO 41
<211> LENGTH: 20
<212> TYPE: DNA
<213> ORGANISM: Sitophilus oryzae

<400> SEQUENCE: 41
ccaattcctc aaagtttacg                                               20

<210> SEQ ID NO 42
<211> LENGTH: 20
<212> TYPE: DNA
<213> ORGANISM: Sitophilus granarius

<400> SEQUENCE: 42
agctgaatat gatgccagag                                               20

<210> SEQ ID NO 43
<211> LENGTH: 20
<212> TYPE: DNA
<213> ORGANISM: Sitophilus granaries

<400> SEQUENCE: 43
agcgtttctt ctcaaagcta                                               20

<210> SEQ ID NO 44
<211> LENGTH: 20
<212> TYPE: DNA
<213> ORGANISM: Ceuthorrhynchus assimilis

<400> SEQUENCE: 44
ccctgcctta tttggtgtcg                                               20

<210> SEQ ID NO 45
<211> LENGTH: 22

```
<212> TYPE: DNA
<213> ORGANISM: Ceuthorrhynchus assimilis

<400> SEQUENCE: 45
gtctacacga tttgtggctg ca                                              22

<210> SEQ ID NO 46
<211> LENGTH: 20
<212> TYPE: DNA
<213> ORGANISM: Rhyzoperta dominica

<400> SEQUENCE: 46
acaaagaaag ggcaaatgtg                                                 20

<210> SEQ ID NO 47
<211> LENGTH: 20
<212> TYPE: DNA
<213> ORGANISM: Rhyzoperta dominica

<400> SEQUENCE: 47
tattggtggc agcaattact                                                 20

<210> SEQ ID NO 48
<211> LENGTH: 20
<212> TYPE: DNA
<213> ORGANISM: Phyllotreta nemorum

<400> SEQUENCE: 48
tccaaagaac catgttggaa                                                 20

<210> SEQ ID NO 49
<211> LENGTH: 20
<212> TYPE: DNA
<213> ORGANISM: Phyllotreta nemorum

<400> SEQUENCE: 49
tacgtctgag agcgatcata                                                 20

<210> SEQ ID NO 50
<211> LENGTH: 20
<212> TYPE: DNA
<213> ORGANISM: Psylliodes chrysocephala

<400> SEQUENCE: 50
ctatggaggt ggatgagaga                                                 20

<210> SEQ ID NO 51
<211> LENGTH: 20
<212> TYPE: DNA
<213> ORGANISM: Psylliodes chrysocephala

<400> SEQUENCE: 51
agcaatcata ccagcttcaa                                                 20

<210> SEQ ID NO 52
<211> LENGTH: 20
<212> TYPE: DNA
<213> ORGANISM: Phyllotreta striolata

<400> SEQUENCE: 52
tcgaggctgt tgtactacct                                                 20

<210> SEQ ID NO 53
```

```
<211> LENGTH: 20
<212> TYPE: DNA
<213> ORGANISM: Phyllotreta striolata

<400> SEQUENCE: 53
cgtaataatt cagattcgcc                                              20

<210> SEQ ID NO 54
<211> LENGTH: 20
<212> TYPE: DNA
<213> ORGANISM: Diabrotica virgifera

<400> SEQUENCE: 54
ctggactcac aaagaaaagg                                              20

<210> SEQ ID NO 55
<211> LENGTH: 20
<212> TYPE: DNA
<213> ORGANISM: Diabrotica virgifera

<400> SEQUENCE: 55
catgattcta gctctcgctt                                              20
```

CONTROL OF PLANT PESTS USING RNA MOLECULES

RELATED APPLICATION INFORMATION

This application is a 371 of International Application No. PCT/US2018/059380, filed Nov. 6, 2018, which claims priority to GB Application No. 1719680.9, filed Nov. 27, 2017, the contents of each of which are incorporated herein by reference herein.

SEQUENCE LISTING

A Sequence Listing in ASCII text format, submitted under 37 C.F.R. § 1.821, entitled "81495-WO-REG-ORG-P-1_ST25.txt," 52 kilobytes in size, generated on Oct. 18, 2018 and filed via EFS-Web is provided in lieu of a paper copy. This Sequence Listing is hereby incorporated by reference into the specification for its disclosures in its entirety.

FIELD OF THE INVENTION

The invention relates generally to the control of pests that cause damage to crop plants by their feeding activities, and more particularly to the control of at least coleopteran insect pests by compositions comprising interfering RNA molecules. The invention further relates to the compositions and to methods of using such compositions comprising the interfering RNA molecules.

BACKGROUND

Commercial crops are often attacked by invertebrate pests such as insects. Compositions for controlling insect infestations in plants have typically been in the form of chemical insecticides. Good insect control can thus be reached, but these chemicals can sometimes also affect other, beneficial insects. Additional problems occur in areas of high insecticide use where populations of pest insects have become resistant to certain insecticides. This has been partially alleviated by various resistance management practices, but there is an increasing need for alternative pest control agents.

Insecticidal compositions that include the bacteria *Bacillus thuringiensis* ("*Bt*") have been commercially available and used as environmentally safe and acceptable bio-insecticides for more than thirty years. The effectiveness of these compositions is due to insecticidal proteins (called "Cry proteins") that are produced during the sporulation phase of the bacteria's growth cycle. Cry proteins are primarily active against the larval stages of pest insects and not active against the adult stage. Several native Cry proteins from *Bt*, for example, Cry1 Ab, Cry1F, Cry2Aa and Cry34/Cry35, or engineered Cry proteins, for example modified Cry3A (mCry3A) or eCry3.1Ab, have also been expressed in transgenic crop plants, for example corn, and exploited commercially to control certain lepidopteran and coleopteran insect pests.

With the increased use of transgenic plants expressing Cry proteins, there have now been some reports that populations of pest insects in certain geographies have become tolerant or resistant to certain Cry proteins. Therefore, identifying alternative insect control agents with new modes of action, i.e. different from existing chemical insecticides and Cry proteins, would be beneficial. In addition, new biological insect control agents that may be toxic to multiple life stages of the target insect pest would be useful. Such insect control agents may include those that target genetic elements, such as genes that are essential to the growth and/or survival of a target insect pest.

RNA interference (RNAi) is a well-established technique to regulate gene expression, for example to down regulate gene expression, by using double-stranded RNA (dsRNA) or small interfering RNA (siRNA) to trigger degradation of messenger RNA (mRNA) of a gene of interest, thus preventing translation of a protein. RNAi has not only provided a means of functionally analyzing genes, but has been used for the effective control of pests, in particular plant insect pests. RNAi occurs when an organism recognizes dsRNA molecules and hydrolyzes them. The resulting hydrolysis products are siRNA fragments of about 19-24 nucleotides in length. The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Most plant microRNAs (miRNAs) show extensive base pairing to, and guide cleavage of, their target mRNAs (Jones-Rhoades et al. (2006) *Annu. Rev. Plant Biol.* 57, 19-53; Llave et al. (2002) *Proc. Natl. Acad. Sci. USA* 97, 13401-13406). In other instances, interfering RNAs may bind to target RNA molecules having imperfect complementarity, causing translational repression without mRNA degradation. The majority of the animal miRNAs studied so far appear to function in this manner.

RNAi has been found to be useful for control of certain insect pests. RNAi strategies typically employ a synthesized, non-naturally occurring "interfering RNA", or "interfering RNA molecule" which typically comprises at least a RNA fragment against a target gene, a spacer sequence, and a second RNA fragment which is complementary to the first, so that a dsRNA structure can be formed. This non-naturally occurring dsRNA takes advantage of the native RNAi pathways in the insect to trigger down-regulation of target genes that may lead to the cessation of feeding and/or growth and may result in the death of the insect pest.

Although it is known in the literature that RNAi strategies focused on certain target genes can lead to an insecticidal effect, for example in *Diabrotica* (corn rootworm) species, it is also known that not every target sequence is successful, and that an insecticidal effect cannot be predicted. For example, the overwhelming majority of sequences complementary to corn rootworm DNAs are not lethal in species of corn rootworm when used as dsRNA or siRNA. For example, Baum et al. ((2007) Nature Biotechnology 25:1322-1326), describe the effects of inhibiting several western corn rootworm (WCR) gene targets by RNAi. These authors reported that 8 of 26 target genes they tested were not able to provide experimentally significant WCR mortality, even at a very high concentration of more than 520 ng/cm$^2$ of interfering RNA (e.g. dsRNA). Additionally, target genes against which a dsRNA molecule is known to give a strong RNAi effect in one insect species may not be a good target for different insect species. Whyard et al. ((2009) *Insect Biochemistry and Molecular Biology* 39: 824-832) report nearly 100-fold differences in efficacy when testing conspecific dsRNA molecules against a V-ATPase gene in four different insect species.

There is an ongoing need for compositions containing insecticidal active ingredients, and for methods of using such compositions, for instance for use in crop protection or insect-mediated disease control. Novel compositions are required to overcome the problem of resistance to existing insecticides and/or to help mitigate the development of resistance to existing transgenic plant approaches. Ideally such compositions have a high toxicity and are effective when ingested orally by the target pest and have applicability for use against the larval and/or adult stages of the pest insect. Thus any invention which provided compositions in which any of these properties was enhanced would represent a step forward in the art.

SUMMARY

The needs outlined above are met by the present invention which, in various embodiments, provides new compositions and methods of controlling economically important insect pests. More particularly, the invention provides compositions and methods of inhibiting expression of one or more target genes and proteins in at least coleopteran pests. More particularly, the invention provides compositions and methods of modulating expression of an Rpt5 target gene in coleopteran insect pests, such as *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata, Diabrotica undecimpunctata howardi, Diabrotica barberi* and *Diabrotica virgifera* and related species, that causes cessation of feeding, growth, development and reproduction, and eventually results in the death of the insect. A method of the invention comprises introduction of an interfering RNA molecule comprising a double-stranded RNA (dsRNA) or its modified forms such as small interfering RNA (siRNA) sequences, into cells or into the extracellular environment, such as the midgut, within a pest insect body wherein the dsRNA or siRNA enters the cells and inhibits expression of at least one or more target genes and wherein inhibition of the one or more target genes exerts a deleterious effect upon the pest insect. The interfering RNA molecule is non-naturally occurring. It is specifically contemplated that the methods and compositions of the invention will be useful in limiting or eliminating pest insect infestation in or on any plant by providing one or more compositions comprising interfering RNA molecules comprising dsRNA or siRNA molecules in the diet of the pest. The invention also provides interfering RNA molecules that, when delivered to a pest insect, inhibits through a toxic effect the ability of the pest insect to survive, grow, feed and/or reproduce, or to limit pest related feeding damage or loss to crop plants. Such delivery may be by topically applying a composition comprising the interfering RNA to a plant, or to a plant part, such as a plant seed or a plant root. Such delivery may also be through production of the interfering RNA in a transgenic plant. The interfering RNA may also be provided in an artificial insect diet which the insect then contacts by feeding. The interfering RNA molecule comprises a nucleotide sequence that is complementary to a nucleotide sequence of a mRNA transcribable from a target gene or a portion of a nucleotide sequence of a mRNA transcribable from a target gene of the pest insect and therefore inhibits expression of the target gene, which causes cessation of feeding, growth, development, reproduction and eventually results in death of the pest insect. The invention is further drawn to nucleic acid constructs, nucleic acid molecules and recombinant vectors that comprise or encode at least a fragment of one strand of an interfering RNA molecule of the invention. The invention also provides chimeric nucleic acid molecules comprising an antisense strand of a dsRNA of the interfering RNA operably associated with a plant microRNA precursor molecule. The invention also provides artificial plant microRNA precursors comprising an antisense strand of a dsRNA of an interfering RNA of the invention.

Accordingly, nucleic acid molecules comprising the sequence of Rpt5 from multiple insect pest species are disclosed herein as SEQ ID NO:1, SEQ ID NO:2, SEQ ID NO:3, SEQ ID NO:4, SEQ ID NO:5, SEQ ID NO:6, SEQ ID NO:7, SEQ ID NO:8 or SEQ ID NO:9. In addition, nucleic acid molecules comprising the complement of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9 are disclosed. Specific fragments of these sequences are also disclosed herein as SEQ ID NO:11, SEQ ID NO:12, SEQ ID NO:13, SEQ ID NO:14, SEQ ID NO:15, SEQ ID NO:16, SEQ ID NO:17, SEQ ID NO:18 or SEQ ID NO:19. The sequences of Rpt5 and/or a fragment thereof can be targeted by an interfering RNA of the invention which may cause cessation of feeding, growth, development and/or reproduction of a pest insect, and eventually results in the death of the pest insect.

In one aspect of the invention, an interfering RNA molecule is provided wherein the interfering RNA is encoded by a sequence comprising, consisting essentially of or consisting of (a) any one of SEQ ID NOs:1-9; (b) the complement of any one of SEQ ID NOs:1-9; (c) at least 19 consecutive nucleotides of any one of SEQ ID NOs:1-9; (d) the complement of at least 19 consecutive nucleotides of any one of SEQ ID NOs:1-9; or (e) a sequence that hybridizes under stringent conditions with any of the aforementioned sequences, wherein the interfering RNA molecule post-transcriptionally silences an essential gene in at least a coleopteran pest insect and wherein the RNA encoding sequence is not a sequence comprising SEQ ID NO:10, the complement of SEQ ID NO:10, any at least 19 nucleotide fragment of SEQ ID NO:10, the complement of any at least 19 nucleotide fragment of SEQ ID NO:10 or a sequence that hybridizes under stringent conditions with SEQ ID NO:10, or the complement or a fragment thereof.

In another aspect, the invention provides a double-stranded RNA (dsRNA) comprising annealed complementary strands, one strand of which comprises a sequence of at least 19 consecutive nucleotides which is wholly or partially complementary to a portion of a mRNA polynucleotide transcribable from a pest insect target gene, wherein the pest insect target gene comprises a coding sequence having from at least 90% to at least 99% identity to any of SEQ ID NOs:1-9, or comprises any of SEQID NOs:1-9, and wherein the strand of RNA having complementarity to the target gene is toxic to an insect pest, preferably to at least a coleopteran insect pest.

In another aspect of the invention, the inferring RNA or dsRNA is complementary to a portion of a target gene comprising, consisting essentially of or consisting of any of SEQ ID NOs:11-19.

In still another aspect of the invention, the inferring RNA or dsRNA comprises a nucleotide fragment that has at least 85% identity to any of SEQ ID NOs:20-37. In some embodiments of this aspect the inferring RNA or dsRNA comprises, consists essentially of or consists of any of SEQ ID NOs: 20-37.

In another aspect of the invention, the interfering RNA molecule has insecticidal activity on at least a coleopteran insect pest. In some embodiments of this aspect, the interfering RNA molecule may comprise, consist essentially of or consist of at least two dsRNAs, wherein each dsRNA comprises, consists essentially of or consists of a sequence of nucleotides which is at least partially complementary to a target nucleotide sequence within the target gene. In further embodiments, each of the dsRNAs may comprise a different sequence of nucleotides which is complementary to a different target nucleotide sequence within the target gene.

The invention further provides compositions comprising one or more interfering RNA molecules comprising, consisting essentially of or consisting of two or more dsRNA molecules, wherein the two or more RNA molecules each comprise a different antisense strand, or comprising two or more nucleic acid constructs or nucleic acid molecules or artificial plant microRNA precursors of the invention.

The invention further provides insecticidal compositions for inhibiting the expression of at least a coleopteran pest insect gene that comprises a dsRNA of the invention and an agriculturally acceptable carrier. In some embodiments of this aspect, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera*. In some embodiments, inhibition of the expression of an Rpt5 target gene in a target insect pest of the invention leads to cessation of feeding and growth and ultimately results in the death of the target insect pest of the invention.

The invention is further drawn to transgenic plants which produce one or more interfering RNA molecules of the invention that are self-protected from insect feeding damage and to methods of using the plants alone or in combination with other insect control strategies to confer maximal insect control capabilities. Plants and/or plant parts producing one or more interfering RNA molecules of the invention or treated with a composition comprising one or more interfering RNA molecules of the invention are highly resistant to insect pest infestation. For example, economically important coleopteran pests can be controlled by a plant that produces an interfering RNA molecule of the invention or by a plant or plant seed that is treated with a composition comprising an interfering RNA molecule of the invention.

The invention also provides a method of controlling at least a coleopteran insect pest comprising contacting the insect pest with a nucleic acid molecule that is or is capable of producing an interfering RNA of the invention for inhibiting expression of a target gene in the insect pest thereby controlling the insect pest. In some aspects, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera*. In other aspects, the target gene is Rpt5.

In other aspects, the invention provides a method of reducing an insect pest population on a transgenic plant expressing a second insecticidal agent, for example an insecticidal protein, by applying to the transgenic plant a composition comprising an interfering RNA of the invention capable of inhibiting expression of an target gene in an insect pest, thereby reducing the pest insect population. The second insecticidal agent may be an insecticidal protein derived from *Bacillus thuringiensis*. A *B. thuringiensis* insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417,a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the second insecticidal agent may be derived from sources other than B. thuringiensis. The second insecticidal agent can be an agent selected from the group comprising a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphearicus* insecticidal protein, a *Chromobacterium* spp. insecticidal protein, a *Yersinia entomophaga* insecticidal protein, a *Paenibacillus popiliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia,* or *Yersinia*. In other embodiments, the insecticidal protein may be an ADP-ribosyltransferase derived from an insecticidal bacteria, such as Photorhabdus spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In other aspects, the invention provides a method of reducing resistance development in a pest insect population to an interfering RNA of the invention, the method comprising expressing in a transgenic plant fed upon by the pest insect population an interfering RNA of the invention that is capable of inhibiting expression of a target gene in a larval and adult insect pest, thereby reducing resistance development in the pest insect population compared to a pest insect population exposed to an interfering RNA capable of inhibiting expression of a pest insect gene described herein in only the larval stage or adult stage of an insect pest.

In other aspects, the invention provides a method of reducing the level of a target RNA transcribable from a pest insect Rpt5 target gene described herein comprising contacting the pest insect with a composition comprising an interfering RNA molecule of the invention, wherein the interfering RNA molecule reduces the level of the target RNA in a cell of the pest insect.

In still other aspects, the invention provides a method of conferring pest insect, particularly at least a coleopteran pest insect tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, thereby conferring to the plant or part thereof tolerance to the pest insect.

In further aspects, the invention provides a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, thereby reducing root damage to the plant fed upon by a *Diabrotica* insect.

In other aspects, the invention provides a method of producing a transgenic plant cell having toxicity to at least a coleopteran pest insect, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the coleopteran insect compared to a control plant cell.

In further aspects, the invention provides a method of producing a transgenic plant having enhanced tolerance to at least coleopteran pest insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to at least a coleopteran pest insect feeding damage compared to a control plant.

In other aspects, the invention provides a method of enhancing control of at least a coleopteran insect population comprising applying to a plant or seed, or to a transgenic plant or a transgenic seed, a composition comprising an interfering RNA of the invention and a chemical pesticide that is insecticidal to at least a coleopteran insect, thereby enhancing control of the coleopteran insect population.

In another aspect, the invention provides a method of identifying a Rpt5 gene in an insect pest for interfering RNA targeting, said method comprising the steps of: a) isolating nucleic acid from an insect pest; b) amplifying an orthologous Rpt5 target gene from the nucleic acid with a pair of primers comprising nucleotide sequences selected from SEQ ID NOs:38-55; c) identifying a sequence of an orthologous Rpt5 target gene; d) producing a dsRNA molecule, wherein the dsRNA molecule comprises a sense strand and an antisense strand, wherein a nucleotide sequence of the antisense strand is complementary to a portion of a mRNA polynucleotide transcribable from the insect pest Rpt5 gene that comprises a Rpt5 coding sequence, and e) testing the dsRNA molecule of step d) for insecticidal activity against the insect pest.

These and other aspects of the invention are set forth in more detail in the description of the invention below.

BRIEF DESCRIPTION OF THE SEQUENCES IN THE SEQUENCE LISTING

SEQ ID NOs:1-10 are pest insect Rpt5 coding sequences.
SEQ ID NOs:11-19 are fragments of DNA coding sequences used to synthesize interfering RNA molecules to test for insecticidal activity.
SEQ ID NOs:20-28 are RNA sequences of the fragments of the DNA coding sequences used to synthesize interfering RNA molecules to test for insecticidal activity
SEQ ID NOs:29-37 are RNA sequences of the complete DNA sequences of SEQ ID NOs:1-9.

SEQ ID NOs:38-55 are nucleotide sequences of forward and reverse primers used to identify target genes (SEQ ID NOs:1-9) from pest insects of the invention.

DETAILED DESCRIPTION

The following is a detailed description of the invention provided to aid those skilled in the art in practicing the invention. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments of the invention will be apparent to those skilled in the art in light of the instant disclosure, which do not depart from the invention. Hence, the following descriptions are intended to illustrate some particular embodiments of the invention, and not to exhaustively specify all permutations, combinations and variations thereof. Those of ordinary skill in the art will recognize that modifications and variations in the embodiments described herein may be made without departing from the spirit or scope of the invention.

Definitions

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

For clarity, certain terms used in the specification are defined and presented as follows:

As used herein, "a," "an" or "the" can mean one or more than one. For example, "a cell" can mean a single cell or a multiplicity of cells.

As used herein, "and/or" refers to and encompasses any and all possible combinations of one or more of the associated listed items, as well as the lack of combinations when interpreted in the alternative, "or."

Further, the term "about," as used herein when referring to a measurable value such as an amount of a compound or agent, dose, time, temperature, and the like, is meant to encompass variations of ±20%, ±10%, ±5%, ±1%, ±0.5%, or even ±0.1% of the specified amount.

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

The terms "complementary" or "complementarity," refer to the natural binding of polynucleotides under permissive salt and temperature conditions by base-pairing. Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands. Complementary polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. For example, the sequence "A-G-T" binds to the complementary sequence "T-C-A." It is understood that two polynucleotides may hybridize to each other even if they are not completely complementary to each other, provided that each has at least one region that is substantially complementary to the other.

As used herein, the terms "substantially complementary" or "partially complementary" mean that two nucleic acid sequences are complementary at least about 50%, 60%, 70%, 80% or 90% of their nucleotides. In some embodiments, the two nucleic acid sequences can be complementary at least at 85%, 90%, 95%, 96%, 97%, 98%, 99% or more of their nucleotides. The terms "substantially complementary" and "partially complementary" can also mean that two nucleic acid sequences can hybridize under high stringency conditions and such conditions are well known in the art.

To "control" insects means to inhibit, through a toxic effect, the ability of insect pests to survive, grow, feed, or reproduce, or to limit insect-related damage or loss in crop plants or to protect the yield potential of a crop when grown in the presence of insect pests. To "control" insects may or may not mean killing the insects, although it preferably means killing the insects.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

To "deliver" a composition or toxic RNA means that the composition or toxic RNA comes in contact with an insect, which facilitates the oral ingestion of the composition or toxic RNA, resulting in a toxic effect and control of the insect. The composition or toxic RNA can be delivered in many recognized ways, including but not limited to, transgenic plant expression, formulated interfering RNA composition(s), sprayable interfering RNA composition(s), a bait matrix, or any other art-recognized RNA delivery system.

"Expression cassette" as used herein means a nucleic acid molecule capable of directing expression of at least one polynucleotide of interest, such as a polynucleotide that encodes an interfering RNA of the invention, in an appropriate host cell, comprising a promoter operably linked to the polynucleotide of interest which is operably linked to a termination signal. An "expression cassette" may also comprise additional polynucleotides required for proper translation of a polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is a defined region that is located within a genome and that, besides the aforementioned coding sequence, comprises other, primarily regulatory nucleic acid sequences responsible for the control of the expression, that is to say the transcription and translation, of the coding portion. A gene may also comprise other 5' and 3' untranslated sequences and termination sequences. Further elements that may be present are, for example, introns.

The term "heterologous" when used in reference to a gene or a polynucleotide or a polypeptide refers to a gene or a polynucleotide or a polypeptide that is or contains a part thereof not in its natural environment (i.e., has been altered by the hand of man). For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Insecticidal" is defined as a toxic biological activity capable of controlling insects, preferably by killing them.

The term "isolated" nucleic acid molecule, polynucleotide or protein is a nucleic acid molecule, polynucleotide or protein that no longer exists in its natural environment. An isolated nucleic acid molecule, polynucleotide or protein of the invention may exist in a purified form or may exist in a recombinant host such as in a transgenic bacteria or a transgenic plant. Therefore, a claim to an "isolated" nucleic acid molecule, as enumerated herein, encompasses a nucleic acid molecule when the nucleic acid molecule is comprised within a transgenic bacteria or plant genome.

The term "homology" in the context of the invention refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For an amino acid sequence, the sequences should be compared using algorithms (for instance see section on "identity" and "substantial identity"). For nucleotide sequences the sequence of one DNA molecule can be compared to the sequence of a known or putative homologue in much the same way. Homologues are at least 20% identical, or at least 30% identical, or at least 40% identical, or at least 50% identical, or at least 60% identical, or at least 70% identical, or at least 80% identical, or at least 88% identical, or at least 90% identical, or at least 92% identical, or at least 95% identical, across any substantial region of the molecule (DNA, RNA, or protein molecule).

The terms "sequence similarity" or "sequence identity" of nucleotide or amino acid sequences mean a degree of identity or similarity of two or more sequences and may be determined conventionally by using known software or computer programs such as the Best-Fit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482-489 (1981), to find the best segment of identity or similarity between two sequences. Sequence comparison between two or more polynucleotides or polypeptides is generally performed by comparing portions of the two sequences over a comparison window to identify and compare local regions of sequence similarity. The comparison window is generally from about 20 to 200 consecutive nucleotides. Gap performs global alignments: all of one sequence with all of another similar sequence using the method of Needleman and Wunsch, J. Mol. Biol. 48:443-453 (1970). When using a sequence alignment program such as BestFit to determine the degree of DNA sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The phrase "substantially identical," in the context of two nucleic acids or two amino acid sequences, refers to two or more sequences or subsequences that have at least about 50% nucleotide or amino acid residue identity when compared and aligned for maximum correspondence as measured using one of the following sequence comparison algorithms or by visual inspection. In certain embodiments, substantially identical sequences have at least about 60%, or at least about 70%, or at least about 80%, or even at least about 90% or 95% nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Two nucleotide sequences can also be considered to be substantially identical when the two sequences hybridize to each other under stringent conditions. In representative embodiments, two nucleotide sequences considered to be substantially identical hybridize to each other under highly stringent conditions.

The terms "stringent conditions" or "stringent hybridization conditions" include reference to conditions under which a polynucleotide will hybridize to its target sequence to a detectably greater degree than other sequences (e.g., at least 2-fold over background). Stringent conditions are sequence-dependent and will be different in different circumstances. By controlling the stringency of the hybridization and/or washing conditions, target polynucleotides can be identified which are 100% complementary to the probe (homologous probing). Alternatively, stringency conditions can be adjusted to allow some mismatching in sequences so that lower degrees of similarity are detected (heterologous probing). Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Moderate stringency conditions detect sequences that share at least 80% sequence identity. Exemplary moderate stringency conditions include hybridization in 40 to 45% formamide, 1 M NaCl, 1% SDS at 37° C., and a wash in 0.5× to 1×SSC at 55 to 60° C. High stringency conditions detect sequences that share at least 90% sequence identity. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA—DNA hybrids, the Tm can be approximated from the equation of Meinkoth and Wahl (Anal. Biochem., 138:267-284, 1984): Tm=81.5° C.+16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., eds., Greene Publishing and Wiley-Interscience, New York (1995). Methods of stringent hybridization are known in the art which conditions can be calculated by means known in the art. This is disclosed in Sambrook et al., Molecular Cloning: A Laboratory Manual, 2nd Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

As used herein, "dsRNA" or "interfering RNA" refers to a polyribonucleotide structure formed either by a single self-complementary RNA strand or at least by two complementary RNA strands. The degree of complementary, in other words the % identity, need not necessarily be 100%. Rather, it must be sufficient to allow the formation of a double-stranded structure under the conditions employed. As used herein, the term "fully complementary" means that all the bases of the nucleotide sequence of the dsRNA are complementary to or 'match' the bases of the target nucleotide sequence. The term "at least partially complementary" means that there is less than a 100% match between the bases of the dsRNA and the bases of the target nucleotide sequence. The skilled person will understand that the dsRNA need only be at least partially complementary to the target nucleotide sequence in order to mediate down-regulation of expression of the target gene. It is known in the art that RNA sequences with insertions, deletions and mismatches relative to the target sequence can still be effective at RNAi. According to the current invention, it is preferred that the dsRNA and the target nucleotide sequence of the target gene share at least 80% or 85% sequence identity, preferably at least 90% or 95% sequence identity, or more preferably at least 97% or 98% sequence identity and still more preferably at least 99% sequence identity. Alternatively, the dsRNA may comprise 1, 2 or 3 mismatches as compared with the target nucleotide sequence over every length of 24 partially complementary nucleotides. It will be appreciated by the person skilled in the art that the degree of complementarity shared between the dsRNA and the target nucleotide sequence may vary depending on the target gene to be down-regulated or depending on the insect pest species in which gene expression is to be controlled.

It will be appreciated that the dsRNA may comprise or consist of a region of double-stranded RNA comprising annealed complementary strands, one strand of which, the sense strand, comprises a sequence of nucleotides at least partially complementary to a target nucleotide sequence within a target gene.

The target nucleotide sequence may be selected from any suitable region or nucleotide sequence of the target gene or RNA transcript thereof. For example, the target nucleotide sequence may be located within the 5'UTR or 3'UTR of the target gene or RNA transcript or within exonic or intronic regions of the gene. The skilled person will be aware of methods of identifying the most suitable target nucleotide sequences within the context of the full-length target gene. For example, multiple dsRNAs targeting different regions of the target gene can be synthesized and tested. Alternatively, digestion of the RNA transcript with enzymes such as RNAse H can be used to determine sites on the RNA that are in a conformation susceptible to gene silencing. Target sites may also be identified using in silico approaches, for example, the use of computer algorithms designed to predict the efficacy of gene silencing based on targeting different sites within the full-length gene.

Preferably, the percent identity of a polyribonucleotide is determined by GAP (Needleman and Wunsch, 1970) analysis (GCG program) using the default settings, wherein the query sequence is at least about 21 to about 23 nucleotides in length, and the GAP analysis aligns the two sequences over a region of at least about 21 nucleotides. In another embodiment, the query sequence is at least 150 nucleotides in length, and the GAP analysis aligns the two sequences over a region of at least 150 nucleotides. In a further embodiment, the query sequence is at least 300 nucleotides in length and the GAP analysis aligns the two sequences over a region of at least 300 nucleotides. In yet another embodiment, the query sequence corresponds to the full length of the target RNA, for example mRNA, and the GAP analysis aligns the two sequences over the full length of the target RNA.

Conveniently, the dsRNA can be produced from a single open reading frame in a recombinant host cell, wherein the sense and anti-sense sequences are flanked by an unrelated sequence which enables the sense and anti-sense sequences to hybridize to form the dsRNA molecule with the unrelated sequence forming a loop structure. Alternatively, the sense strand and antisense strand can be made without an open reading frame to ensure that no protein will be made in the transgenic host cell. The two strands can also be expressed separately as two transcripts, one encoding the sense strand and one encoding the antisense strand.

RNA duplex formation can be initiated either inside or outside the cell. The dsRNA can be partially or fully double-stranded. The RNA can be enzymatically or chemically synthesized, either in vitro or in vivo.

The dsRNA need not be full length relative to either the primary transcription product or fully processed RNA. It is well-known in the art that small dsRNA of about 19-23 bp in length can be used to trigger gene silencing of a target gene. Generally, higher identity can be used to compensate for the use of a shorter sequence. Furthermore, the dsRNA can comprise single stranded regions as well, e.g., the dsRNA can be partially or fully double stranded. The double stranded region of the dsRNA can have a length of at least about 19 to about 23 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs, up to a molecule that is double stranded for its full length, corresponding in size to a full length target RNA molecule. Bolognesi et al (2012, *PLOS One,* 7(10): e47534, herein incorporated by reference) teach that dsRNAs greater than or equal to about 60 bp are required for biological activity in artificial diet bioassays with Southern Corn Rootworm (SCR; *Diabrotica undecimpunctata howardii*).

Mao et al (2007, *Nature Biotechnology,* 35(11): 1307-1313) teach a transgenic plant expressing a dsRNA construct against a target gene (CYP6AE14) of an insect pest (cotton bollworm, *Helicoverpa armigera*). Insects feeding on the transgenic plant have small RNAs of about 19-23 bp in size of the target gene in their midgut, with a corresponding reduction in CYP6AE14 transcripts and protein. This suggests that the small RNAs were efficacious in reducing expression of the target gene in the insect pest. Therefore, small RNAs of about 19 bp, about 20 bp, about 21 bp, about 22 bp, about 23 bp, about 24 bp, about 25 bp, about 26 bp, about 27 bp, about 28 bp, about 29 bp, or about 30 bp may be efficacious in reducing expression of the target gene in an insect pest.

Alternatively, the dsRNA may comprise a target dsRNA of at least 19 base pairs, and the target dsRNA may be within a dsRNA "carrier" or "filler" sequence. For example, Bolognesi et al (2012) show that a 240 bp dsRNA encompassing a target dsRNA, which comprised a 21 bp consecutive sequence with 100% identity to the target sequence, had biological activity in bioassays with Southern Corn Rootworm. The present application exemplifies a similar approach in bioassays with Western Corn Rootworm. The target dsRNA may have a length of at least 19 to about 25 base pairs, optionally a sequence of about 19 to about 50 base pairs, optionally a sequence of about 50 to about 100 base pairs, optionally a sequence of about 100 to about 200 base pairs, optionally a sequence of about 200 to about 500, and optionally a sequence of about 500 to about 1000 or more base pairs. Combined with the carrier dsRNA sequence, the dsRNA of the target sequence and the carrier dsRNA may have a total length of at least about 50 to about 100 base pairs, optionally a sequence of about 100 to about 200 base pairs, optionally a sequence of about 200 to about 500, and optionally a sequence of about 500 to about 1000 or more base pairs.

The dsRNA can contain known nucleotide analogs or modified backbone residues or linkages, which are synthetic, naturally occurring, and non-naturally occurring. Examples of such analogs include, without limitation, phosphorothioates, phosphoramidates, methyl phosphonates, chiralmethyl phosphonates and 2-O-methyl ribonucleotides.

As used herein, the term "specifically reduce the level of a target RNA and/or the production of a target protein encoded by the RNA", and variations thereof, refers to the sequence of a portion of one strand of the dsRNA being sufficiently identical to the target RNA such that the presence of the dsRNA in a cell reduces the steady state level and/or the production of said RNA. In many instances, the target RNA will be mRNA, and the presence of the dsRNA in a cell producing the mRNA will result in a reduction in the production of said protein. Preferably, this accumulation or production is reduced at least 10%, more preferably at least 50%, even more preferably at least 75%, yet even more preferably at least 95% and most preferably 100%, when compared to a wild-type cell.

The consequences of inhibition can be confirmed by examination of the outward properties of the cell or organism or by biochemical techniques such as, but not limited to, Northern hybridization, reverse transcription, gene expression monitoring with a microarray, antibody binding, enzyme linked immunosorbent assay (ELISA), Western blotting, radioimmunoassay (RIA), and other immunoassays.

The interfering RNAs of the invention may comprise one dsRNA or multiple dsRNAs, wherein each dsRNA comprises or consists of a sequence of nucleotides which is at least partially complementary to a target nucleotide sequence within the target gene and that functions upon uptake by an insect pest species to down-regulate expression of said target gene. Concatemeric RNA constructs of this type are described in WO2006/046148 as incorporated herein by reference. In the context of the present invention, the term 'multiple' means at least two, at least three, at least four, etc and up to at least 10, 15, 20 or at least 30. In one embodiment, the interfering RNA comprises multiple copies of a single dsRNA i.e. repeats of a dsRNA that binds to a particular target nucleotide sequence within a specific target gene. In another embodiment, the dsRNAs within the interfering RNA comprise or consist of different sequences of nucleotides complementary to different target nucleotide sequences. It should be clear that combinations of multiple copies of the same dsRNA combined with dsRNAs binding to different target nucleotide sequences are within the scope of the current invention.

The dsRNAs may be arranged as one contiguous region of the interfering RNA or may be separated by the presence of linker sequences. The linker sequence may comprise a short random nucleotide sequence that is not complementary to any target nucleotide sequences or target genes. In one embodiment, the linker is a conditionally self-cleaving RNA sequence, preferably a pH-sensitive linker or a hydrophobic-sensitive linker. In one embodiment, the linker comprises a sequence of nucleotides equivalent to an intronic sequence. Linker sequences of the current invention may range in length from about 1 base pair to about 10000 base pairs, provided that the linker does not impair the ability of the interfering RNA to down-regulate the expression of target gene(s).

In addition to the dsRNA(s) and any linker sequences, the interfering RNA of the invention may comprise at least one additional polynucleotide sequence. In different embodiments of the invention, the additional sequence is chosen from (i) a sequence capable of protecting the interfering RNA against RNA processing, (ii) a sequence affecting the stability of the interfering RNA, (iii) a sequence allowing protein binding, for example to facilitate uptake of the interfering RNA by cells of the insect pest species, (iv) a sequence facilitating large-scale production of the interfering RNA, (v) a sequence which is an aptamer that binds to a receptor or to a molecule on the surface of the insect pest cells to facilitate uptake, or (v) a sequence that catalyzes processing of the interfering RNA within the insect pest cells and thereby enhances the efficacy of the interfering RNA. Structures for enhancing the stability of RNA molecules are well known in the art and are described further in WO2006/046148 as incorporated herein by reference.

The interfering RNA may contain DNA bases, non-natural bases or non-natural backbone linkages or modifications of the sugar-phosphate backbone, for example to enhance stability during storage or enhance resistance to degradation by nucleases. Furthermore, the interfering RNA may be produced chemically or enzymatically by one skilled in the art through manual or automated reactions. Alternatively, the interfering RNA may be transcribed from a polynucleotide encoding the same. Thus, provided herein is an isolated polynucleotide encoding any of the interfering RNAs of the current invention.

MicroRNAs (miRNAs) are non-protein coding RNAs, generally of between about 18 to about 25 nucleotides in length (commonly about 20-24 nucleotides in length in plants). These miRNAs direct cleavage in trans of target transcripts, negatively regulating the expression of genes involved in various regulation and development pathways (Bartel, *Cell*, 116:281-297 (2004); Zhang et al. *Dev. Biol.* 289:3-16 (2006)). As such, miRNAs have been shown to be involved in different aspects of plant growth and development as well as in signal transduction and protein degradation. In addition, small endogenous mRNAs including miRNAs may also be involved in biotic stress responses such as pathogen attack. Since the first miRNAs were discovered in plants (Reinhart et al. *Genes Dev.* 16:1616-1626 (2002), Park et al. *Curr. Biol.* 12:1484-1495 (2002)) many hundreds have been identified. Furthermore, many plant miRNAs have been shown to be highly conserved across very divergent taxa. (Floyd et al. *Nature* 428:485-486 (2004); Zhang et al. *Plant J.* 46:243-259 (2006)). Many microRNA genes (MIR genes) have been identified and made publicly available in a database (miRBase, available via the World Wide Web). miRNAs are also described in U.S. Patent Publications 2005/0120415 and 2005/144669A1, the entire contents of which are incorporated by reference herein.

Genes encoding miRNAs yield primary miRNAs (termed a "pri-miRNA") of 70 to 300 bp in length that can form imperfect stem—loop structures. A single pri-miRNA may contain from one to several miRNA precursors. In animals, pri-miRNAs are processed in the nucleus into shorter hairpin RNAs of about 65 nt (pre-miRNAs) by the RNaseIII enzyme Drosha and its cofactor DGCR8/Pasha. The pre-miRNA is then exported to the cytoplasm, where it is further processed by another RNaseIII enzyme, Dicer, releasing a miRNA/miRNA* duplex of about 22 nt in size. In contrast to animals, in plants, the processing of pri-miRNAs into mature miRNAs occurs entirely in the nucleus using a single RNaseIII enzyme, DCL1 (Dicer-like 1). (Zhu. *Proc. Natl. Acad. Sci.* 105:9851-9852 (2008)). Many reviews on microRNA biogenesis and function are available, for example, see, Bartel *Cell* 116:281-297 (2004), Murchison et al. *Curr. Opin. Cell Biol.* 16:223-229 (2004), Dugas et al. *Curr. Opin. Plant Biol.* 7:512-520 (2004) and Kim *Nature Rev. Mol. Cell Biol.* 6:376-385 (2005).

The term "plant microRNA precursor molecule" as used herein describes a small (-70-300 nt) non-coding RNA sequence that is processed by plant enzymes to yield a ~19-24 nucleotide product known as a mature microRNA sequence. The mature sequences have regulatory roles through complementarity to messenger RNA (mRNA). The term "artificial plant microRNA precursor molecule" describes the non-coding miRNA precursor sequence prior to processing that is employed as a backbone sequence for the delivery of a siRNA molecule via substitution of the endogenous native miRNA/miRNA* duplex of the miRNA precursor molecule with that of a non-native, heterologous miRNA (amiRNA/amiRNA*; e.g. siRNA/siRNA*) that is then processed into the mature miRNA sequence with the siRNA sequence.

In the context of the invention, the term "toxic" used to describe a dsRNA of the invention means that the dsRNA molecules of the invention and combinations of such dsRNA molecules function as orally active insect control agents that have a negative effect on an insect. When a composition of the invention is delivered to the insect, the result is typically death of the insect, or the insect does not feed upon the source that makes the composition available to the insect. Such a composition may be a formulated product comprising the dsRNA of the invention that is topically applied to a plant or plant part such as a seed, or such composition may be a transgenic plant expressing the dsRNA of the invention.

The term "agrochemically active ingredient" refers to chemicals and/or biological compositions, such as those described herein, which are effective in killing, preventing, or controlling the growth of undesirable pests, such as, plants, insects, mice, microorganism, algae, fungi, bacteria, and the like (such as pesticidal active ingredients). An interfering RNA molecule of the invention is an agrochemically active ingredient.

An "agriculturally acceptable carrier" includes adjuvants, mixers, enhancers, etc. beneficial for application of an active ingredient, such as an interfering RNA molecule of the invention. Suitable carriers should not be phytotoxic to valuable crops, particularly at the concentrations employed in applying the compositions in the presence of crops, and should not react chemically with the compounds of the active ingredient herein, namely an interfering RNA of the invention, or other composition ingredients. Such mixtures can be designed for application directly to crops, or can be concentrates or formulations which are normally diluted with additional carriers and adjuvants before application. They may include inert or active components and can be solids, such as, for example, dusts, granules, water dispersible granules, or wettable powders, or liquids, for example, emulsifiable concentrates, solutions, emulsions or suspensions. Suitable agricultural carriers may include liquid carriers, for example water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates. Suitable solid carriers may include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like.

For the invention, an agriculturally acceptable carrier may also include non-pathogenic, attenuated strains of microorganisms, which carry the insect control agent, namely an interfering RNA molecule of the invention. In this case, the microorganisms carrying the interfering RNA may also be referred to as insect control agents. The microorganisms may be engineered to express a nucleotide sequence of a target gene to produce interfering RNA molecules comprising RNA sequences homologous or complementary to RNA sequences typically found within the cells of an insect. Exposure of the insects to the microorganisms result in ingestion of the microorganisms and down-regulation of expression of target genes mediated directly or indirectly by the interfering RNA molecules or fragments or derivatives thereof.

In another embodiment, the interfering RNA molecules may be encapsulated in a synthetic matrix such as a polymer and applied to the surface of a host such as a plant. Ingestion of the host cells by an insect permits delivery of the insect control agents to the insect and results in down-regulation of a target gene in the host.

A composition of the invention, for example a composition comprising an interfering RNA molecule of the invention and an agriculturally acceptable carrier, may be used in conventional agricultural methods. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

In the context of the invention, a number in front of the suffix "mer" indicates a specified number of subunits. When applied to RNA or DNA, this specifies the number of bases in the molecule. For example, a 19 nucleotide subsequence of an mRNA having the sequence ACUGGUCGCGUUG-CAUGCU is a "19-mer."

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated herein by their bases by the following standard abbreviations: adenine (A), cytosine (C), thymine (T), guanine (G) and uracil (U).

The invention is based on the unexpected result that double stranded RNA (dsRNA) or small interfering RNAs (siRNA) designed to target a mRNA transcribable from a pest insect essential gene, particularly an Rpt5 essential gene described herein, are toxic to the pest insect and can be used to control pest insect infestation of a plant and impart to a transgenic plant tolerance to a pest insect infestation, particularly a coleopteran pest insect infestation. An interfering RNA molecule of the invention does not occur in nature. Thus, in some aspects, the invention provides a dsRNA molecule comprising a sense strand and an antisense strand, wherein a nucleotide sequence of the antisense strand is complementary to a portion of a mRNA polynucleotide transcribable from a pest insect Rpt5 gene described herein, wherein the dsRNA molecule is toxic to a pest insect, particularly to at least a coleopteran pest insect.

Nucleic acid molecules comprising the sequence of Rpt5 from multiple insect pest species are disclosed herein as SEQ ID NOs:1-9. Specific fragments of these sequences are also disclosed herein as SEQ ID NOs:11-19. In addition, the skilled person will recognize that nucleic acid molecules comprising the complement of SEQ ID NOs:1-9 or SEQ ID NOs:11-19 can also be determined from SEQ ID NOs:1-9 and SEQ ID NOs:11-19, respectively. The sequences of Rpt5 and/or a fragment thereof can be targeted by an interfering RNA of the invention which may cause cessation of feeding, growth, development and/or reproduction of a pest insect, and eventually results in the death of the pest insect. In some aspects of the invention, an interfering RNA molecule of the invention comprises, consists essentially of or consists of any of SEQ ID NOs:20-37, or a complement thereof.

In some embodiments, the invention encompasses an RNA encoded by a sequence comprising, consisting essentially of or consisting of any of SEQ ID NOs:1-9, any at least 19 nucleotide fragment of any of SEQ ID NOs:1-9, the complement of any at least 19 nucleotide fragment of any one of SEQ ID NOs:1-9, or a sequence that hybridizes under stringent conditions with any of the aforementioned sequences, wherein the RNA post transcriptionally silences an essential gene in a plant pest organism and wherein the RNA encoding sequence is not a sequence comprising SEQ ID NO:10, the complement of SEQ ID NO:10, any at least 19 nucleotide fragment of SEQ ID NO:10, the complement of any at least 19 nucleotide fragment of SEQ ID NO:10 or a sequence that hybridizes under stringent conditions with SEQ ID NO:10, or the complement or a fragment thereof.

It is known in the art that dsRNA molecules that are not perfectly complementary to a target sequence (for example, having only 95% identity to the target gene) are effective to control coleopteran pests (see, for example, Narva et al., U.S. Pat. No. 9,012,722). The invention provides an interfering RNA molecule comprising at least one dsRNA, where the dsRNA is a region of double-stranded RNA comprising annealed at least partially complementary strands, a sense strand and an antisense strand. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides which is at least partially complementary to a target nucleotide sequence within an insect pest target gene. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:20-37, or the complement thereof; (ii) comprises, consists essentially of or consists of at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of any one of SEQ ID NOs:20-37, or the complement thereof; (iii) comprises, consists essentially of or consists of at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 300 consecutive nucleotide fragment of a nucleotide sequence encoding an amino acid sequence encoded by any one of SEQ ID NOs:20-37, or the complement thereof, or (iv) can hybridize under stringent conditions to a polynucleotide selected from the group consisting of SEQ ID NOs:20-37, and the complements thereof, wherein the interfering RNA molecule has insecticidal activity against at least a coleopteran insect pest. In some embodiments, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera.*

In some embodiments, the interfering RNA molecule comprises at least two dsRNAs, wherein each dsRNA comprises a sequence of nucleotides which is at least partially complementary to a target nucleotide sequence within the target gene. In some embodiments the target gene comprises, consists essentially of or consists of any one of SEQ ID NOs:1-9. In some embodiments, each of the dsRNAs comprise a different sequence of nucleotides which is complementary to a different target nucleotide sequence within the target gene. In other embodiments, each of the dsRNAs comprise a different sequence of nucleotides which is complementary to a target nucleotide sequence within two different target genes.

In some embodiments, the interfering RNA molecule comprises a dsRNA that can comprise, consist essentially of or consist of from at least 18 to about 25 consecutive nucleotides (e.g. 18, 19, 20, 21, 22, 23, 24, 25, 26, 27, 28, or 29) to at least about 300 consecutive nucleotides. Additional nucleotides can be added at the 3' end, the 5' end or both the 3' and 5' ends to facilitate manipulation of the dsRNA molecule but that do not materially affect the basic characteristics or function of the dsRNA molecule in RNA interference (RNAi).

In some embodiments, the interfering RNA molecule comprises a dsRNA which comprises, consists essentially of or consists of an antisense strand that is complementary to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of SEQ ID NOs:20-37, or the complement thereof. In other embodiments, the portion of dsRNA comprises, consists essentially of or consists of at least from 19, 20 or 21 consecutive nucleotides to at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 consecutive nucleotides of any one of SEQ ID NOs:20-37, or the complement thereof.

In other embodiments, an interfering RNA molecule of the invention comprises a dsRNA which comprises, consists essentially of or consists of any 21-mer subsequence of any one of SEQ ID NOs:29-37 consisting of N to N+20 nucleotides, or any complement thereof. For example, an interfering RNA molecule of the invention comprises a dsRNA which comprises, consist essentially of or consists of any 21-mer subsequence of SEQ ID NO:29, wherein N is nucleotide 1 to nucleotide 2863 of SEQ ID NO:29, or any complement thereof. In other words, the portion of the mRNA that is targeted comprises any of the 2,863 21 consecutive nucleotide subsequences i.e. 21-mers, of SEQ ID NO:29, or any of their complementing sequences.

In still other embodiments, the interfering RNA molecule of the invention comprises a dsRNA which comprises, consists essentially of or consists of SEQ ID NO:20-37, or the complement thereof.

In other embodiments, the interfering RNA molecule comprises the antisense strand of a dsRNA of the invention which comprises, consists essentially of or consists of the antisense of any one of nucleotide sequences SEQ ID NOs:20-37. The nucleotide sequence of the antisense strand of a dsRNA of the invention can have one nucleotide at either the 3' or 5' end deleted or can have up to six nucleotides added at the 3' end, the 5' end or both, in any combination to achieve an antisense strand consisting essentially of any 19-mer, any 20-mer, or any 21-mer nucleotide sequence, as it would be understood that the deletion of the one nucleotide or the addition of up to the six nucleotides do not materially affect the basic characteristics or function of the double stranded RNA molecule of the invention. Such additional nucleotides can be nucleotides that extend the complementarity of the antisense strand along the target sequence and/or such nucleotides can be nucleotides that facilitate manipulation of the RNA molecule or a nucleic acid molecule encoding the RNA molecule, as would be known to one of ordinary skill in the art. For example, a TT overhang at the 3' end may be present, which is used to stabilize the siRNA duplex and does not affect the specificity of the siRNA.

In some embodiments of this invention, the antisense strand of the dsRNA of the interfering RNA molecule can be fully complementary to the target RNA polynucleotide or the antisense strand can be substantially complementary or partially complementary to the target RNA polynucleotide. The dsRNA of the interfering RNA molecule may comprise a dsRNA which is a region of double-stranded RNA comprising substantially complementary annealed strands, or which is a region of double-stranded RNA comprising fully complementary annealed strands. By substantially or partially complementary is meant that the antisense strand and the target RNA polynucleotide can be mismatched at about 1, 2, 3, 4, 5, 6, 7, 8, 9, or 10 nucleotide pairings. Such mismatches can be introduced into the antisense strand sequence, e.g., near the 3' end, to enhance processing of the double stranded RNA molecule by Dicer, to duplicate a pattern of mismatches in a siRNA molecule inserted into a chimeric nucleic acid molecule or artificial microRNA precursor molecule of this invention, and the like, as would be known to one of skill in the art. Such modification will weaken the base pairing at one end of the duplex and generate strand asymmetry, therefore enhancing the chance of the antisense strand, instead of the sense strand, being processed and silencing the intended gene (Geng and Ding "Double-mismatched siRNAs enhance selective gene silencing of a mutant ALS-causing Allelel" Acta Pharmacol. Sin. 29:211-216 (2008); Schwarz et al. "Asymmetry in the assembly of the RNAi enzyme complex" Cell 115:199-208 (2003)).

In some embodiments of the invention, the interfering RNA comprises a dsRNA which comprises a short hairpin RNA (shRNA) molecule. Expression of shRNA in cells is typically accomplished by delivery of plasmids or recombinant vectors, for example in transgenic plants such as transgenic corn, rice, wheat or soybean.

The invention encompasses a nucleic acid construct comprising an interfering RNA of the invention. The invention further encompasses a nucleic acid molecule encoding at least one interfering RNA molecule of the invention. The invention further encompasses a nucleic acid construct comprising at least one interfering RNA molecule of the invention or comprising a nucleic acid molecule encoding the at least one interfering RNA molecule of the invention. The invention further encompasses a nucleic acid construct wherein the nucleic acid construct is an expression vector. The invention further encompasses a recombinant vector comprising a regulatory sequence operably linked to a nucleotide sequence that encodes an interfering RNA molecule of the invention. A regulatory sequence may refer to a promoter, enhancer, transcription factor binding site, insulator, silencer, or any other DNA element involved in the expression of a gene.

The invention further encompasses chimeric nucleic acid molecules comprising an interfering RNA molecule with an antisense strand of a dsRNA operably linked with a plant microRNA precursor molecule. In some embodiments, the chimeric nucleic acid molecule comprises an antisense strand having the nucleotide sequence of any of the 21-mer subsequences of any one of SEQ ID NOs:29-37, or any complement thereof, operably linked with a plant microRNA precursor molecule. In some embodiments, the plant microRNA precursor molecule is a maize microRNA precursor.

In some embodiments, the invention encompasses an artificial plant microRNA precursor molecule comprising an antisense strand of a dsRNA of an interfering RNA molecule of the invention. In other embodiments, the artificial plant microRNA precursor molecule comprises an antisense strand having the nucleotide sequence of any of the 19-mer, 20-mer, or 21-mer subsequences of the antisense of any one of SEQ ID NOs:29-37. The use of artificial plant microRNAs to deliver a nucleotide sequence of interest (e.g. an artificial miRNA; siRNA/siRNA*) into a plant is known in the art (see, e.g., Schwab et al. 2006. The Plant Cell 18:1121-1133). In the invention, the artificial microRNAs are chimeric or hybrid molecules, having a plant microRNA precursor backbone and an insect siRNA sequence inserted therein. As would be understood by one of ordinary skill in the art, it is typically desirable to maintain mismatches that normally occur in the plant microRNA precursor sequence in any nucleotide sequence that is substituted into the plant microRNA precursor backbone. In still other embodiments, the artificial plant microRNA precursor comprises portions of a corn microRNA precursor molecule. Any corn microRNA (miRNA) precursor is suitable for the compositions and methods of the invention. Non-limiting examples include miR156, miR159, miR160, miR162, miR164, miR166, miR167, miR168, miR169, miR171, miR172, miR319, miR390, miR393, miR394, miR395, miR396, miR397, miR398, miR399, miR408, miR482, miR528, miR529, miR827, miR1432, as well as any other plant miRNA precursors now known or later identified.

In some embodiments, the invention encompasses interfering RNA molecules, nucleic acid constructs, nucleic acid molecules or recombinant vectors comprising at least one strand of a dsRNA of an interfering RNA molecule of the invention, or comprising a chimeric nucleic acid molecule of the invention, or comprising an artificial plant microRNA of the invention. In some embodiments the nucleic acid construct comprises a nucleic acid molecule of the invention. In other embodiments, the nucleic acid construct is a recombinant expression vector.

Plant pest insects that are targets of the present invention include those insects in the Orders Coleoptera (beetles), Lepidoptera (moths, butterflies), Diptera (flies), Protura, Collembola (springtails), Diplura, Microcoryphia (jumping bristletails), Thysanura (bristletails, silverfish), Ephemeroptera (mayflies), Odonata (dragonflies, damselflies), Orthoptera (grasshoppers, crickets, katydids), Phasmatodea (walkingsticks), Grylloblattodea (rock crawlers), Mantophasmatodea, Dermaptera (earwigs), Plecoptera (stoneflies), Embioptera (web spinners), Zoraptera, Isoptera (termites), Mantodea (mantids), Blattodea (cockroaches), Hemiptera (true bugs, cicadas, leafhoppers, aphids, scales), Thysanoptera (thrips), Psocoptera (book and bark lice), Phthiraptera (lice; including but not limited to suborders Amblycera, Ischnocera and Anoplura), Neuroptera (lacewings, owlflies, mantispids, antlions), Hymenoptera (bees, ants, wasps), Trichoptera (caddisflies), Siphonaptera (fleas), Mecoptera (scorpion flies), Strepsiptera (twisted-winged parasites). In some embodiments, a target insect is in the Order Coleoptera.

In some embodiments, target coleopteran insect pests of the invention are *Meligethes* species, *Sitophilus* species, *Ceuthorrhynchus* species, *Rhyzoperta* species, *Phyllotreta* species, *Psylliodes* species and/or *Diabrotica* species.

In other embodiments, insect pests that are targets of the invention are selected from the group consisting *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera*.

In some embodiments of the invention, the insect pest is a *Meligethes* species and the target sequence is a Rpt5 that comprises, consists essentially of or consists of SEQ ID NO:1, the complement of SEQ ID NO:1, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:1, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:1, or a sequence that hybridizes under stringent conditions with any of the aforementioned sequences; wherein the RNA is effective in inhibiting expression of the target Rpt5 sequence in a *Meligethes* species. In other embodiments, the insect pest species is *Meligethes aeneus* and the target sequence comprises, consists essentially of or consists of SEQ ID NO:11 or the complement thereof. In other embodiments, the target sequence comprises, consists essentially of or consists of SEQ ID NO:29, the complement of SEQ ID NO:29, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:29 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:29. In other embodiments, the RNA that effectively inhibits expression of the target Rpt5 sequence in *Meligethes aeneus* comprises, consists essentially of or consists of SEQ ID NO:20 or the complement thereof.

In some embodiments of the invention, the insect pest is a *Sitophilus* species and the target sequence is a Rpt5 that comprises, consists essentially of or consists of SEQ ID NO:2, the complement of SEQ ID NO:2, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:2, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:2, or a sequence that hybridizes under stringent conditions with any of the aforementioned sequences; wherein the RNA is effective in inhibiting expression of the target Rpt5 sequence in a *Sitophilus* species. In other embodiments, the insect pest species is *Sitophilus oryzae* and the target sequence comprises, consists essentially of or consists of SEQ ID NO:12 or the complement thereof. In other embodiments, the target sequence comprises, consists essentially of or consists of SEQ ID NO:30, the complement of SEQ ID NO:30, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:30 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:30. In other embodiments, the RNA that effectively inhibits expression of the target Rpt5 sequence in *Sitophilus oryzae* comprises, consists essentially of or consists of SEQ ID NO:21 or the complement thereof.

In some embodiments of the invention, the insect pest is a *Sitophilus* species and the target sequence is a Rpt5 that comprises, consists essentially of or consists of SEQ ID NO:3, the complement of SEQ ID NO:3, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:3, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:3, or a sequence that hybridizes under stringent conditions with any of the aforementioned sequences; wherein the RNA is effective in inhibiting expression of the target Rpt5 sequence in a *Sitophilus* species. In other embodiments, the insect pest species is Sitophilus granarius and the target sequence comprises, consists essentially of or consists of SEQ ID NO:13 or the complement thereof. In other embodiments, the target sequence comprises, consists essentially of or consists of SEQ ID NO:31, the complement of SEQ ID NO:31, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:31 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:31. In other embodiments, the RNA that effectively inhibits expression of the target Rpt5 sequence in *Sitophilus granarius* comprises, consists essentially of or consists of SEQ ID NO:22 or the complement thereof.

In some embodiments of the invention, the insect pest is a *Ceutorhynchus* species and the target sequence is a Rpt5 that comprises, consists essentially of or consists of SEQ ID NO:4, the complement of SEQ ID NO:4, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:4, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:4, or a sequence that hybridizes under stringent conditions with any of the aforementioned sequences; wherein the RNA is effective in inhibiting expression of the target Rpt5 sequence in a *Ceutorhynchus* species. In other embodiments, the insect pest species is *Ceutorhynchus assimilis* and the target sequence comprises, consists essentially of or consists of SEQ ID NO:14 or the complement thereof. In other embodiments, the target sequence comprises, consists essentially of or consists of SEQ ID NO:32, the complement of SEQ ID NO:32, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:32 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:32. In other embodiments, the RNA that effectively inhibits expression of the target Rpt5 sequence in *Ceutorhynchus assimilis* comprises, consists essentially of or consists of SEQ ID NO:23 or the complement thereof.

In some embodiments of the invention, the insect pest is a *Rhyzopertha* species and the target sequence is a Rpt5 that comprises, consists essentially of or consists of SEQ ID NO:5, the complement of SEQ ID NO:5, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:5, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:5, or a sequence that hybridizes under stringent conditions with any of the aforementioned sequences; wherein the RNA is effective in inhibiting expression of the target Rpt5 sequence in a *Rhyzopertha* species. In other embodiments, the insect pest species is *Rhyzopertha dominica* and the target sequence comprises, consists essentially of or consists of SEQ ID NO:15 or the complement thereof. In other embodiments, the target sequence comprises, consists essentially of or consists of SEQ ID NO:33, the complement of SEQ ID NO:33, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:33 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:33. In other embodiments, the RNA that effectively inhibits expression of the target Rpt5 sequence in *Rhyzopertha dominica* comprises, consists essentially of or consists of SEQ ID NO:24 or the complement thereof.

In some embodiments of the invention, the insect pest is a *Phyllotreta* species and the target sequence is a Rpt5 that comprises, consists essentially of or consists of SEQ ID NO:6, the complement of SEQ ID NO:6, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:6, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:6, or a sequence that hybridizes under stringent conditions with any of the aforementioned sequences; wherein the RNA is effective in inhibiting expression of the target Rpt5 sequence in a *Phyllotreta* species. In other embodiments, the insect pest species is *Phyllotreta nemorum* and the target sequence comprises, consists essentially of or consists of SEQ ID NO:16 or the complement thereof. In other embodiments, the target sequence comprises, consists essentially of or consists of SEQ ID NO:34, the complement of SEQ ID NO:34, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:34 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:34. In other embodiments, the RNA that effectively inhibits expression of the target Rpt5 sequence in *Phyllotreta nemorum* comprises, consists essentially of or consists of SEQ ID NO:25 or the complement thereof.

In some embodiments of the invention, the insect pest is a *Psylliodes* species and the target sequence is a Rpt5 that comprises, consists essentially of or consists of SEQ ID NO:7, the complement of SEQ ID NO:7, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:7, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:7, or a sequence that hybridizes under stringent conditions with any of the aforementioned sequences; wherein the RNA is effective in inhibiting expression of the target Rpt5 sequence in a *Psylliodes* species. In other embodiments, the insect pest species is *Psylliodes chrysocephala* and the target sequence comprises, consists essentially of or consists of SEQ ID NO:17 or the complement thereof. In other embodiments, the target sequence comprises, consists essentially of or consists of SEQ ID NO:35, the complement of SEQ ID NO:35, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:35 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:35. In other embodiments, the RNA that effectively inhibits expression of the target Rpt5 sequence in Psylliodes chrysocephala comprises, consists essentially of or consists of SEQ ID NO:26 or the complement thereof.

In some embodiments of the invention, the insect pest is a *Phyllotreta* species and the target sequence is a Rpt5 that comprises, consists essentially of or consists of SEQ ID NO:8, the complement of SEQ ID NO:8, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:8, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:8, or a sequence that hybridizes under stringent conditions with any of the aforementioned sequences; wherein the RNA is effective in inhibiting expression of the target Rpt5 sequence in a *Phyllotreta* species. In other embodiments, the insect pest species is *Phyllotreta striolata* and the target sequence comprises, consists essentially of or consists of SEQ ID NO:18 or the complement thereof. In other embodiments, the target sequence comprises, consists essentially of or consists of SEQ ID NO:36, the complement of SEQ ID NO:36, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:36 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:36. In other embodiments, the RNA that effectively inhibits expression of the target Rpt5 sequence in Phyllotreta striolata comprises, consists essentially of or consists of SEQ ID NO:27 or the complement thereof.

In some embodiments of the invention, the insect pest is a *Diabrotica* species and the target sequence is a Rpt5 that comprises, consists essentially of or consists of SEQ ID NO:9, the complement of SEQ ID NO:9, any at least 19, at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:9, the complement of any at least 19 at least 20, at least 21, at least 22, at least 23, at least 24, at least 25, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 or more nucleotide fragment of SEQ ID NO:9, or a sequence that hybridizes under stringent conditions with any of the aforementioned sequences; wherein the RNA is effective in inhibiting expression of the target Rpt5 sequence in a *Diabrotica* species. In other embodiments, the insect pest species is *Diabrotica virgifera* and the target sequence comprises, consists essentially of or consists of SEQ ID NO:19 or the complement thereof. In other embodiments, the target sequence comprises, consists essentially of or consists of SEQ ID NO:37, the complement of SEQ ID NO:37, a sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with SEQ ID NO:37 or any sequence that has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity with the complement of SEQ ID NO:37. In other embodiments, the RNA that effectively inhibits expression of the target Rpt5 sequence in *Diabrotica virgifera* comprises, consists essentially of or consists of SEQ ID NO:28 or the complement thereof.

In some embodiments, the invention encompasses a composition comprising one or more or two or more of the interfering RNA molecules of the invention. In some embodiments, the interfering RNA molecules are present on the same nucleic acid construct, on different nucleic acid constructs, or any combination thereof. For example, one interfering RNA molecule of the invention may be present on a nucleic acid construct, and a second interfering RNA molecule of the invention may be present on the same nucleic acid construct or on a separate, second nucleic acid construct. The second interfering RNA molecule of the invention may be to the same target gene or to a different target gene.

In some embodiments, the invention encompasses a composition comprising an interfering RNA molecule which comprises at least one dsRNA wherein the dsRNA is a region of double-stranded RNA comprising annealed complementary strands. One strand of the dsRNA comprises a sequence of at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 600 consecutive nucleotides which is at least partially complementary to a target nucleotide sequence within a target gene comprising, consisting essentially of or consisting of any one of SEQ ID NOs:1-9. The interfering RNA molecule (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37, or the complement thereof; (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37 or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of a nucleotide sequence encoding an amino acid sequence encoded by any one of SEQ ID NOs:20-37, or the complement thereof, or (iv) can hybridize under stringent conditions to a polynucleotide selected from the group consisting of any one of SEQ ID NOs:20-37, and the complements thereof.

In some embodiments, the invention encompasses compositions comprising an interfering RNA molecule comprising two or more dsRNAs, wherein the two or more dsRNAs each comprise a different antisense strand. In some embodiments the invention encompasses compositions comprising at least two more interfering RNA molecules, wherein the two or more interfering RNA molecules each comprise a dsRNA comprising a different antisense strand. The two or more interfering RNAs may be present on the same nucleic acid construct, on different nucleic acid constructs or any combination thereof. In other embodiments, the composition comprises a RNA molecule comprising an antisense strand consisting essentially of a nucleotide sequence comprising at least a 19 consecutive nucleotide fragment of any one of SEQ ID NOs:29-37, and in some embodiments may further comprise an RNA molecule comprising an antisense strand consisting essentially of a second nucleotide sequence comprising at least a 19 consecutive nucleotide fragment of any one of SEQ ID NOs:29-37; and in some embodiments may further comprise an RNA molecule comprising an antisense strand consisting essentially of a third nucleotide sequence comprising at least a 19 consecutive nucleotide fragment of the antisense any one of SEQ ID NOs:29-37, and in some embodiments may further comprise an RNA molecule comprising an antisense strand consisting essentially of a fourth nucleotide sequence comprising at least a 19 consecutive nucleotide fragment of the antisense any one of SEQ ID NOs:29-37, and in some embodiments may further comprise an RNA molecule comprising an antisense strand consisting essentially of a fifth nucleotide sequence comprising at least a 19 consecutive nucleotide fragment of the antisense of SEQ ID NO:29-37, and in some embodiments may further comprise an RNA molecule comprising an antisense strand consisting essentially of a sixth nucleotide sequence comprising at least a 19 consecutive nucleotide fragment of the antisense of any one of SEQ ID NOs:29-37, and in some embodiments may further comprise an RNA molecule comprising an antisense strand consisting essentially of a seventh nucleotide sequence comprising at least a 19 consecutive nucleotide fragment of the antisense of any one of SEQ ID NOs:29-37. In other embodiments, the composition may comprise two or more of the nucleic acid molecules, wherein the two or more nucleic acid molecules each encode a different interfering RNA molecule. In other embodiments, the composition may comprise two or more of the nucleic acid constructs, wherein the two or more nucleic acid constructs each comprise a nucleic acid molecule encoding a different interfering RNA.

In other embodiments, the composition comprises two or more nucleic acid constructs, two or more nucleic acid molecules, two or more chimeric nucleic acid molecules, two or more artificial plant microRNA precursors of the invention, wherein the two or more nucleic acid constructs, two or more nucleic acid molecules, two or more chimeric nucleic acid molecules, or two or more artificial plant microRNA precursors, each comprise a different antisense strand.

In some embodiments, the invention encompasses an insecticidal composition for inhibiting the expression of an insect pest gene described herein, comprising at least one interfering RNA of the invention and/or the DNA encoding it and/or the expression construct of the invention and/or a cell (active or inactivated) expressing the RNA molecule of the invention and an agriculturally acceptable carrier. For example, the compositions of the invention may be mixed with water and/or fertilizers and may be applied preemergence and/or postemergence to a desired locus by any means, such as airplane spray tanks, irrigation equipment, direct injection spray equipment, knapsack spray tanks, cattle dipping vats, farm equipment used in ground spraying (e.g., boom sprayers, hand sprayers), and the like. The desired locus may be soil, plants, and the like.

In some embodiments, an acceptable agricultural carrier is a formulation useful for topically applying the insecticidal composition comprising the interfering RNA molecule to a plant or seed. In some embodiments, the formulation may be in any form suitable for application to a plant, a seed or directly to a target insect pest. In one aspect, the formulation may be in solid form (powder, pellet, or a bait), liquid form, or gel form. In some embodiments, the interfering RNA molecules are stabilized against degradation because of their double stranded nature and the introduction of Dnase/Rnase inhibitors. For example, dsRNA or siRNA can be stabilized by including thymidine or uridine nucleotide 3' overhangs. The dsRNA or siRNA contained in the compositions of the invention can be chemically synthesized at industrial scale in large amounts. Methods available would be through chemical synthesis or through the use of a biological agent.

In other embodiments the formulation comprises a transfection promoting agent. In other embodiments, the transfection promoting agent is a lipid-containing compound. In further embodiments, the lipid-containing compound is selected from the group consisting of; Lipofectamine, Cellfectin, DMRIE-C, DOTAP and Lipofectin. In another embodiment, the lipid-containing compound is a Tris cationic lipid.

In some embodiments, the formulation further comprises a nucleic acid condensing agent. The nucleic acid condensing agent can be any such compound known in the art. Examples of nucleic acid condensing agents include, but are not limited to, spermidine (N-[3-aminopropyl]-1,4-butanediamine), protamine sulphate, poly-lysine as well as other positively charged peptides. In some embodiments, the nucleic acid condensing agent is spermidine or protamine sulfate.

In still further embodiments, the formulation further comprises buffered sucrose or phosphate buffered saline.

A composition of the invention may be applied to a seed or plant propagule in any physiological state, at any time between harvest of the seed and sowing of the seed; during or after sowing; and/or after sprouting. It is preferred that the seed or plant propagule be in a sufficiently durable state that it incurs no or minimal damage, including physical damage or biological damage, during the treatment process. A formulation may be applied to the seeds or plant propagules using conventional coating techniques and machines, such as fluidized bed techniques, the roller mill method, rotostatic seed treaters, and drum coaters.

In order to apply an active ingredient to insects and/or crops of useful plants as required by the methods of the invention said active ingredient may be used in pure form or, more typically, formulated into a composition which includes, in addition to said active ingredient, a suitable inert diluent or carrier and optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). SFAs include non-ionic, cationic and/or anionic surfactants, as well as surfactant mixtures. Thus in further embodiments according to any aspect of the invention mentioned hereinbefore, the active ingredient will be in the form of a composition additionally comprising an agriculturally acceptable carrier or diluent.

The compositions can be chosen from a number of formulation types, including dustable powders (DP), soluble powders(SP), water soluble granules (SG), water dispersible granules (WG), wettable powders (WP), granules (GR) (slow or fast release), soluble concentrates (SL), oil miscible liquids(OL), ultra low volume liquids (UL), emulsifiable concentrates(EC), dispersible concentrates (DC), emulsions (both oil in water (EW) and water in oil (EO)), microemulsions(ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the active ingredient.

Dustable powders (DP) may be prepared by mixing the active ingredient with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing the active ingredient with one or more water-soluble inorganicsalts (such as sodium bicarbonate, sodium carbonate ormagnesium sulfate) or one or more water-soluble organicsolids (such as a polysaccharide) and, optionally, one or more wetting agents, one or more dispersing agents or a mixture ofsaid agents to improve water dispersibility/solubility. The mixture is then ground to a fine powder. Similar compositions may also be granulated to form water soluble granules (SG).

Wettable powders (WP) may be prepared by mixing the active ingredient with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of the active ingredient and one or more powdered solid diluents or carriers, or from pre-formed blank granules by absorbing the active ingredient (or a solution thereof, in a suitable agent) in a porous granular material (such as pumice, attapulgite clays, fuller's earth, kieselguhr, diatomaceous earths or ground corn cobs) or by adsorbing the active ingredient(or a solution thereof, in a suitable agent) on to a hardcore material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving the active ingredient in water or an organic solvent, such as a ketone, alcohol or glycol ether. These solutions may contain a surface active agent (for example to improve water dilution or prevent crystallisation in a spray tank). Emulsifiable concentrates (EC) or oil-in-water emulsions (EW) may be prepared by dissolving the active ingredient in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 15060 and SOLVESSO 200; SOLVESSO is a Registered TradeMark), ketones (such as cyclohexanone or methylcyclohexanone) and alcohols (such as benzyl alcohol, furfuryl alcohol or butanol), N-alkylpyrrolidones (such as N-methylpyrrolidoneor N-octylpyrrolidone), dimethyl amides of fatty acids (such as C8-C10 fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining the active ingredienteither as a liquid (if it is not a liquid at room temperature, it may be melted at a reasonable temperature, typically below 70° C.) or in solution (by dissolving it in an appropriate solvent) and then emulsifiying the resultant liquid or solution into water containing one or more SFAs, under high shear, to produce an emulsion. Suitable solvents for use in EW s include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SF As, to produce spontaneously a thermodynamically stable isotropic liquid formulation. The active ingredient is present initially in either the water or the solvent/SPA blend. Suitable solvents for use in MEs include those hereinbefore described for use in ECs or in EWs. A ME may be either an oil-in-water or a water-in-oil system (which system is present may be determined by conductivity measurements) and may be suitable for mixing water-soluble and oil-soluble pesticides in the same formulation. A ME is suitable for dilution into water, either remaining as a microemulsion or forming a conventional oil-in-water emulsion.

Suspension concentrates (SC) may comprise aqueous or non-aqueous suspensions of finely divided insoluble solid particles of the active ingredient. SCs may be prepared by ball or bead milling the solid active ingredient in a suitable medium, optionally with one or more dispersing agents, to produce a fine particle suspension of the compound. One or more wetting agents may be included in the composition and a suspending agent may be included to reduce the rate at which the particles settle. Alternatively, the active ingredient may be dry milled and added to water, containing agents hereinbefore described, to produce the desired end product.

Aerosol formulations comprise the active ingredient and a suitable propellant (for example n-butane). Active ingredients may also be dissolved or dispersed in a suitable medium (for example water or a water miscible liquid, such as n-propanol) to provide compositions for use in non-pressurised, hand-actuated spray pumps. The active ingredient may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains the active ingredient and, optionally, a carrier or diluent therefor. The polymeric shell may be produced by either an interfacial polycondensation reaction or by a coacervation procedure. The compositions may provide for controlled release of the compound of the active ingredient. Active ingredients may also be formulated in a biodegradable polymeric matrix to provide a slow, controlled release of the compound. A composition may include one or more additives to improve the biological performance of the composition (for example by improving wetting, retention or distribution on surfaces; resistance to rain on treated surfaces; or uptake or mobility of the active ingredient). Such additives include surface active agents, spray additives based on oils, for example certain mineral oils, natural plant oils (such as soy bean and rape seed oil) and/or modified plant oils (e.g. esterified plant oils), and blends of these with other bio-enhancing adjuvants (ingredients which may aid or modify the action of the active ingredient. Where the active ingredient described herein is employed in methods of protecting crops of useful plants, methods of enhancing/maintaining yield and/or methods of increasing/maintaining pollination in crops of useful plants, it is preferred that said active ingredient (or compositions containing such active ingredient) is applied to the crop of useful plants at the flower-bud stage. In particular for crops of useful plants wherein said plants have yellow flowers, (e.g. oilseed rape, mustard etc.) it is preferred that the application occurs at the green to yellow bud stage.

In some embodiments, the acceptable agricultural carrier is a transgenic organism expressing an interfering RNA of the invention. In some embodiments the transgenic organism may be a living or a non-living transgenic bacteria expressing the interfering RNA of the invention that when fed upon by a target insct pest causes the target insect pest to stop feeding, growing or reproducing or causing death of the target insect pest. In some embodiments the target insect pest is selected from the group consisting of Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata and Diabrotica virgifera.

In other embodiments, the transgenic organism is selected from, but not limited to, the group consisting of: yeast, fungi, algae, plants, virus or an arthropod expressing the interfering RNA molecule of the invention. In some embodiments, the transgenic organism is a virus, for example an insect baculovirus that expresses an interfering RNA molecule of the invention upon infection of an insect host. Such a baculovirus is likely more virulent against the target insect than the wildtype untransformed baculovirus. In other embodiments the transgenic organism is a transgenic bacterium that is applied to an environment where a target pest occurs or is known to have occurred. In some embodiments, non-pathogenic symbiotic bacteria, which are able to live and replicate within plant tissues, so-called endophytes, or non-pathogenic symbiotic bacteria, which are capable of colonizing the phyllosphere or the rhizosphere, so-called epiphytes, are used. Such bacteria include bacteria of the genera *Agrobacterium, Alcaligenes, Azospirillum, Azotobacter, Bacillus, Clavibacter, Enterobacter, Erwinia, Flavobacter, Klebsiella, Pseudomonas, Rhizobium, Serratia, Streptomyces* and

*Xanthomonas*. Symbiotic fungi, such as *Trichoderma* and *Gliocladium* are also possible hosts for expression of the inventive interfering RNA molecule for the same purpose.

In some embodiments, the invention encompasses transgenic plants, or parts thereof, comprising an interfering RNA molecule, a nucleic acid construct, a chimeric nucleic acid molecule, a artificial plant microRNA precursor molecule and/or a composition of the invention, wherein the transgenic plant has enhanced resistance to at least a coleopteran insect compared to a control plant. The invention further encompasses transgenic seed of the transgenic plants of the invention, wherein the transgenic seed comprises an interfering RNA molecule, a nucleic acid construct, a chimeric nucleic acid molecule, an artificial plant microRNA precursor molecule and/or a composition of the invention.

Transgenic plants expressing an interfering RNA of the invention are tolerant or resistant to attack by target insect pests. When the insect starts feeding on such a transgenic plant, it also ingests the expressed dsRNA or siRNA. This may deter the insect from further biting into the plant tissue or may even harm or kill the insect. A nucleic acid sequence encoding a dsRNA or siRNA of the invention is inserted into an expression cassette, which is then preferably stably integrated in the genome of the plant. The nucleic acid sequences of the expression cassette introduced into the genome of the plant are heterologous to the plant and non-naturally occurring. Plants transformed in accordance with the present invention may be monocots or dicots and include, but are not limited to, corn, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, Arabidopsis, and woody plants such as coniferous and deciduous trees.

Expression of the interfering RNA molecule in transgenic plants is driven by regulatory sequences comprising promoters that function in plants. The choice of promoter will vary depending on the temporal and spatial requirements for expression, and also depending on the insect target species. Thus, expression of the interfering RNAs of this invention in leaves, in stalks or stems, in ears, in inflorescences (e.g. spikes, panicles, cobs, etc.), in roots, and/or seedlings is contemplated. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the dsRNA or siRNA in the desired cell.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

In some embodiments, tissue-specific/tissue-preferred promoters can be used. Tissue-specific or tissue-preferred expression patterns include, but are not limited to, green tissue specific or preferred, root specific or preferred, stem specific or preferred, and flower specific or preferred. In addition, promoters functional in plastids can be used. In some embodiments of the invention, inducible promoters can be used. In further aspects, the nucleotide sequences of the invention can be operably associated with a promoter that is wound inducible or inducible by pest or pathogen infection (e.g., a insect or nematode plant pest)

In some embodiments of the present invention, a "minimal promoter" or "basal promoter" is used. A minimal promoter is capable of recruiting and binding RNA polymerase II complex and its accessory proteins to permit transcriptional initiation and elongation. In some embodiments, a minimal promoter is constructed to comprise only the nucleotides/nucleotide sequences from a selected promoter that are required for binding of the transcription factors and transcription of a nucleotide sequence of interest that is operably associated with the minimal promoter including but not limited to TATA box sequences. In other embodiments, the minimal promoter lacks cis sequences that recruit and bind transcription factors that modulate (e.g., enhance, repress, confer tissue specificity, confer inducibility or repressibility) transcription. A minimal promoter is generally placed upstream (i.e., 5') of a nucleotide sequence to be expressed. Thus, nucleotides/nucleotide sequences from any promoter useable with the present invention can be selected for use as a minimal promoter.

In some embodiments, a recombinant nucleic acid molecule of the invention can be an "expression cassette." As used herein, "expression cassette" means a recombinant nucleic acid molecule comprising a nucleotide sequence of interest (e.g., the nucleotide sequences of the invention), wherein the nucleotide sequence is operably associated with at least a control sequence (e.g., a promoter). Thus, some embodiments of the invention provide expression cassettes designed to express nucleotides sequences encoding the dsRNAs or siRNAs of the invention. In this manner, for example, one or more plant promoters operably associated with one or more nucleotide sequences of the invention are provided in expression cassettes for expression in a corn plant, plant part and/or plant cell.

An expression cassette comprising a nucleotide sequence of interest may be chimeric, meaning that at least one of its components is heterologous with respect to at least one of its other components. An expression cassette may also be one that comprises a native promoter driving its native gene, however it has been obtained in a recombinant form useful for heterologous expression. Such usage of an expression cassette makes it so it is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tml terminator, the nopaline synthase terminator and/or the pea rbcs E9 terminator. These can be used in both monocotyledons and dicotyledons. In addition, a coding sequence's native transcription terminator can be used.

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to the plant, plant part and/or plant cell expressing the marker and thus allows such transformed plants, plant parts and/or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptll, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella ozaenae* that confers resistance to bromoxynil (Stalker et al. (1988) Science 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin. One of skill in the art is capable of choosing a suitable selectable marker for use in an expression cassette of the invention.

An expression cassette of the invention also can include polynucleotides that encode other desired traits. Such desired traits can be other polynucleotides which confer insect resistance, or which confer nematode resistance, or other agriculturally desirable traits. Such polynucleotides can be stacked with any combination of nucleotide sequences to create plants, plant parts or plant cells having the desired phenotype. Stacked combinations can be created by any method including, but not limited to, cross breeding plants by any conventional methodology, or by genetic transformation. If stacked by genetically transforming the plants, nucleotide sequences encoding additional desired traits can be combined at any time and in any order. For example, a single transgene can comprise multiple expression cassettes, such that multiple expression cassettes are introduced into the genome of a transformed cell at a single genomic location. Alternatively, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

Thus, an expression cassette can include a coding sequence for one or more polypeptides for agronomic traits that primarily are of benefit to a seed company, grower or grain processor. A polypeptide of interest can be any polypeptide encoded by a polynucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construct of interest may be preferred. In the case of direct gene transfer, transformation with a single DNA species or co-transformation can be used (Schocher et al. Biotechnology 4:1093-1096 (1986)). For both direct gene transfer and Agrobacterium-mediated transfer, transformation is usually (but not necessarily) undertaken with a selectable marker that may provide resistance to an antibiotic (kanamycin, hygromycin or methotrexate) or a herbicide (basta). Plant transformation vectors of the invention may also comprise other selectable marker genes, for example, phosphomannose isomerase (pmi), which provides for positive selection of the transgenic plants as disclosed in U.S. Pat. Nos. 5,767,378 and 5,994,629, herein incorporated by reference, or phosphinotricin acetyltransferase (pat), which provides tolerance to the herbicide phosphinotricin (glufosinate). The choice of selectable marker is not, however, critical to the invention.

In other embodiments, a nucleic acid sequence of the invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) Proc. Natl. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) EMBO J. 12, 601-606). Substantial increases in transformation frequency are obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleic acid sequence of the present invention is inserted into a plastid-targeting vector and transformed into the plastid genome of a desired plant host. Plants homoplastic for plastid genomes containing a nucleic acid sequence of the present invention are obtained, and are preferentially capable of high expression of the nucleic acid sequence.

Transgenic plants or seed comprising an interfering RNA of the invention can also be treated with an insecticide or insecticidal seed coating as described in U. S. Pat. Nos. 5,849,320 and 5,876,739, herein incorporated by reference. Where both the insecticide or insecticidal seed coating and the transgenic plant or seed of the invention are active against the same target insect, for example a coleopteran pest or a Diabrotica target pest, the combination is useful (i) in a method for further enhancing activity of the composition of the invention against the target insect, and (ii) in a method for preventing development of resistance to the composition of the invention by providing yet another mechanism of action against the target insect. Thus, the invention provides a method of enhancing control of a *Diabrotica* insect population comprising providing a transgenic plant or seed of the invention and applying to the plant or the seed an insecticide or insecticidal seed coating to a transgenic plant or seed of the invention. Examples of such insecticides and/or insecticidal seed coatings include, without limitation, a carbamate, a pyrethroid, an organophosphate, a friprole, a neonicotinoid, an organochloride, a nereistoxin, or a combination thereof. In another embodiment, the insecticide or insecticidal seed coating are selected from the group consisting of carbofuran, carbaryl, methomyl, bifenthrin, tefluthrin, permethrin, cyfluthrin, lambda-cyhalothrin, cypermethrin, deltamethrin, chlorpyrifos, chlorethoxyfos, dimethoate, ethoprophos, malathion, methyl-parathion, phorate, terbufos, tebupirimphos, fipronil, acetamiprid, imidacloprid, thiacloprid, thiamethoxam, endosulfan, bensultap, and a combination thereof. Commercial products containing such insecticides and insecticidal seed coatings include, without limitation, Furadan® (carbofuran), Lanate® (methomyl, metomil, mesomile), Sevin® (carbaryl), Talstar® (bifenthrin), Force® (tefluthrin), Ammo® (cypermethrin), Cymbush® (cypermethrin), Delta Gold® (deltamethrin), Karate® (lambda-cyhalothrin), Ambush® (permethrin), Pounce® (permethrin), Brigade® (bifenthrin), Capture® (bifenthrin), ProShield® (tefluthrin), Warrior® (lambda-cyhalothrin), Dursban® (chlorphyrifos), Fortress® (chlorethoxyfos), Mocap® (ethoprop), Thimet® (phorate), AAstar® (phorate, flucythinate), Rampart® (phorate), Counter® (terbufos), Cygon® (dimethoate), Dicapthon, Regent® (fipronil), Cruiser® (thiamethoxam), Gaucho® (imidacloprid), Prescribe® (imidacloprid), Poncho® (clothianidin) and Aztec® (cyfluthrin, tebupirimphos).

The compositions of the invention can also be combined with other biological control agents to enhance control of a coleopteran insect or a *Diabrotica* insect population. Thus, the invention provides a method of enhancing control of a coleopteran insect population or a Diabrotica insect population by providing a transgenic plant that produces an interfering RNA of the invention and further comprises a polynucleotide that encodes a second insecticidal agent. The second insecticidal agent may be an insecticidal protein derived from Bacillus thuringiensis. A B. thuringiensis insecticidal protein can be any of a number of insecticidal proteins including but not limited to a Cry1 protein, a Cry3 protein, a Cry7 protein, a Cry8 protein, a Cry11 protein, a Cry22 protein, a Cry 23 protein, a Cry 36 protein, a Cry37 protein, a Cry34 protein together with a Cry35 protein, a binary insecticidal protein CryET33 and CryET34, a binary insecticidal protein TIC100 and TIC101, a binary insecticidal protein PS149B1, a VIP, a TIC900 or related protein, a TIC901, TIC1201, TIC407, TIC417,a modified Cry3A protein, or hybrid proteins or chimeras made from any of the preceding insecticidal proteins. In other embodiments, the *B. thuringiensis* insecticidal protein is selected from the group consisting of Cry3Bb1, Cry34Ab1 together with Cry35Ab1, mCry3A and eCry3.1Ab.

In other embodiments, the transgenic plant may produce an interfering RNA of the invention and a second insecticidal agent which is derived from sources other than *B. thuringiensis*. The second insecticidal agent can be an agent selected from the group comprising a patatin, a protease, a protease inhibitor, a chitinase, a urease, an alpha-amylase inhibitor, a pore-forming protein, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus laterosporous* insecticidal protein, a *Lysinibacillus sphaericus* insecticidal protein, a *Chromobacterium* spp. insecticidal protein, a *Yersinia entomophaga* insecticidal protein, a *Paenibacillus popiliae* insecticidal protein, a *Clostridium* spp. (such as *C. bifermentans*) insecticidal protein, and a lignin. In other embodiments, the second agent may be at least one insecticidal protein derived from an insecticidal toxin complex (Tc) from *Photorhabdus, Xenorhabus, Serratia,* or *Yersinia*. In other embodiments. the insecticidal protein may be an ADP-ribosyltransferase derived from an insecticidal bacteria, such as *Photorhabdus* spp. In other embodiments, the insecticidal protein may be a VIP protein, such as VIP1 or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In another embodiment, the transgenic plant and transgenic seed is a corn plant or corn seed. In another embodiment, the transgenic corn plant is provided by crossing a first transgenic corn plant comprising a dsRNA of the invention with a transgenic corn plant comprising a transgenic event selected from the group consisting of MIR604, Event 5307, DAS51922-7, MON863 and MON88017.

Even where the insecticide or insecticidal seed coating is active against a different insect, the insecticide or insecticidal seed coating is useful to expand the range of insect control, for example by adding an insecticide or insecticidal seed coating that has activity against lepidopteran insects to the transgenic plant or seed of the invention, which has activity against coleopteran insects, the treated plant or coated transgenic seed controls both lepidopteran and coleopteran insect pests.

In further embodiments, the invention encompasses a biological sample from a transgenic plant, seed, or parts thereof, of the invention, wherein the sample comprises a nucleic acid that is or encodes at least one strand of a dsRNA of the invention. In other embodiments, the invention encompasses a commodity product derived from a transgenic plant, seed, or parts thereof, of the invention. In some embodiments, the commodity product is selected from the group consisting of whole or processed seeds, beans, grains, kernels, hulls, meals, grits, flours, sugars, sugars, starches, protein concentrates, protein isolates, waxes, oils, extracts, juices, concentrates, liquids, syrups, feed, silage, fiber, paper or other food or product produced from plants. In other embodiments, the biological sample or commodity product is toxic to insects. In other embodiments, the transgenic plant is a transgenic corn plant.

The invention further encompasses a method of controlling at least a coleopteran pest insect comprising contacting the insect with a nucleic acid molecule that is or is capable of producing an interfering RNA molecule of the invention for inhibiting expression of a Rpt5 target gene in the insect thereby controlling the coleopteran insect. In some embodiments, the coleopteran insect is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera*. In some embodiments, the target gene comprises, consists essentially of or consists of a coding sequence(i) having at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:1-9, or a complement thereof; (ii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one SEQ ID NOs:1-9, or a complement thereof; (iii) comprising at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of a nucleotide sequence encoding an amino acid sequence encoded by any one of SEQ ID NOs:1-9, or a complement thereof. In some embodiments the target gene coding sequence comprises, consists essentially of or consists of any one of SEQ ID NOs:1-9, or a complement thereof, or (iv) can hybridize under stringent conditions to a polynucleotide selected from the group consisting of any one of SEQ ID NOs:1-9, and the complements thereof. In other embodiments, the interfering RNA molecule of the invention is complementary to a portion of a mRNA polynucleotide transcribable from the pest insect target genes described herein. In other embodiments, the mRNA comprises, consists essentially of or consists of any one of SEQ ID NOs:29-37.

In some embodiments of the method of controlling a coleopteran insect pest, the interfering RNA molecule of the invention comprises at least one dsRNA, wherein the dsRNA is a region of double-stranded RNA comprising annealed complementary strands, one strand of which comprises a sequence of at least 19 consecutive nucleotides which (i) has at least 80% identity, at least 85% identity, at least 86% identity, at least 87% identity, at least 88% identity, at least 89% identity, at least 90% identity, at least 91% identity, at least 92% identity, at least 93% identity, at least 94% identity, at least 95% identity, at least 96% identity, at least 97% identity, at least 98% identity, at least 99% identity, or 100% identity, to at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37, or the complement thereof; or (ii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of any one of SEQ ID NOs:20-37, or the complement thereof; (iii) comprises at least a 19, at least a 20, at least a 21, at least a 22, at least a 23, at least a 24, at least a 25, at least a 26, at least a 27, at least a 28, at least a 29, at least a 30, at least a 35, at least a 40, at least a 45, at least a 50, at least a 55, at least a 60, at least a a 65, at least a 70, at least a 75, at least a 80, at least a 85, at least a 90, at least a 95, at least a 100, at least a 110, at least a 120, at least a 130, at least a 140, at least a 150, at least a 160, at least a 170, at least a 180, at least a 190, at least a 200, at least a 210, at least a 220, at least a 230, at least a 240, at least a 250, at least a 260, at least a 270, at least a 280, at least a 290, or at least a 600 consecutive nucleotide fragment of a nucleotide sequence encoding an amino acid sequence encoded by any one of SEQ ID NOs:20-37, or the complement thereof, or (iv) can hybridize under stringent conditions to a polynucleotide selected from the group consisting of any one of SEQ ID NOs:20-37, and the complements thereof. In other embodiments, the interfering RNA comprises, consists essentially of or consists of any one of SEQ ID NOs:20-28, and the target gene is a Rpt5 in an insect pest selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera*.

In other embodiments of the method of controlling a coleopteran insect pest, the contacting comprises (a) planting a transgenic seed capable of producing a transgenic plant that expresses the nucleic acid molecule, wherein the insect feeds on the transgenic plant, or part thereof; or (b) applying a composition comprising the nucleic acid molecule to a seed or plant, or part thereof, wherein the insect feeds on the seed, the plant, or a part thereof. In some embodiments, the transgenic seed and the transgenic plant is a corn seed or a corn plant. In other embodiments the seed or plant is a corn seed or a corn plant.

The invention also encompasses a method of controlling a *Diabrotica* insect comprising contacting the *Diabrotica* insect with a nucleic acid molecule that is or is capable of producing the interfering RNA molecule of the invention for inhibiting expression of a target gene in the *Diabrotica* insect, and also contacting the *Diabrotica* insect with at least a second insecticidal agent for controlling *Diabrotica*, wherein said second insecticidal agent comprises a *B. thuringiensis* insecticidal protein, thereby controlling the *Diabrotica* insect. The invention also encompasses a method for controlling *Diabrotica* insect pests on a plant, comprising topically applying to said plant a pesticide composition comprising an interfering RNA of the invention and at least a second insecticidal agent for controlling *Diabrotica*, wherein said second insecticidal agent does not comprise a *B. thuringiensis* insecticidal protein, and providing said plant in the diet of said *Diabrotica* insect. The invention also encompasses a method wherein the second insecticidal agent comprises a patatin, a protease, a protease inhibitor, a urease, an alpha-amylase inhibitor, a pore-forming protein, a lectin, an engineered antibody or antibody fragment, or a chitinase. The second insecticidal agent may also be a *Bacillus cereus* insecticidal protein, a *Xenorhabdus* spp. insecticidal protein, a *Photorhabdus* spp. insecticidal protein, a *Brevibacillus laterosporous* insecticidal protein, a *Lysinibacillus spheari- cus* insecticidal protein, a *Chromobacterium* ssp. insecticidal protein, a *Yersinia entomophaga* insecticidal protein, a *Paenibacillus popiliae* insecticidal protein, or a *Clostridium* spp. insecticidal protein.

The invention also encompasses a method of reducing an adult coleopteran insect population or an adult *Diabrotica* insect population on a transgenic plant expressing a Cry protein, a hybrid Cry protein or modified Cry protein comprising expressing in the transgenic plant a nucleic acid molecule that is or is capable of producing an interfering RNA molecule of the invention capable of inhibiting expression of a target gene as described herein in an adult insect, thereby reducing the adult coleopteran insect population or adult Diabrotica insect population.

In some embodiments, the invention encompasses a method of conferring coleopteran or

*Diabrotica* insect tolerance to a plant, or part thereof, comprising introducing into the plant, or part thereof, an interfering RNA molecule, a dsRNA molecule, a nucleic acid construct, a chimeric nucleic acid molecule, an artificial plant microRNA precursor molecule and/or a composition of the invention, wherein the dsRNA molecule, nucleic acid construct, chimeric nucleic acid molecule, artificial plant microRNA precursor molecule and/or composition of the invention are toxic to the insect, thereby conferring tolerance of the plant or part thereof to the coleopteran insect or *Diabrotica* insect. In other embodiments, the introducing step is performed by transforming a plant cell and producing the transgenic plant from the transformed plant cell. In still other embodiments, the introducing step is performed by breeding two plants together.

In other embodiments, the invention encompasses a method of reducing root damage to a plant fed upon by a *Diabrotica* insect, comprising introducing into cells of the plant an interfering RNA molecule, a dsRNA, a nucleic acid molecule, a nucleic acid construct, a chimeric nucleic acid molecule, an artificial plant microRNA precursor molecule and/or a composition of the invention, wherein the dsRNA, nucleic acid molecule, nucleic acid construct, chimeric nucleic acid molecule, artificial plant microRNA precursor molecule and/or composition of the invention are toxic to the *Diabrotica* insect, thereby reducing root damage to the plant. In other embodiments, the introducing step is performed by transforming a plant cell and producing the transgenic plant from the transformed plant cell. In still other embodiments, the introducing step is performed by breeding two plants together.

In still other embodiments, the invention encompasses a method of producing a transgenic plant cell having toxicity to a coleopteran insect or *Diabrotica* insect of the invention, comprising introducing into a plant cell an interfering RNA molecule, a dsRNA, a nucleic acid molecule, a nucleic acid construct, a chimeric nucleic acid molecule, an artificial plant microRNA precursor molecule and/or a composition of the invention, thereby producing the transgenic plant cell having toxicity to the insect compared to a control plant cell. In some embodiments, the invention encompasses a plurality of transgenic plant cells produced by this method. In other embodiments, the plurality of transgenic plant cells is grown under conditions which include natural sunlight. In other embodiments, the introducing step is performed by transforming a plant cell and producing the transgenic plant from the transformed plant cell. In still other embodiments, the introducing step is performed by breeding two plants together.

In some embodiments, the invention encompasses a method of producing a transgenic plant having enhanced tolerance to at least coleopteranor *Diabrotica* insect feeding damage, comprising introducing into a plant an interfering RNA molecule, a dsRNA, a nucleic acid molecule, a nucleic acid construct, a chimeric nucleic acid molecule, an artificial plant microRNA precursor molecule and/or a composition of the invention, thereby producing a transgenic plant having enhanced tolerance to coleopteran or *Diabrotica* insect feeding damage compared to a control plant. In other embodiments, the introducing step is performed by transforming a plant cell and producing the transgenic plant from the transformed plant cell. In still other embodiments, the introducing step is performed by breeding two plants together.

In some embodiments, the invention encompasses a method of identifying a Rpt5 gene in an insect pest for interfering RNA targeting, said method comprising the steps of: a) isolating nucleic acid from an insect pest; b) amplifying an orthologous Rpt5 target gene from the nucleic acid with a pair of primers comprising nucleotide sequences selected from SEQ ID NOs:38-55; c) identifying a sequence of an orthologous Rpt5 target gene; d) producing a dsRNA molecule, wherein the dsRNA molecule comprises a sense strand and an antisense strand, wherein a nucleotide sequence of the antisense strand is complementary to a portion of a mRNA polynucleotide transcribable from the insect pest Rpt5 gene that comprises a Rpt5 coding sequence, and e) testing the dsRNA molecule of step d) for insecticidal activity against the insect pest. In some embodiments, the insect pest is a coleopteran insect pest. In other embodiments, the coleopteran insect pest is selected from the group consisting of *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera.*

EXAMPLES

The invention will be further described by reference to the following detailed examples.

These examples are provided for the purposes of illustration only, and are not intended to be limiting unless otherwise specified.

Example 1

Identification of Target Genes

For each species, a library of assembled contigs was constructed. These sequences were compared via BLAST to known lethal genes and alleles, which were identified based on published disclosures including those in the website wormbase (wormbase.org) and Boutros et al (2004, Science 303: 832-835). From this analysis, several target genes were identified. Contigs with matches to target genes with an expect value of 1e-10 or lower were considered potentially significant matches. Full-length Rpt5 genes were identified in each of the species.

dsRNA Synthesis of Target Genes dsRNAs of those targets were produced on an 96w automated library synthesis platform. All the dsRNA samples tested were designed automatically using Primer3, a primer design tool, to synthetize a dsRNA fragment of around 600-800 bp based on the coding sequence of each target gene. Smaller fragments were designed if the size of the coding sequence did not allow a 600 bp fragment. The PCR template for dsRNA synthesis was amplified from cDNA that was reverse transcribed using standard methods from mRNA isolated from whole insects. Primers (corresponding to SEQ ID Nos:38-55) containing T7 promoter sequences were used to amplify the fragment of the genes, followed by in vitro transcription, using standard methods, to synthesize dsRNA. The RNA was further purified following standard methods and the pellet was re-suspended in double distilled water. The concentration and quality of each dsRNA sample was analyzed on a Dropsense96 spectrophotometer (Trinean).

Example 2

Activity of dsRNA Molecules Targeting Rpt5

In Vitro Bio-Assay *Meligethes aeneus*

A dsRNA molecule comprising SEQ ID NO:20 which corresponds to SEQ ID NO:11, targeting Rpt5 (SEQ ID NO:1) was tested for toxicity against pollen beetle, *Melighethes aeneus* in laboratory bioassays. In vitro bioassays were performed in 3-cm Petri dishes, using an RNA-treated artificial diet method. Briefly, synthesized dsRNA molecules were diluted to the appropriate concentration in a sucrose solution. Samples containing dsRNA and sucrose are heated up to 60° C. An agarose solution was heated till boiling and added to the dsRNA dilutions leading to final concentrations of 5% sucrose and 0.5% agarose. The agarose solution containing the dsRNA was divided over three Petri dishes, at a final dose of 67 μg of dsRNA per Petri dish. Ten to twelve adults were added to each Petri dish resulting in 30 to 36 adults per treatment. Petri dishes were stored at 25° C. with a 16 hour: 8 hour light:dark photoperiod. Mortality was recorded at 1 or 2, 3, 4, 6, 7, 8 days post-infestation. DsRNA of non-target GFP was used as a negative control and dsRNA designed to target an ubiquitin gene of *Melingethes aeneus* was used as a positive control.

In Vitro Bioassay *Sitophilus oryzae*

A dsRNA molecule comprising SEQ ID NO:21 which corresponds to SEQ ID NO:12, targeting Rpt5 (SEQ ID NO:2) was tested for toxicity against the rice weevil, *Sitophilus oryzae* in laboratory bioassays. In vitro bioassays were performed in 6-well plates, using an RNA-treated artificial diet method. Briefly, synthesized dsRNA molecules were diluted to the appropriate concentration and mixed with Bio flour in a final 9:1 ratio (v/w). The suspension was continuously mixed, divided over three wells at a final dose of 80 μg of dsRNA per well and left to dry. Eight adults were added to each well, resulting in 24 adults per treatment. The plates were stored at 25° C. with a 16 hour: 8 hour light:dark photoperiod.

Mortality was recorded at 3, 5, 7, 10, 12 and 13 days post-set up. DsRNA of non-target GFP was used as a negative control and dsRNA designed to target an ubiquitin gene of *Sitophilus oryzae* was used as a positive control.

In Vitro Bioassay *Sitophilus granarius*

A dsRNA molecule comprising SEQ ID NO:22 which corresponds to SEQ ID NO:13, targeting Rpt5 (SEQ ID NO:3) was tested for toxicity against the grain weevil, *Sitophilus granarius* in laboratory bioassays. In vitro bioassays are performed in 6-well plates using an RNA-treated artificial diet method. Briefly, synthesized dsRNA molecules are diluted to the appropriate concentration in a sucrose solution. Samples containing dsRNA and sucrose are heated up to 60° C. An agarose solution is heated till boiling and added to the dsRNA dilutions, leading to final concentrations of 5% sucrose and 0.5% agarose. The agarose solution containing the dsRNA is divided over three wells, at a final dose of 80 μg of dsRNA per well. Eight adults are added to each well resulting in 24 adults per treatment. Each plate is stored at 25° C. with a 16 hour: 8 hour light:dark photoperiod. Mortality was recorded at 3, 5, 7, 10, 12 and 14 days post-infestation. DsRNA of non-target GFP is used as a negative control and dsRNA designed to target an ubiquitin gene of *Sitophilus granarius* is used as a positive control.

In Vitro Bioassay *Ceutorhynchus assimilis*

A dsRNA molecule comprising SEQ ID NO:23 which corresponds to SEQ ID NO:14, targeting Rpt5 (SEQ ID NO:4) is tested for toxicity against the cabbage seedpod weevil, *Ceutorhynchus assimilis* in laboratory bioassays. In vitro bioassays are performed in 6-well plates using an RNA-treated artificial diet method. Briefly, synthesized dsRNA molecules are diluted to the appropriate concentration in a sucrose solution. Samples containing dsRNA and sucrose are heated up to 60° C. An agarose solution is heated till boiling and added to the dsRNA dilutions, leading to final concentrations of 5% sucrose and 0.5% agarose. The agarose solution containing the dsRNA is divided over three wells, at a final dose of 80 μg of dsRNA per well. Eight adults are added to each well resulting in 24 adults per treatment.

Plates are stored at 25° C. with a 16 hour: 8 hour light:dark photoperiod. Mortality is recorded at 2, 3, 4, 5, 7, and 10 days post-infestation. DsRNA of non-target GFP is used as a negative control and dsRNA designed to target an ubiquitin gene of *Ceutorhynchus assimilis* is used as a positive control.

In Vitro Bioassay *Rhyzopertha dominica*

A dsRNA molecule comprising SEQ ID NO:24 which corresponds to SEQ ID NO:15, targeting Rpt5 (SEQ ID NO:5) was tested for toxicity against lesser grain borer, *Rhyzopertha dominica,* in laboratory bioassays. In vitro bioassays were performed in 24-well plates using an RNA-treated artificial diet method. Briefly, synthesized dsRNA molecules were diluted to the appropriate concentration in a flour suspension. The suspension containing the dsRNA was divided over three wells at a final dose of 100 μg dsRNA per well and left to dry. Ten adults were added to each well resulting in 30 adults per treatment. Plates were sealed and stored at 25° C. with a 16 hour: 8 hour light:dark photoperiod. Mortality was recorded at 1, 2, 5, 6, 7, 8, 9, 12 days post-infestation. DsRNA of non-target GFP was used as a negative control and dsRNA designed to target an ubiquitin gene of *Rhyzoperta dominica* was used as a positive control.

In Vitro Bioassay *Phyllotreta nemorum*

A dsRNA molecule comprising SEQ ID NO:25 which corresponds to SEQ ID NO:16 targeting Rpt5 (SEQ ID NO:6), is tested for toxicity against flea beetles, *Phyllotreta nemorum* in laboratory bioassays. In vitro bioassays are performed in 3 cm Petri dishes using an RNA-treated artificial diet method. Briefly, synthesized dsRNA molecules are diluted to the appropriate concentration in a sucrose solution. Samples containing dsRNA and sucrose is heated up to 60° C. An agarose solution is heated till boiling and added to the dsRNA dilutions, leading to final concentrations of 5% sucrose and 0.5% agarose. The agarose solution containing the dsRNA is divided over three Petri dishes at a final dose of 67 μg dsRNA per Petri dish. Ten to twelve adults are added to each Petri dish resulting in 30 to 36 adults per treatment. Petri dishes are stored at 25° C. with a 16 hour: 8 hour light:dark photoperiod. Mortality is recorded at 1, 2, 5, 6, 7, 8, 9 days post-infestation. DsRNA of non-target GFP is used as a negative control and dsRNA designed to target an ubiquitin gene of *Phyllotreta nemorum* is used as a positive control.

In Vitro Bioassay *Psylliodes chrysocephala*

A dsRNA molecule comprising SEQ ID NO:26 which corresponds to SEQ ID NO:17 targeting Rpt5 (SEQ ID NO:7), was tested for toxicity against flea beetles, *Psylliodes chrysocephala* in laboratory bioassays. In vitro bioassays were performed in 3 cm Petri dishes using an RNA-treated artificial diet method. Briefly, synthesized dsRNA molecules werere diluted to the appropriate concentration in a sucrose solution. Samples containing dsRNA and sucrose was heated up to 60° C. An agarose solution was heated till boiling and added to the dsRNA dilutions, leading to final concentrations of 5% sucrose and 0.5% agarose. The agarose solution containing the dsRNA was divided over three Petri dishes at a final dose of 67 μg dsRNA per Petri dish. Ten to twelve adults were added to each Petri dish resulting in 30 to 36 adults per treatment. Petri dishes were stored at 25° C. with a 16 hour: 8 hour light:dark photoperiod. Mortality was recorded at 1, 2, 5, 6, 7, 8, 9 days post-infestation. DsRNA of non-target GFP was used as a negative control and dsRNA designed to target an ubiquitin gene of *Psylliodes chrysocephala* was used as a positive control.

In Vitro Bioassay *Phyllotreta striolata*

A dsRNA molecule comprising SEQ ID NO:27 which corresponds to SEQ ID NO:18, targeting Rpt5 (SEQ ID NO:8) was tested for toxicity against flea beetle, *Phyllotreta striolata,* in laboratory bioassays. In vitro bioassays were performed in 20 ml plastic cups, using RNA-treated leaf disks. Briefly, synthesized dsRNA molecules were diluted to the appropriate concentration and applied to canola leaf discs (5 mm diameter), coating the top surface with a final dose of 20 ng/mm2. Leaf disks were placed in cups containing ten adults per cup. Adult beetles were fed fresh leaf discs, coated with dsRNA, every second day, for a period of two weeks. The cups were stored at 25° C. with a 16 hour: 8 hour light:dark photoperiod and mortality was recorded every second day. dsRNA of non-target GFP was used as a negative control and dsRNA designed to target an ubiquitin gene of *Phyllotreta striolata* was used as a positive control.

In Vitro Bioassay *Diabrotica virgifera*

A dsRNA molecule comprising SEQ ID NO:28 which corresponds to SEQ ID NO:19, targeting Rpt5 (SEQ ID NO:9) was tested for toxicity against the western corn rootworm, *Diabrotica virgifera virgifera* in laboratory bioassays. In vitro bioassays were performed in 48-well plates using an RNA-treated artificial diet method. Briefly, molten artificial diet, modified from the diet of Marrone et al. 1985 (J. Econ. Entomol. 78:290-293), was poured into each well and allowed to solidify. DsRNA molecules were diluted to appropriate concentration. 20 μl of solution was added to the surface of the diet in half of the wells of a 48-well plate, resulting in a final overlay concentration of 1μg, 0.1 μg, 0.01 μg and 0.001 μg per well. One or two WCR larvae were added to each well to have between 24 and 48 replicate larvae per concentration of dsRNA tested. Plates were stored at 26° C. with a 16 hour: 8 hour light:dark photoperiod. Mortality was recorded at 1, 2, 3, 4, 6 and 7 d post-infestation. DsRNA of non-target GFP was used as a negative control and dsRNA designed to target an ubiquitin gene of *Diabrotica virgifera virgifera* was used as a positive control.

Results of the bioassays described above, shown in Table 1, demonstrate that Rpt5 is an effective target to control coleopteran insect pests *Meligethes aeneus, Sitophilus oryzae, Sitophilus granaries, Ceutorhynchus assimilis, Rhyzopertha dominica, Phyllotreta nemorum, Psylliodes chrysocephala, Phyllotreta striolata* and *Diabrotica virgifera.*

TABLE 1

Activity of dsRNA targeting Rpt5 in coleopteran pests.

Target ID: Rpt5, CG6223

| Insect Pest | | Sequence ID | % Mortality |
|---|---|---|---|
| Nitidulidae | *Meligethes aeneus* | SEQ ID NO: 1 | 88.6 |
| Curculionidae | *Sitophilus oryzae* | SEQ ID NO: 2 | 100 |
| | *Sitophilus granarius* | SEQ ID NO: 3 | 95.8 |
| | *Ceutorhynchus assimilis* | SEQ ID NO: 4 | 68.7 |
| Bostrichidae | *Rhyzopertha dominica* | SEQ ID NO: 5 | 100 |
| Chrysomelidae | *Phyllotreta nemorum* | SEQ ID NO: 6 | 86.7 |
| | *Psylliodes chrysocephala* | SEQ ID NO: 7 | 100 |
| | *Phyllotreta striolata* | SEQ ID NO: 8 | 61.1 |
| | *Diabrotica virgifera* | SEQ ID NO: 9 | 60.0 |
| | *Leptinotarsa decemlineata* | SEQ ID NO: 10 | 100 |

Example 3

Expression of an Interfering RNA Molecule Comprising a dsRNA in Plants

Vector Construction for Agrobacterium-Mediated Transformation

A binary vector comprising at least one expression cassette designed to produce a hairpin RNA (hpRNA) comprising a promoter operably linked to a sense strand of a target nucleic acid sequence, an intron functioning as a loop sequence, a corresponding antisense strand, and a terminator. The binary vector may also comprise a second cassette between the left and right T-DNA borders, designed to express a selectable marker for use in selection of transformed plant cells. The binary vector may also contain selectable markers for selection of transformed bacteria, for example transformed Agrobacterium tumefaciens bacterial cells which contain the binary vector.

Canola Transformation

Canola plant material can be suitably transformed and fertile plants regenerated by many methods which are well known to one of skill in the art. For example, transgenic Brassica napus plants can be produced by Agrobacterium-mediated transformation following the methods taught by Wang et al (2003. Plant Cell Reports 22: 274-281).Transgenic plants may then be assayed for resistance to insect species by a feeding assay, and/or they may be grown to maturity for T1 seed production. T1 plants may be grown and may also be assayed for resistance to insect species by a feeding assay.

A binary vector containing an expression cassette comprising a sequence encoding a hairpin RNA, comprising a sequence of SEQ ID NO:11, targeting Rpt5 (SEQ ID NO:1), is transformed into *Agrobacterium tumefaciens* using standard molecular biology techniques known to those skilled in the art. To prepare the Agrobacteria for transformation cells are cultured in liquid YPC media at 28° C. and 220 rpm overnight.

The vector described above is transformed into canola. Following transformation, selection, and regeneration, plants are tested for the presence of the hairpin dsRNA comprising the RNA sequence encoded by SEQ ID NO:11. Positive plants from the PCR assay are transferred to the greenhouse and tested for resistance to at least *Meligethes aeneus*.

Rice Transformation

Rice plant material can be suitably transformed and fertile plants regenerated by many methods which are well known to one of skill in the art. For example, transgenic rice plants can be produced by Agrobacterium-mediated transformation following the methods taught by Toki et al (1997. Plant Molecular Biology Reporter 15 (1): 16-21). Transgenic plants may then be assayed for resistance to insect species by a feeding assay, and/or they may be grown to maturity for T1 seed production. T1 plants may be grown and may also be assayed for resistance to insect species by a feeding assay.

Wheat Transformation

Wheat plant material can be suitably transformed and fertile plants regenerated by many methods which are well known to one of skill in the art. For example, transgenic wheat plants can be produced by biolistic bombardment following the methods taught by Chang et al (U.S. Pat. No. 5,955,362). Transgenic plants may then be assayed for resistance to insect species by a feeding assay, and/or they may be grown to maturity for T1 seed production. T1 plants may be grown and may also be assayed for resistance to insect species by a feeding assay.

Corn Transformation

Expression vectors for transforming plant cells generally comprised two expression cassettes, a first expression cassette comprising a Ubi1 promoter operably linked to a nucleotide sequence designed to produce a hairpin RNA (hpRNA) comprising SEQ ID NO:27, which is operably linked to a Ubi361 terminator; and a second expression cassette comprising a Ubi1 promoter operably linked to a pmi (phosphomannose isomerase) selected marker coding sequence, which is operably linked to a Ubi1 terminator. The nucleotide sequence in the first expression cassette designed to form a hairpin RNA comprised a nucleotide sequence coding for a sense RNA strand fused to an intron spacer, which functions to form a loop sequence, fused to a nucleotide sequence coding for an antisense RNA strand, and having the general formula, sense strand-intron spacer-antisense strand. The vectors also contained selectable markers for selection in bacteria.

The vectors described above are transformed into maize plants. *Agrobacterium* transformation of immature maize embryos is performed essentially as described in Negrotto et al., 2000, Plant Cell Reports 19: 798-803. For this example, all media constituents are essentially as described in Negrotto et al., supra. However, various media constituents known in the art may be substituted.

Briefly, *Agrobacterium* strain LBA4404 (pSB1) containing a plant transformation plasmid is grown on YEP (yeast extract (5 g/L), peptone (10 g/L), NaCl (5 g/L), 15 g/1 agar, pH 6.8) solid medium for 2-4 days at 28° C. Approximately $0.8 \times 10^9$ *Agrobacterium* are suspended in LS-inf media supplemented with 100 □M As (Negrotto et al., supra). Bacteria are pre-induced in this medium for 30-60 minutes.

Immature embryos from a suitable genotype are excised from 8-12 day old ears into liquid LS-inf +100 μM. As Embryos are rinsed once with fresh infection medium. Agrobacterium solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/1) and silver nitrate (1.6 mg/1) and cultured in the dark for 28° C. for 10 days.

Immature embryos, producing embryogenic callus are transferred to LSD1M0.5S medium. The cultures are selected on this medium for about 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the pini gene and hpRNA encoding sequences by qRT-PCR. Positive plants from the PCR assay are transferred to the greenhouse and subsequently tested for resistance to at least *Diabrotica virgifera* (western corn rootworm) using a root excision assay and/or a whole plant assay.

Root excision assay. Roots are excised from transgenic plants comprising the constructs described above. The excised root is placed on moistened sterile germination paper in small snap-cap petri dishes. Ten corn rootworm first-instar larvae are added to each dish. Data are collected at 48, 72 and 96 hours post-infestation. Roots are scored by counting the number of entry wounds caused by CRW and root scaring severity on a scale from 0-10, with 0 being "no scaring" and 10 being "severe scaring." A scaring score of 0 to about 6 indicates that an hpRNA-Rpt5 plant is positive compared to a negative control hpRNA plant.

Whole plant bioassay. Corn plants growing in 3" pots are infested with at least ~30-75 neonate corn rootworm larvae per plant. For each assay, 3 plants are used as uninfested controls, which typically are a heterozygous plant that performs well in the root excision bioassay, a homozygous plant not tested in the root excision bioassay and negative control plant. These plants acted as controls for growth conditions during the course of the assay. Data are collected 10-14 days after infestation. Evaluations are primarily subjective measures comparing infested test plants to those of uninfested and infested control plants. One visual evaluation that is made was whether the plants show signs of lodging, a condition indicative of severe damage caused by extensive corn rootworm feeding on the root system.

Example 4

Producing dsRNA Molecules by Bacterial Expression

This example describes producing dsRNA molecules engineered against identified insect pests using a bacterial expression system.

Hairpin cassettes are engineered for selected insect target genes as described above. The hairpin cassette comprises a T7 promoter operably linked to an antisense sequence of the target, further linked at the 3'end to a nucleic acid sequence which is capable of forming a loop structure, further linked at the 3'end to the corresponding sense sequence of the target, operably linked at the 3'end to a T7 terminator sequence. The hairpin cassette is introduced into a bacterial expression vector, for example pGCP295, via appropriate restriction sites, for example BamHI and NotI. The vector is then introduced into an *Escherichia coli* strain, for eample, HT115(DE3)GA01, via electroporation using standard methods, and transformants are selected using kanamycin selection.

The bacteria containing the targeted dsRNA expression vector plasmid are grown in defined medium to a specific optical density and induced by addition of IPTG for a specific time period following standard methods and routine optimization. After induction, the bacteria are harvested by centrifugation, and the produced dsRNA molecules are collected.

Example 5

Activity of dsRNA Molecules in a Spray Application Assay

This example describes testing of a sub-set of the identified target dsRNAs of the invention for biological activity against stink bugs when applied as a spray. The production of bacterial lysate is described above.

Plants, e.g. canola plants, are sprayed with a about 15% sucrose solution containing bacterial lysate expressing non-targeting GFP dsRNA and Rpt5 dsRNA molecules from the expression vectors described above. Test insects are then placed on each sprayed plant. Plants are placed in a box coated with fluon PTFE to prevent insect escape and stored in a rearing chamber (26° C., 65% RH, with 16:8 hours 1:d). Photographs are taken on a daily basis to record plant health. Insect survival rate is recorded 3 to 14 days post exposure to the sprayed plant. These experiments are performed using at least *Meligethes aeneus*. A dsRNA of non-target GFP is used as a negative control and a dsRNA designed against a known a lethal gene is used as positive control. Percent mortality of the insect on day 14 is recorded.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. A double stranded RNA (dsRNA) molecule comprising a sense strand and an antisense strand, wherein a nucleotide sequence of the antisense strand is complementary to a portion of at least 27 consecutive nucleotides of a mRNA polynucleotide transcribable from a coleopteran insect Rpt5 gene that comprises a Rpt5 coding sequence i) having from at least about 90% identity to at least about 99% identity to SEQ ID NO:7; or ii) comprises SEQ ID NO:7, and wherein the dsRNA molecule is toxic to at least a coleopteran insect pest.

2. The dsRNA of claim 1, wherein the portion of the mRNA polynucleotide comprises i) at least 27 consecutive nucleotides of SEQ ID NO:35; ii) from at least 27 consecutive nucleotides to at least 600 consecutive nucleotides of SEQ ID NO:35; or iii) SEQ ID NOs:26.

3. The dsRNA of claim 1, wherein the antisense strand comprises the complement of i) at least 27 consecutive nucleotides of SEQ ID NO:35; ii) from at least 27 consecutive nucleotides to at least 600 consecutive nucleotides of SEQ ID NO:35; or iii) SEQ ID NO:26.

4. The dsRNA molecule of claim 1, wherein the nucleotide sequence of the sense strand is substantially or fully complementary to the nucleotide sequence of the antisense strand.

5. The dsRNA molecule of claim 1, wherein the dsRNA is a short hairpin RNA (shRNA) molecule.

6. The dsRNA molecule of claim 1, wherein the coleopteran insect pest is selected from the group consisting of *Melighethes aeneus, Sitophilus oryzae, Sitophilus granaries, Ceutorhynchus assimilis, Rhyzopertha dominica, Phyllotreta nemorum, Phyllotreta striolata, Psylliodes chrysocephala* and *Diabrotica virgifera*.

7. A nucleic acid molecule encoding an interfering RNA, wherein the interfering RNA comprises the dsRNA molecule of claim 1.

8. A recombinant vector comprising a regulatory sequence operably linked to the nucleic acid molecule of claim 7.

9. A bacteria that comprises the recombinant vector of claim 8.

10. An insecticidal composition comprising the dsRNA of claim 1 and an acceptable agricultural carrier.

11. The insecticidal composition of claim 10, comprising at least a second insecticidal agent.

12. The insecticidal composition of claim 11, wherein the second insecticidal agent is a biological agent or a chemical agent.

13. The insecticidal composition of claim 12, wherein i) the biological agent is a *Bacillus thuringiensis* insecticidal protein, a *Bacillus cereus* insecticidal protein, a *Xenorhabdus* spp. spp.insecticidal protein, a patatin, a protease, a protease inhibitor, a urease, an alpha-amylase inhibitor, a pore-forming protein, a lectin, an engineered antibody or antibody fragment, or a chitinase; or ii) the chemical agent is a carbamate, a pyrethroid, an organophosphate, a friprole, a neonicotinoid, an organochloride, a nereistoxin, or a combination thereof.

14. A method of controlling at least a coleopteran insect pest comprising contacting said insect pest with the dsRNA of claim 1, and wherein the dsRNA molecule is toxic to at least the coleopteran insect pest.

15. The method of claim 14, wherein contacting comprises: a) applying a composition comprising the dsRNA molecule or a nucleic acid molecule encoding the dsRNA molecule or a bacteria comprising the dsRNA molecule or the nucleic acid molecule encoding the dsRNA molecule to a seed or plant, or part thereof, wherein the insect pest feeds on the seed, the plant, or a part thereof; or b) planting a transgenic seed capable of producing a transgenic plant that expresses the dsRNA molecule or a nucleic acid molecule encoding the dsRNA, wherein the pest insect feeds on the transgenic plant, or part thereof.

16. The method of claim 15, wherein the coleopteran insect pest is selected from the group consisting *Melighethes aeneus, Sitophilus oryzae, Sitophilus granaries, Ceutorhynchus assimilis, Rhyzopertha dominica, Phyllotreta nemorum, Phyllotreta striolata, Psylliodes chrysocephala* and *Diabrotica virgifera*.

17. A method of controlling at least a coleopteran insect pest comprising contacting the coleopteran insect pest with a nucleic acid molecule that comprises the dsRNA molecule of claim 1 for inhibiting expression of a Rpt5 target gene in the coleopteran insect pest, and contacting the coleopteran insect pest with at least a second insecticidal agent for controlling a coleopteran insect pest.

18. The method of claim 17, wherein the second insecticidal agent is a biological agent or a chemical agent, optionally wherein i) the biological agent is a *Bacillus thuringiensis* insecticidal protein, a *Bacillus cereus* insecticidal protein, a *Xenorhabdus* spp. insecticidal protein, a *Photorhabdus* spp. insecticidal protein, a *Brevibacillus laterosporous* insecticidal protein, a *Lysinibacillus sphearicus* insecticidal protein, a *Chromobacterium* spp. insecticidal protein, a *Yersinia entomophaga* insecticidal protein, a *Paenibacillus popiliae* insecticidal protein, or a *Clostridium* spp. insecticidal protein, a patatin, a protease, a protease inhibitor, a urease, an alpha-amylase inhibitor, a pore-forming protein, a lectin, an engineered antibody or antibody fragment, or a chitinase; or ii) the chemical agent is a carbamate, a pyrethroid, an organophosphate, a friprole, a neonicotinoid, an organochloride, a nereistoxin, or a combination thereof.

\* \* \* \* \*